(12) United States Patent
Arora et al.

(10) Patent No.: US 10,272,000 B2
(45) Date of Patent: Apr. 30, 2019

(54) PATTERNED APERTURED WEBS AND METHODS FOR MAKING THE SAME

(71) Applicant: The Procter & Gamble Company, Cincinnati, OH (US)

(72) Inventors: Kelyn Anne Arora, Cincinnati, OH (US); Jennifer Lynn Dusold, Cincinnati, OH (US); Timothy Ian Mullane, Union, KY (US); Jill Marlene Orr, Liberty Township, OH (US); Margaret Elizabeth Porter, Cincinnati, OH (US); Jennifer Schutte, Cincinnati, OH (US); Donald Carroll Roe, West Chester, OH (US); Ann Cecilia Tapp, West Chester, OH (US); Rachael Eden Walther, Union, KY (US); Stephanie Niezgoda Moss, Cincinnati, OH (US); John Brian Strube, Okeana, OH (US); Amanda Margaret Bicking, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 346 days.

(21) Appl. No.: 14/933,002

(22) Filed: Nov. 5, 2015

(65) Prior Publication Data
US 2016/0129662 A1     May 12, 2016

Related U.S. Application Data

(60) Provisional application No. 62/177,405, filed on Mar. 13, 2015, provisional application No. 62/076,043, filed on Nov. 6, 2014.

(51) Int. Cl.
*A61F 13/512*     (2006.01)
*A61F 13/511*     (2006.01)
(Continued)

(52) U.S. Cl.
CPC .......... *A61F 13/512* (2013.01); *A61F 13/511* (2013.01); *A61F 13/5116* (2013.01);
(Continued)

(58) Field of Classification Search
None
See application file for complete search history.

(56) References Cited

U.S. PATENT DOCUMENTS 3,081,500 A * 3/1963 Griswold ............... D04H 1/736
                                                                         264/119
3,280,229 A * 10/1966 Simons ................ D01D 5/0076
                                                                         118/624
(Continued)

FOREIGN PATENT DOCUMENTS

CN      2408852 Y   * 12/2000
CN      2897211        5/2007
(Continued)

OTHER PUBLICATIONS

Machine Translation of JP 2010075464 A, Apr. 2010 (Year: 2010).*
(Continued)

*Primary Examiner* — Jeffrey A Vonch
(74) *Attorney, Agent, or Firm* — George H. Leal

(57) ABSTRACT

A disposable absorbent article having a topsheet, a backsheet, and an absorbent core disposed therebetween is described herein. The topsheet includes an array of apertures and a first array of structures which are disposed adjacent the array of apertures. A first plurality of the array of apertures is disposed generally parallel to a longitudinal axis, a second plurality of apertures has a first Absolute Feret angle, and a third plurality of apertures has a second Absolute Feret angle. The first Absolute Feret angle is different than the second Absolute Feret angle.

19 Claims, 56 Drawing Sheets

(51) Int. Cl.
*A61F 13/513* (2006.01)
*B32B 3/24* (2006.01)
*B32B 5/02* (2006.01)
*B32B 5/14* (2006.01)
*B32B 3/26* (2006.01)
*A61F 13/514* (2006.01)
*A61F 13/515* (2006.01)
*B32B 5/26* (2006.01)
*B44F 99/00* (2013.01)
*A61F 13/84* (2006.01)
*A61F 13/15* (2006.01)
*A61F 13/51* (2006.01)
*A61F 13/551* (2006.01)

(52) U.S. Cl.
CPC ...... *A61F 13/5123* (2013.01); *A61F 13/5126* (2013.01); *A61F 13/51394* (2013.01); *B32B 3/26* (2013.01); *B32B 3/266* (2013.01); *B32B 5/022* (2013.01); *B32B 5/142* (2013.01); *A61F 13/15699* (2013.01); *A61F 13/515* (2013.01); *A61F 13/51104* (2013.01); *A61F 13/51121* (2013.01); *A61F 13/51305* (2013.01); *A61F 13/51476* (2013.01); *A61F 13/51478* (2013.01); *A61F 13/551* (2013.01); *A61F 2013/15715* (2013.01); *A61F 2013/5127* (2013.01); *A61F 2013/51092* (2013.01); *A61F 2013/51147* (2013.01); *A61F 2013/51165* (2013.01); *A61F 2013/51178* (2013.01); *A61F 2013/51182* (2013.01); *A61F 2013/51186* (2013.01); *A61F 2013/51322* (2013.01); *A61F 2013/51377* (2013.01); *A61F 2013/51486* (2013.01); *A61F 2013/8497* (2013.01); *B32B 5/26* (2013.01); *B32B 2250/03* (2013.01); *B32B 2307/726* (2013.01); *B32B 2555/00* (2013.01); *B32B 2555/02* (2013.01); *B44F 99/00* (2013.01); *D10B 2509/026* (2013.01); *Y10T 428/24314* (2015.01); *Y10T 428/24322* (2015.01); *Y10T 428/24331* (2015.01); *Y10T 442/60* (2015.04); *Y10T 442/66* (2015.04)

(56) References Cited

U.S. PATENT DOCUMENTS

| | | | | |
|---|---|---|---|---|
| 3,485,706 A * | 12/1969 | Evans | ............... | D04H 18/04 162/115 |
| 3,559,648 A | 2/1971 | Mason, Jr. | | |
| 3,655,501 A * | 4/1972 | Tesch | ............... | A47G 27/00 15/104.002 |
| 3,681,182 A * | 8/1972 | Kalwaites | ............... | D04H 1/736 28/105 |
| 3,681,184 A * | 8/1972 | Kalwaites | ............... | D04H 1/74 28/105 |
| 3,756,907 A * | 9/1973 | Heling | ............... | D04H 1/00 162/114 |
| 3,814,101 A | 6/1974 | Kozak | | |
| 3,849,845 A | 11/1974 | Obenaus | | |
| 3,860,003 A * | 1/1975 | Buell | ............... | A61F 13/49017 604/385.25 |
| 3,886,941 A | 6/1975 | Duane et al. | | |
| 3,890,974 A | 6/1975 | Kozak | | |
| 3,911,173 A | 10/1975 | Sprague, Jr. | | |
| 3,929,135 A * | 12/1975 | Thompson | ............... | A61F 13/512 604/385.08 |
| D238,449 S * | 1/1976 | Matsumo | ............... | D5/57 |
| D239,566 S * | 4/1976 | Vogt | ............... | D5/57 |
| 3,949,127 A * | 4/1976 | Ostermeier | ............... | B29C 65/08 428/137 |
| D239,871 S * | 5/1976 | Levesque | ............... | D5/47 |
| 4,306,559 A | 12/1981 | Nishizawa et al. | | |
| 4,323,069 A | 4/1982 | Ahr et al. | | |
| 4,324,246 A | 4/1982 | Mullane et al. | | |
| 4,327,730 A | 5/1982 | Sorensen | | |
| 4,469,734 A * | 9/1984 | Minto | ............... | D04H 1/425 156/148 |
| 4,493,868 A * | 1/1985 | Meitner | ............... | B32B 5/26 428/171 |
| 4,573,986 A | 3/1986 | Minetola et al. | | |
| 4,588,630 A | 5/1986 | Shimalla | | |
| 4,610,678 A | 9/1986 | Weisman et al. | | |
| 4,623,340 A * | 11/1986 | Luceri | ............... | A61F 13/15577 604/370 |
| 4,629,643 A | 12/1986 | Curro et al. | | |
| 4,637,819 A | 1/1987 | Ouellette et al. | | |
| D288,363 S * | 2/1987 | Wallstrom | ............... | D24/125 |
| 4,673,402 A | 6/1987 | Weisman et al. | | |
| 4,676,784 A | 6/1987 | Erdman et al. | | |
| 4,704,112 A | 11/1987 | Suzuki et al. | | |
| 4,741,941 A | 5/1988 | Englebert et al. | | |
| 4,780,352 A | 10/1988 | Palumbo | | |
| 4,785,996 A | 11/1988 | Ziecker et al. | | |
| 4,798,604 A | 1/1989 | Carter | | |
| 4,834,735 A | 5/1989 | Alemany et al. | | |
| 4,840,829 A | 6/1989 | Suzuki et al. | | |
| 4,842,666 A | 6/1989 | Werenicz | | |
| 4,842,794 A * | 6/1989 | Hovis | ............... | B29D 28/00 264/145 |
| 4,888,231 A | 12/1989 | Angstadt | | |
| 5,122,407 A | 6/1992 | Yeo et al. | | |
| 5,147,345 A | 9/1992 | Young et al. | | |
| 5,151,092 A * | 9/1992 | Buell | ............... | A61F 13/15593 604/358 |
| 5,234,423 A | 8/1993 | Alemany et al. | | |
| 5,277,761 A * | 1/1994 | Van Phan | ............... | D21F 11/00 162/109 |
| H1377 H | 11/1994 | Perry | | |
| 5,369,858 A | 12/1994 | Gilmore et al. | | |
| 5,385,773 A | 1/1995 | Yau et al. | | |
| 5,415,640 A * | 5/1995 | Kirby | ............... | A61F 13/512 604/366 |
| 5,433,715 A | 7/1995 | Tanzer et al. | | |
| 5,437,653 A | 8/1995 | Gilman et al. | | |
| D362,120 S | 9/1995 | Suskind et al. | | |
| 5,516,572 A * | 5/1996 | Roe | ............... | D04H 1/56 428/131 |
| 5,518,801 A | 5/1996 | Chappell et al. | | |
| 5,520,673 A | 5/1996 | Yarbrough et al. | | |
| D371,909 S * | 7/1996 | Arnone | ............... | D5/20 |
| 5,536,555 A | 7/1996 | Zelazoski et al. | | |
| D375,844 S * | 11/1996 | Edwards | ............... | D5/1 |
| 5,573,830 A * | 11/1996 | Schulz | ............... | B31F 1/07 162/109 |
| 5,599,335 A | 2/1997 | Goldman et al. | | |
| 5,607,760 A | 3/1997 | Roe | | |
| 5,609,587 A | 3/1997 | Roe | | |
| 5,628,097 A | 5/1997 | Benson et al. | | |
| 5,635,191 A | 6/1997 | Roe et al. | | |
| 5,643,588 A | 7/1997 | Roe et al. | | |
| 5,660,788 A | 8/1997 | Gray et al. | | |
| 5,704,101 A | 1/1998 | Majors et al. | | |
| 5,714,107 A * | 2/1998 | Levy | ............... | D04H 1/54 264/146 |
| 5,735,984 A | 4/1998 | Hoff et al. | | |
| H1732 H | 6/1998 | Johnson | | |
| 5,770,144 A | 6/1998 | James et al. | | |
| 5,797,894 A | 8/1998 | Cadieux et al. | | |
| 5,824,352 A | 10/1998 | Yang et al. | | |
| 5,885,267 A | 3/1999 | Mishima et al. | | |
| 5,895,380 A | 4/1999 | Turi et al. | | |
| 5,897,543 A | 4/1999 | Francis | | |
| 5,916,661 A | 6/1999 | Benson et al. | | |
| D411,921 S * | 7/1999 | Thomas | ............... | D5/1 |
| 5,919,177 A | 7/1999 | Georger et al. | | |
| 5,941,864 A | 8/1999 | Roe | | |
| 5,968,025 A | 10/1999 | Roe et al. | | |
| 5,998,696 A | 12/1999 | Schone | | |
| 6,015,936 A | 1/2000 | Takai et al. | | |
| 6,030,372 A | 2/2000 | Buell et al. | | |

(56) References Cited

U.S. PATENT DOCUMENTS

| | | | |
|---|---|---|---|
| D424,810 S * | 5/2000 | Thomas | D5/1 |
| D426,888 S * | 6/2000 | Ilian | D24/125 |
| D428,267 S * | 7/2000 | Romano, III | D5/2 |
| 6,093,871 A * | 7/2000 | Takai | A61F 13/512 428/131 |
| D428,710 S * | 8/2000 | Romano, III | D5/2 |
| 6,114,595 A | 9/2000 | Moore et al. | |
| 6,117,524 A | 9/2000 | Hisanaka et al. | |
| D431,369 S * | 10/2000 | Thomas | D5/1 |
| 6,168,849 B1 | 1/2001 | Braverman et al. | |
| D439,057 S * | 3/2001 | Bissah | D24/125 |
| 6,206,865 B1 | 3/2001 | Chen et al. | |
| 6,228,462 B1 | 5/2001 | Lee et al. | |
| 6,231,555 B1 | 5/2001 | Lynard et al. | |
| 6,262,331 B1 * | 7/2001 | Nakahata | A61F 13/49011 604/358 |
| 6,270,623 B1 | 8/2001 | Goda et al. | |
| 6,303,208 B1 | 10/2001 | Pelkie | |
| D449,936 S * | 11/2001 | Cohen | D5/37 |
| 6,348,253 B1 * | 2/2002 | Daley | A61F 13/512 428/131 |
| D456,899 S * | 5/2002 | Levy | D24/124 |
| 6,410,823 B1 | 6/2002 | Daley et al. | |
| D460,818 S * | 7/2002 | Levy | D24/124 |
| D461,893 S * | 8/2002 | Gannon | D24/124 |
| D463,137 S * | 9/2002 | Monroe | D5/57 |
| D463,548 S * | 9/2002 | Gannon | D24/124 |
| D463,549 S * | 9/2002 | Gannon | D24/124 |
| 6,452,064 B1 | 9/2002 | Thoren et al. | |
| 6,454,747 B1 | 9/2002 | Shimada et al. | |
| 6,468,626 B1 | 10/2002 | Takai et al. | |
| 6,479,130 B1 | 11/2002 | Takai et al. | |
| 6,498,284 B1 | 12/2002 | Roe | |
| 6,506,473 B1 | 1/2003 | Hisanaka et al. | |
| 6,534,149 B1 | 3/2003 | Daley et al. | |
| 6,586,653 B2 * | 7/2003 | Graeme, III | A61F 13/511 604/358 |
| 6,610,391 B2 | 8/2003 | Molee | |
| 6,620,490 B1 * | 9/2003 | Malchow | B32B 7/04 428/196 |
| 6,632,504 B1 | 10/2003 | Gillespie et al. | |
| 6,676,646 B2 | 1/2004 | Bast et al. | |
| 6,716,441 B1 | 4/2004 | Osborne et al. | |
| 6,830,800 B2 * | 12/2004 | Curro | A47L 1/15 428/131 |
| 6,849,065 B2 | 2/2005 | Schmidt et al. | |
| 6,849,319 B2 | 2/2005 | Cree et al. | |
| D503,230 S * | 3/2005 | Christianson | D24/125 |
| D506,317 S * | 6/2005 | Hallberg | D5/57 |
| D506,874 S * | 7/2005 | Farahat | D5/20 |
| D507,413 S * | 7/2005 | Farahat | D5/20 |
| D510,435 S * | 10/2005 | Christianson | D24/125 |
| D511,001 S * | 10/2005 | Christianson | D24/125 |
| 6,989,075 B1 * | 1/2006 | Kao | A61K 8/0208 162/123 |
| 6,996,851 B2 | 2/2006 | Nordness et al. | |
| 7,005,558 B1 | 2/2006 | Johansson et al. | |
| D516,319 S * | 3/2006 | Hasenoehrl | D5/1 |
| 7,033,340 B1 | 4/2006 | Muscat et al. | |
| D522,139 S * | 5/2006 | Schluter | D24/125 |
| 7,118,639 B2 | 10/2006 | DeLucia et al. | |
| D542,409 S * | 5/2007 | Wannaborworn | D24/125 |
| D551,342 S * | 9/2007 | Kelly | D24/124 |
| 7,371,919 B1 | 5/2008 | Busam et al. | |
| D574,079 S * | 7/2008 | Fernandez Picon | D24/124 |
| D581,523 S * | 11/2008 | Macaulay | D24/124 |
| D581,524 S * | 11/2008 | Macaulay | D24/124 |
| D583,466 S * | 12/2008 | Dobrin | D24/124 |
| D612,491 S * | 3/2010 | Sullivan Conrad | D24/124 |
| D614,766 S * | 4/2010 | Hernandez | D24/125 |
| D623,420 S * | 9/2010 | Mercer | D5/37 |
| 7,803,244 B2 | 9/2010 | Siqueira et al. | |
| D626,217 S * | 10/2010 | Sealfon | D24/124 |
| D632,496 S * | 2/2011 | Nugent | D5/32 |
| 7,964,801 B2 | 6/2011 | Shih | |
| 8,022,267 B2 | 9/2011 | Hellstrom et al. | |
| D656,740 S * | 4/2012 | Nugent | D5/25 |
| 8,186,296 B2 | 5/2012 | Brown et al. | |
| D664,645 S * | 7/2012 | Larson | D24/125 |
| 8,226,625 B2 | 7/2012 | Turner et al. | |
| 8,226,626 B2 | 7/2012 | Turner et al. | |
| 8,231,595 B2 | 7/2012 | Turner et al. | |
| D668,332 S * | 10/2012 | Hough | D24/124 |
| D674,894 S * | 1/2013 | Hood | D24/124 |
| 8,388,594 B2 | 3/2013 | Turner et al. | |
| D692,130 S * | 10/2013 | Biggs | D24/125 |
| D693,131 S * | 11/2013 | Wang | D5/60 |
| D696,029 S * | 12/2013 | Seyler | D5/1 |
| D703,445 S * | 4/2014 | Lishnevsky | D5/37 |
| D708,444 S * | 7/2014 | Love | D5/37 |
| D708,860 S * | 7/2014 | Duck | D5/60 |
| D725,915 S * | 4/2015 | Haverfield | D5/59 |
| D770,041 S * | 10/2016 | Rubio | D24/125 |
| D784,706 S * | 4/2017 | McClain | D5/1 |
| 2001/0005540 A1 | 6/2001 | Hisanaka et al. | |
| 2001/0053901 A1 | 12/2001 | Mizutani et al. | |
| 2002/0013563 A1 | 1/2002 | Lassen et al. | |
| 2002/0028624 A1 | 3/2002 | Mizutani et al. | |
| 2002/0034914 A1 * | 3/2002 | De Leon | A61F 13/534 442/384 |
| 2002/0062113 A1 | 5/2002 | Thomas et al. | |
| 2002/0062115 A1 | 5/2002 | Wada et al. | |
| 2002/0172371 A1 | 11/2002 | Baker et al. | |
| 2002/0182396 A1 | 12/2002 | DeLucia et al. | |
| 2003/0003269 A1 | 1/2003 | Lee et al. | |
| 2003/0004481 A1 | 1/2003 | Matsuoka et al. | |
| 2003/0021951 A1 * | 1/2003 | Desai | A61F 13/512 428/131 |
| 2003/0050618 A1 * | 3/2003 | Kondo | A61F 13/512 604/383 |
| 2003/0056893 A1 * | 3/2003 | DeLucia | A61F 13/53708 156/276 |
| 2003/0059574 A1 * | 3/2003 | Thomas | A61F 13/512 428/156 |
| 2003/0109839 A1 | 6/2003 | Costea et al. | |
| 2003/0116291 A1 * | 6/2003 | Zoeller | B29C 65/086 162/123 |
| 2003/0125687 A1 * | 7/2003 | Gubernick | A61F 13/2051 604/383 |
| 2003/0145517 A1 | 8/2003 | Miller | |
| 2003/0149412 A1 | 8/2003 | Damaghi et al. | |
| 2003/0171730 A1 * | 9/2003 | Kelly | A61F 13/512 604/383 |
| 2003/0217945 A1 | 11/2003 | Kiene et al. | |
| 2004/0013852 A1 * | 1/2004 | Curro | A61F 13/15593 428/131 |
| 2004/0043189 A1 | 3/2004 | Huang | |
| 2004/0092902 A1 | 5/2004 | Hoffman et al. | |
| 2004/0118811 A1 | 6/2004 | Stone et al. | |
| 2004/0122396 A1 | 6/2004 | Maldonado et al. | |
| 2004/0127128 A1 | 7/2004 | Thomas | |
| 2004/0127875 A1 | 7/2004 | Hammons et al. | |
| 2004/0161586 A1 | 8/2004 | Cree et al. | |
| 2004/0162536 A1 | 8/2004 | Becker et al. | |
| 2004/0181199 A1 | 9/2004 | Moberg-Alehammar et al. | |
| 2004/0209042 A1 | 10/2004 | Peacock | |
| 2004/0241399 A1 * | 12/2004 | Marmon | D04H 3/14 428/196 |
| 2005/0003152 A1 * | 1/2005 | Thomas | A61F 13/4902 428/131 |
| 2005/0027270 A1 | 2/2005 | Cree et al. | |
| 2005/0096614 A1 | 5/2005 | Perez et al. | |
| 2005/0148971 A1 | 7/2005 | Kuroda et al. | |
| 2005/0148973 A1 | 7/2005 | Tamura et al. | |
| 2005/0158513 A1 * | 7/2005 | Peacock | A61F 13/0273 428/136 |
| 2005/0163967 A1 * | 7/2005 | Steffen | B32B 3/266 428/138 |
| 2005/0202208 A1 | 9/2005 | Kelly | |
| 2005/0244619 A1 | 11/2005 | Kauschke et al. | |
| 2005/0256475 A1 | 11/2005 | Komatsu et al. | |
| 2005/0288647 A1 | 12/2005 | Ellingson et al. | |

(56) References Cited

U.S. PATENT DOCUMENTS

| | | |
|---|---|---|
| 2006/0019063 A1 | 1/2006 | Kelly |
| 2006/0020251 A1* | 1/2006 | Kelly ............... A61F 13/15203 |
| | | 604/378 |
| 2006/0058761 A1 | 3/2006 | Kudo et al. |
| 2006/0069361 A1 | 3/2006 | Olson |
| 2006/0087053 A1* | 4/2006 | O'Donnell ................ B26F 1/18 |
| | | 264/156 |
| 2006/0129114 A1* | 6/2006 | Mason, Jr. ......... A61F 13/15203 |
| | | 604/361 |
| 2006/0129115 A1* | 6/2006 | Visscher ........... A61F 13/55145 |
| | | 604/361 |
| 2006/0141885 A1 | 6/2006 | Cobbs et al. |
| 2006/0142710 A1* | 6/2006 | Kigata ................ A61F 13/4751 |
| | | 604/361 |
| 2007/0048498 A1 | 3/2007 | Cree |
| 2007/0073254 A1 | 3/2007 | Ponomarenko et al. |
| 2007/0088307 A1 | 4/2007 | Arizti et al. |
| 2007/0135787 A1* | 6/2007 | Raidel .............. A61F 13/15707 |
| | | 604/383 |
| 2007/0256286 A1 | 11/2007 | Ngai |
| 2008/0065035 A1* | 3/2008 | Perneborn ............. A61F 13/532 |
| | | 604/367 |
| 2008/0138574 A1 | 6/2008 | Maschino et al. |
| 2008/0294135 A1* | 11/2008 | Hara ................ A61F 13/15203 |
| | | 604/367 |
| 2008/0294138 A1 | 11/2008 | Andersson et al. |
| 2008/0312622 A1 | 12/2008 | Hundorf et al. |
| 2009/0030390 A1 | 1/2009 | Hammons et al. |
| 2009/0030391 A1 | 1/2009 | Hammons et al. |
| 2009/0082746 A1 | 3/2009 | Thomas et al. |
| 2009/0104831 A1 | 4/2009 | Bornemann et al. |
| 2009/0131896 A1 | 5/2009 | Ebitsuka et al. |
| 2009/0157021 A1* | 6/2009 | Sullivan ............ A61F 13/51496 |
| | | 604/359 |
| 2009/0233046 A1 | 9/2009 | Iulianetti |
| 2009/0247978 A1 | 10/2009 | Boissier |
| 2009/0259208 A1* | 10/2009 | Hellstrom ............. A61F 13/512 |
| | | 604/383 |
| 2009/0299316 A1 | 12/2009 | Seyler |
| 2010/0004615 A1 | 1/2010 | Boissier |
| 2010/0019415 A1 | 1/2010 | Stone et al. |
| 2010/0035014 A1 | 2/2010 | Hammons et al. |
| 2010/0036338 A1 | 2/2010 | Hammons et al. |
| 2010/0036346 A1* | 2/2010 | Hammons ............. A61F 13/512 |
| | | 604/378 |
| 2010/0036349 A1* | 2/2010 | Hammons ......... A61F 13/51305 |
| | | 604/385.01 |
| 2010/0100067 A1 | 4/2010 | Pugliese, III |
| 2010/0130952 A1 | 5/2010 | Murai |
| 2010/0164733 A1 | 7/2010 | Ales et al. |
| 2010/0168707 A1* | 7/2010 | Nishikawa .......... A61F 13/4704 |
| | | 604/383 |
| 2010/0196653 A1 | 8/2010 | Curro et al. |
| 2010/0201024 A1* | 8/2010 | Gibson ................. B29C 43/22 |
| | | 264/156 |
| 2010/0233438 A1 | 9/2010 | Stone et al. |
| 2010/0280471 A1 | 11/2010 | Shah |
| 2010/0330326 A1 | 12/2010 | Turner et al. |
| 2011/0046592 A1* | 2/2011 | Nishikawa .......... A61F 13/4756 |
| | | 604/367 |
| 2011/0106036 A1 | 5/2011 | Stahl et al. |
| 2011/0160691 A1* | 6/2011 | Ng ........................ B32B 3/10 |
| | | 604/385.23 |
| 2011/0184370 A1 | 7/2011 | Seyler et al. |
| 2011/0196330 A1* | 8/2011 | Hammons ............. A61F 13/512 |
| | | 604/383 |
| 2011/0305870 A1 | 12/2011 | Curro et al. |
| 2011/0311751 A1* | 12/2011 | Feldmann ............... B26F 1/22 |
| | | 428/43 |
| 2011/0313385 A1* | 12/2011 | Hammons ........... A61F 13/4756 |
| | | 604/378 |
| 2012/0003423 A1 | 1/2012 | Cree |
| 2012/0035566 A1 | 2/2012 | Sagisaka et al. |
| 2012/0095426 A1 | 4/2012 | Visscher et al. |
| 2012/0282436 A1* | 11/2012 | Coe .......... B29C 55/18 |
| | | 428/131 |
| 2012/0296304 A1 | 11/2012 | Choo et al. |
| 2013/0012898 A1 | 1/2013 | Bergendahl et al. |
| 2013/0139666 A1 | 6/2013 | Raidel et al. |
| 2014/0031779 A1 | 1/2014 | Hammons et al. |
| 2014/0087130 A1 | 3/2014 | Seyler et al. |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0296809 A1* | 10/2014 | Hammons ........... A61F 13/4751 |
| | | 604/365 |
| 2014/0296815 A1 | 10/2014 | Takken et al. |
| 2014/0303581 A1* | 10/2014 | Karlsson ................ A61F 5/455 |
| | | 604/361 |
| 2014/0324009 A1* | 10/2014 | Lee ....................... A61F 13/512 |
| | | 604/384 |
| 2014/0336605 A1* | 11/2014 | Hardie ................ A61F 13/512 |
| | | 604/369 |
| 2015/0282998 A1* | 10/2015 | Arizti ............. A61F 13/51108 |
| | | 604/385.101 |
| 2015/0283003 A1* | 10/2015 | Rosati ................ A61F 13/5126 |
| | | 206/526 |
| 2015/0284892 A1* | 10/2015 | Galie ....................... D06C 3/06 |
| | | 28/165 |

FOREIGN PATENT DOCUMENTS

| | | | |
|---|---|---|---|
| CN | 201505226 | 6/2010 | |
| CN | 201618014 | 11/2010 | |
| CN | 201855363 | 6/2011 | |
| CN | 202724134_Origi U | 2/2013 | |
| CN | 101940514 B | 12/2013 | |
| DE | 2806401 | 8/1979 | |
| DE | 19647459 A1 | 5/1998 | |
| DE | 19846857 C1 | 10/1998 | |
| EP | 0165807 A1 | 12/1985 | |
| EP | 0495212 A1 | 7/1992 | |
| EP | 0535579 A1 | 4/1993 | |
| EP | 0589224 A1 | 3/1994 | |
| EP | 0545423 B1 | 8/1997 | |
| EP | 0749737 B1 | 11/1999 | |
| EP | 0749738 B1 | 11/1999 | |
| EP | 0749736 B1 | 1/2000 | |
| EP | 0983758 A1 | 3/2000 | |
| EP | 0749739 B1 | 11/2000 | |
| EP | 1086676 A1 | 3/2001 | |
| EP | 0749740 B1 | 12/2001 | |
| EP | 1250901 A1 | 10/2002 | |
| EP | 1066006 B1 * | 5/2003 | ........ A61F 13/51401 |
| EP | 1022007 B1 | 3/2006 | |
| EP | 2710990 A1 | 3/2014 | |
| EP | 2347872 A3 | 1/2015 | |
| GB | 2103933 A * | 3/1983 | ........ A61F 13/15731 |
| GB | 2103933 B | 9/1985 | |
| GB | 2235652 A * | 3/1991 | ............... B32B 5/26 |
| GB | 2225724 B | 7/1992 | |
| GB | 2296464 A | 7/1996 | |
| GB | 2310606 A * | 9/1997 | ........... A61F 13/512 |
| GB | 2310606 B | 9/1999 | |
| JP | 06038818 | 2/1994 | |
| JP | 2587116 B2 | 3/1997 | |
| JP | H10272152 | 10/1998 | |
| JP | 2004188077 A * | 7/2004 | |
| JP | 2009006002 A * | 1/2009 | |
| JP | 2009178384 A * | 8/2009 | |
| JP | 4357591 B1 | 11/2009 | |
| JP | 2010024573 A * | 2/2010 | |
| JP | 2010051697 A * | 3/2010 | |
| JP | 2010075464 A * | 4/2010 | |
| JP | 2010213910 A * | 9/2010 | |
| JP | 2010269029 | 12/2010 | |
| JP | 2011135979 | 7/2011 | |
| JP | 2011239835 | 12/2011 | |
| JP | 2012050548 A2 | 3/2012 | |

(56) References Cited

FOREIGN PATENT DOCUMENTS

| KR | 20010064584 A | | 7/2001 |
|---|---|---|---|
| KR | 20010064584 A | * | 7/2001 |
| WO | WO199110415 A2 | | 7/1991 |
| WO | WO199311726 A1 | | 6/1993 |
| WO | WO199315701 A1 | | 8/1993 |
| WO | WO199513773 A1 | | 5/1995 |
| WO | WO199517867 A2 | | 7/1995 |
| WO | WO199610481 A1 | | 4/1996 |
| WO | WO199611107 A1 | | 4/1996 |
| WO | WO199619313 A1 | | 6/1996 |
| WO | WO199702133 A2 | | 1/1997 |
| WO | WO199703818 A1 | | 2/1997 |
| WO | WO1997009020 A1 | | 3/1997 |
| WO | WO1997011661 A1 | | 4/1997 |
| WO | WO200001334 A1 | | 1/2000 |
| WO | WO200037249 A1 | | 1/2000 |
| WO | WO200028929 A1 | | 5/2000 |
| WO | WO2000062826 A1 | | 10/2000 |
| WO | WO200172251 A1 | | 10/2001 |
| WO | WO2002100632 A1 | | 12/2002 |
| WO | WO2003015681 A1 | | 2/2003 |
| WO | WO2003071019 A1 | | 8/2003 |
| WO | WO2004009009 A1 | | 1/2004 |
| WO | WO2004098474 A1 | | 11/2004 |
| WO | WO2007001320 A1 | | 1/2007 |
| WO | WO2012014957 | | 2/2012 |
| WO | WO2012052172 A1 | | 4/2012 |
| WO | WO2013091150 A1 | | 6/2013 |
| WO | WO2014085974 A1 | | 6/2014 |
| WO | WO2015157254 A1 | | 10/2015 |

OTHER PUBLICATIONS

Machine Translation of JP 2010213910 A, Sep. 2010 (Year: 2010).*
Machine Translation of JP 2010051697 A, Mar. 2010 (Year: 2010).*
14084 International Search Report and Written Opinion (PCT/US2015/059242) dated Feb. 3, 2016.
14085 Search Report and Written Opinion (PCT/US2015/059245) dated Mar. 11, 2016.
All Office Actions, U.S. Appl. No. 14/933,015.
All Office Actions, U.S. Appl. No. 14/933,021.
All Office Actions, U.S. Appl. No. 14/933,024.
All Office Actions, U.S. Appl. No. 14/933,030.
All Office Actions, U.S. Appl. No. 14/933,034.
All Office Actions, U.S. Appl. No. 14/933,039.

* cited by examiner

PATTERNED APERTURED WEBS AND METHODS FOR MAKING THE SAME

CROSS-REFERENCE TO RELATED APPLICATION

This application claims priority under 35 U.S.C. § 119(e) to U.S. Provisional Patent Application Ser. No. 62/076,043, filed on Nov. 6, 2014, and 62/177,405, filed on Mar. 13, 2015, the entire disclosures of which are hereby incorporated by reference.

FIELD

The present disclosure generally relates to apertured webs and methods for making the same. The apertured webs are particularly suited for use in disposable absorbent articles, such as diapers, adult incontinence products, training pants, feminine hygiene products, wipes, dusting substrates, cleaning substrates, and any other suitable consumer products.

BACKGROUND

Apertured webs are sometimes useful in disposable absorbent products and other consumer products. These apertured webs typically have uniformly sized and shaped circular or ovate apertures throughout their area. The circular or ovate apertures are also typically uniformly spaced in the cross machine direction and in the machine direction with respect to each other. These uniform aperture patterns provide webs that have the same amount of fluid penetration and/or absorbency throughout their area owing to the uniform circular or ovate aperture designs. Furthermore, land areas (i.e., non-apertured portions) in these apertured webs typically have the same size, shape, orientation, and spacing with respect to each other. While such uniform apertured webs may be desirable in some applications, other applications would benefit from aperture patterns that combine a plurality of apertures into arrays and that create non-uniformly sized, shaped, and/or spaced land areas. Additionally, other features in conjunction with or independent from aperture patterns would be beneficial.

SUMMARY

Apertured webs of the present invention may be utilized in any suitable disposable absorbent article. In some forms of the present invention, the apertured webs may have non-uniformly sized, shaped, and/or spaced (CD or MD) land areas at least partially surrounding arrays of apertures. Each of the apertures may have the same or different size, space, orientation, and/or spacing relative to another aperture within the array. The apertures may be configured in a patterned fashion disclosed herein or maybe similarly spaced from adjacent apertures.

The present disclosure also provides laminates comprising one or more of the apertured webs or one or more of the apertured webs and one or more non-apertured materials (e.g., films, nonwovens, wovens). In the laminates, colored layers or materials may be positioned intermediate the one or more apertured webs or the one or more apertured webs and the one or more non-apertured materials. The colored layers or material may also be positioned under the apertured webs or laminates having at least one apertured web. The colored layers or materials may comprise colored adhesives, inks, or other colored materials, such as nonwovens, for example. The colored layers or materials may be apertured or non-apertured, patterned, or non-patterned. In some forms, the apertured web may comprise a plurality of apertures which are arranged in a pattern or may comprise uniform rows/columns of apertures.

In some forms, a disposable absorbent article comprises a longitudinal axis and a lateral axis generally perpendicular to the longitudinal axis. A pair of side edges extends generally parallel to the longitudinal axis and a pair of end edges joining said pair of side edges on opposite ends of the disposable absorbent article. A topsheet comprises a web having a length generally parallel to the longitudinal axis and a width generally parallel to the lateral axis. An array of apertures forms apertured indicia and comprises a first plurality of apertures are generally parallel to the longitudinal axis, a second plurality of apertures having a first Absolute Feret Angle, and a third plurality of apertures having a second Absolute Feret Angle. The first Absolute Feret Angle and the second Absolute Feret Angle are different. The disposable absorbent article further comprises a backsheet; and an absorbent core disposed between the topsheet and the backsheet.

In some forms, a disposable absorbent article comprises a longitudinal axis and a lateral axis generally perpendicular to the longitudinal axis. A pair of side edges extends generally parallel to the longitudinal axis and a pair of end edges joining said pair of side edges on opposite ends of the disposable absorbent article. A topsheet comprises a web having a length generally parallel to the longitudinal axis and a width generally parallel to the lateral axis, and an array of apertures forming apertured indicia. A first plurality of apertures having a first Absolute Feret Angle, a second plurality of apertures and a third plurality of apertures having a second Absolute Feret Angle are comprised by the array of apertures, wherein the first Absolute Feret Angle and the second Absolute Feret Angle are different. The disposable absorbent article further comprises a backsheet and an absorbent core disposed between the topsheet and the backsheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Figure 1:
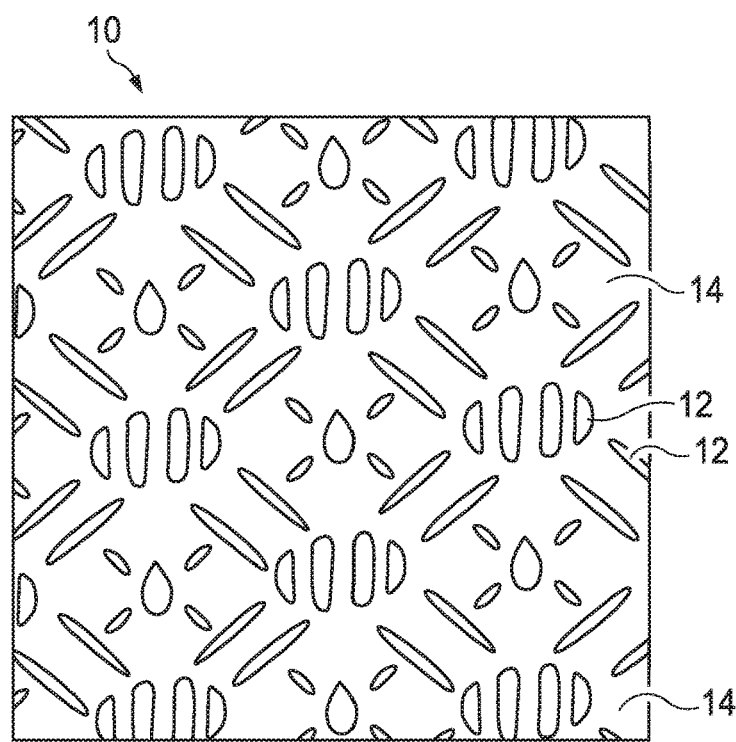
FIGS. 1-4 are photographs of portions of example single layer apertured webs in accordance with the present disclosure.
Figure 2:
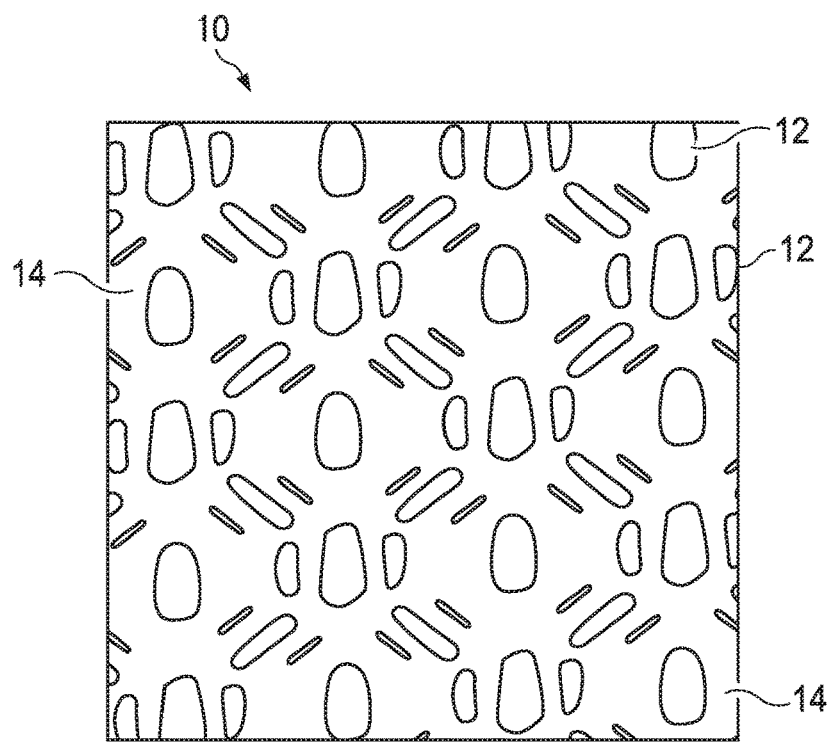
Figure 3:
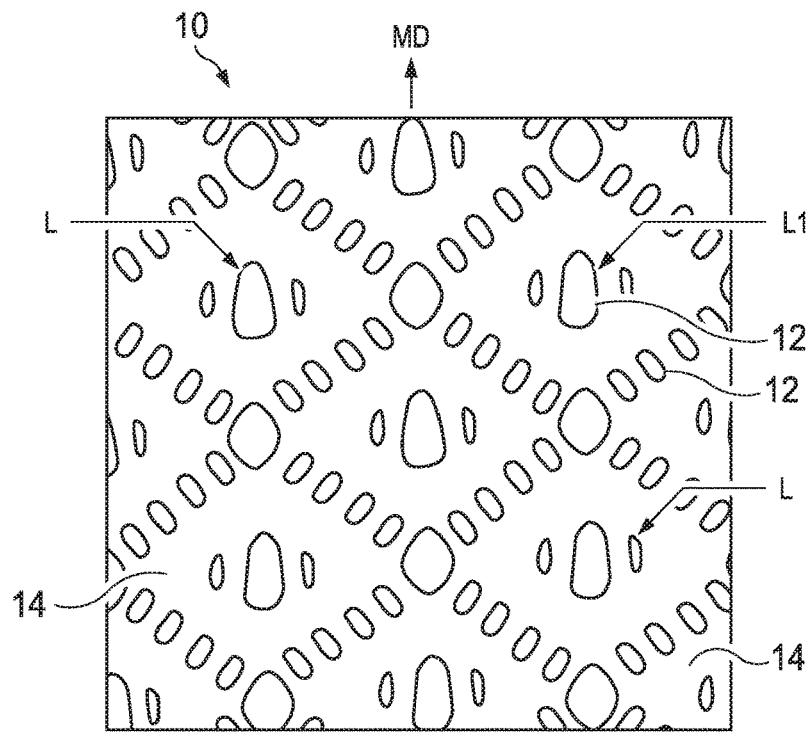
Figure 4:
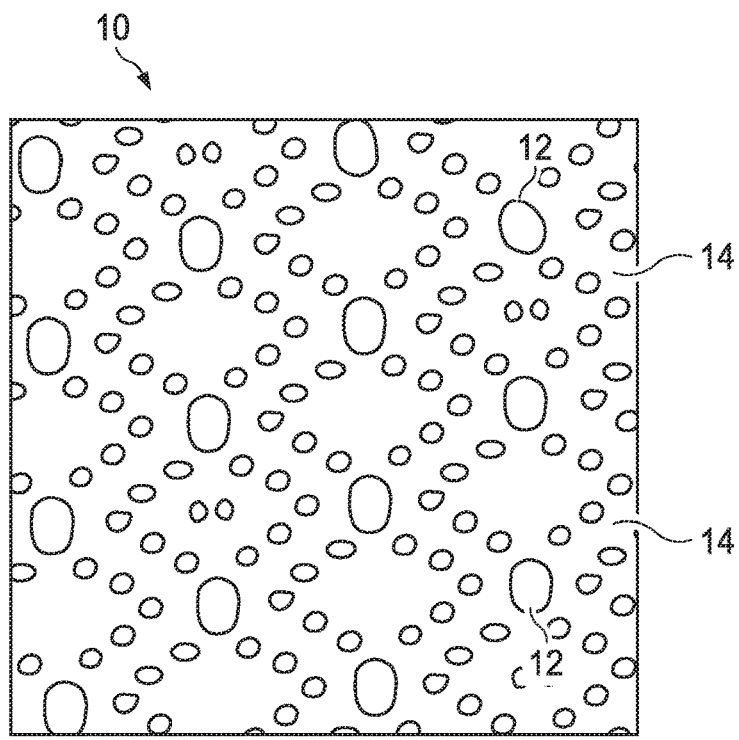

Various non-limiting forms of the present disclosure will now be described to provide an overall understanding of the principles of the structure, function, manufacture, and use of the apertured webs and methods for making the same disclosed herein. One or more examples of these non-limiting forms are illustrated in the accompanying drawings. Those of ordinary skill in the art will understand that the apertured webs and methods for making the same specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "nonwoven material" is used in its normal sense and specifically, refers to a web that has a structure of individual fibers or threads which are interlaid, but not in any regular, repeating manner. Nonwoven materials have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "nanofibers", refers to very small diameter fibers having an average diameter less than about 1 micron.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carded by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

As used herein, the term "polymer" generally includes, but is not limited to, homopolymers, copolymers, such as, for example, block, graft, random, and alternating copolymers, terpolymer, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the terms "join", "joined", "joining", "bond", "bonded", "bonding", "attach", "attached", or "attaching" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "elastic" refers to any material that, upon application of a biasing force, can stretch to an elongated length of at least about 110% of its relaxed, original length (i.e., can stretch to 10 percent), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). "Elastic" may refer to a single material, or it may refer to a combination of materials making up a laminate or a macrostructure in an article. An elastic material may be incorporated into a laminate or macrostructure which is not elastic, or which is less elastic than one or more of the elastic materials of the laminate or macrostructure.

As used herein, the term "nonelastic" refers to any material which does not fall within the definition of "elastic" above.

As used herein, the term "extensible" refers to any material which, upon application of a biasing force, is elongatable by at least about 10 percent, at least about 20, or at least about percent 50 percent, without experiencing catastrophic failure. Recovery of the strain is not required for a material to be considered extensible.

As used herein, the term "melt-stabilized" refers to portions of a nonwoven material which have been subjected to localized heating and/or localized pressure to substantially consolidate the fibers of the nonwoven material into a stabilized film-like form.

As used herein, the term "absorbent article", refers to devices which absorb and contain body exudates, and, more specifically, refers to devices which are placed against or in proximity to the body of the wearer to absorb and contain the various bodily exudates discharged from the body. The term absorbent article includes, but is not limited to, diapers, pants, training pants, adult incontinence products, sanitary napkins, tampons, wipes, and liners. The term "absorbent article" also encompasses cleaning or dusting pads or substrates that have some absorbency.

The term "machine direction" (MD) is used herein to refer to the primary direction of material, strip of substrate, or article flow through a process.

The term "cross direction" (CD) is used herein to refer to a direction that is generally perpendicular to the machine direction.

As used herein, the term "aperture aspect ratio" is the ratio of the major axis to the minor axis of a single aperture.

Apertured Webs

The apertured webs of the present disclosure provide many benefits over conventional apertured topsheets, as will be described herein. Examples of apertured webs 10 are illustrated in FIGS. 1-4, 14-16, and 72-81. As illustrated, the apertured webs 10 may take on a number of configurations. The apertures are labeled 12 and the land areas (non-apertured areas) are labeled 14. A number of additional example apertured web configurations are illustrated in subsequent figures.

The apertured webs of the present disclosure may comprise a single apertured layer (see FIGS. 1-4) or more than one layer), for example, two or three layers. In such constructions, not all layers are required to be apertured. As such, webs of the present invention may comprise a single layer or may be constructed as a laminate. The term "layer" means a self-sustaining web (e.g., a nonwoven or a film) and not a non-self-sustaining web (e.g., a spun layer of an SMMS nonwoven). Thus, a Spunbond-Meltblown-Meltblown-Spunbond (SMMS) nonwoven material would be considered a single layer for purposes of this disclosure, much like a film would be considered a single layer.

The apertured web may comprise one or more non-apertured layers that have not been put through an aperturing process, but merely have openings (if any) created in the formation of the material (e.g., pores in nonwovens). If two apertured layers are provided in an apertured web, each layer may have the same aperturing pattern or a different aperturing pattern. However, as noted previously, in some forms, the apertured web may comprise a single layer.

For those forms where the apertured webs comprise multiple layers, each layer may comprise a plurality of substrates, e.g. SMMS. Other suitable substrates include spunbonded "S"; meltblown "M"; spunlace "SL"; carded "C"; and fine fiber substrates "N". Suitable substrate combinations include SMS, SNS, SMNS and the like. Spunbonded, meltblown, and carded nonwovens are well known in the art. Fine fiber substrates include fibers with average diameters less than one micron or 1000 nanometers.

Figure 5:
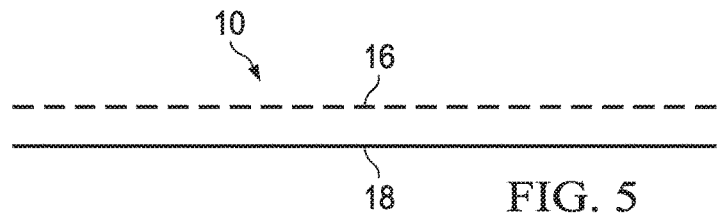
FIG. 5 is a schematic representation of a cross-sectional view of a apertured web having two layers, with one layer being apertured and the other layer being non-apertured in accordance with the present disclosure.

Referring to FIG. 5, a schematic illustration of an example cross-sectional view of an apertured web 10 is illustrated. The apertured web 10 may comprise an apertured layer 16 and a non-apertured layer 18. The apertured layer 16 may comprise any of the various aperture patterns disclosed herein. The aperture layer 16 may be combined with, bonded to, or joined to the non-apertured layer 18 to form a laminate. The apertured layer 16 may have apertures and land areas at least partially surrounding the apertures.

If both or all layers of an multi-layer apertured web are apertured, the apertures may be aligned or overlapping, not aligned or not overlapping, or partially aligned or partially overlapping in the Z-direction. For instance, the apertures in one layer may be 100% aligned or overlapping in the Z-direction with the apertures in a second layer thus forming apertures through both layers of the apertured web. In other instances, the apertures may be less than 100% aligned or overlapping in the Z-direction. Stated another way, the apertures in one layer may be offset in the CD, MD, or other direction or different patterns of apertures may be formed in each layer to create the misalignment of the apertures. In such instances, the area of the apertures in one layer may overlap the area of the apertures in another layer, in the Z-direction, by 10% to 90%, 10% to 100%, 25%, 50%, or 75%, for example, specifically reciting all 0.5% increments within the specified ranges and all ranges formed therein or thereby.

In instances where more than one layer of an apertured web includes apertures, the apertures may be coincident in the Z-direction, i.e., penetrate through both layers. In a form, this may be achieved by forming the apertures after bonding, joining and/or laminating the two or more layers together. Alternatively, the apertures in one layer may have a different pattern, size, and/or shape from the apertures in a second layer and/or may be oriented in a different direction. In a form, this may be achieved by forming the apertures in each of the layers prior to combining the two or layers into a laminated structure. In absorbent article forms comprising an apertured web having an apertured layer and a non-apertured layer, the apertured layer may be oriented on the wearer-facing side of the apertured web or on the garment-facing side of the apertured web. In still other forms, the apertured layer may be positioned intermediate two non-apertured layers.

Any of the layers of the apertured web described herein may be hydrophilic or hydrophobic. In some instances, all of the layers may be hydrophilic or may all be hydrophobic. In still other instances, all of, or some of, the layers may be hydrophilic to different extents or hydrophobic to different extents. In a form, a first layer of an apertured web may have the same or a different hydrophilicity as another layer of the same apertured web. At least one of the layers comprises apertures. As an example, a wearer-facing layer of an apertured web may be hydrophobic to help keep the wearer feeling dry and fresh while a garment-facing layer of the apertured web may be hydrophilic to help wick fluid into the apertures and into an absorbent core. For those instances where a single layer apertured web is utilized, constituent substrates of the single layer may have differing hydrophilic/hydrophobic properties. For those instances where the apertured web comprises a plurality of layers, a constituent substrate of a first layer may have differing hydrophilic/hydrophobic properties from a constituent substrate of a second layer.

In an instance, again referring to FIG. 5, the apertured layer 16 may have a different color than the non-apertured layer 18, such that the apertures in the layer 16 are easily visible or more readily apparent to a user. The aperture pattern in the apertured layer 16 may also form indicia ("apertured indicia") that may indicate the correct orientation of an absorbent article comprising the apertured web 10 on a wearer. Such apertured indicia may include any object or shape that has a commonly understood vertical orientation, such as a heart shape, a face, a building, a letter or numeral, a car, for example. This may also apply to other apertured webs described herein, regardless of how many apertured or non-apertured layers are provided.

Any of the apertured webs described herein may have gradients of color to indicate which side of the product comprising the web is the top and which side is the bottom.

The layers of the apertured web of the present disclosure may have the same basis weight or a different basis weight. In an instance, again referring to FIG. 5, the layer 16 may have a higher basis weight than the layer 18. This may provide better softness on a surface of the layer 16 (e.g., a topsheet contacting a wearer's skin), while also providing enhanced fluid penetration owing to the apertures in the layer 16.

The basis weight of a apertured web may in the range of about 10 gsm to about 200 gsm, about 10 gsm to about 100 gsm, about 10 gsm to about 50 gsm, or about 10 gsm to about 40 gsm, specifically reciting all 0.1 gsm increments within the above-specified range and all ranged formed therein or thereby. Basis weight is measured according to the Basis Weight Method herein.

The predominant fiber orientation of the fibers in the layers of multi-layered apertured webs may be the same or different. In an instance, a predominant fiber orientation may be about 45 degrees to about 135 degrees, for example, off-axis relative to a machine direction, while another layer may have a predominant fiber orientation substantially along a machine direction or +/− about 10 to about 20 degrees from the machine direction. Providing different layers in an apertured web with different predominant fiber orientations may provide increased strength and resistance to tearing of the apertured web when the two or more layers are joined or bonded together.

Figure 6:
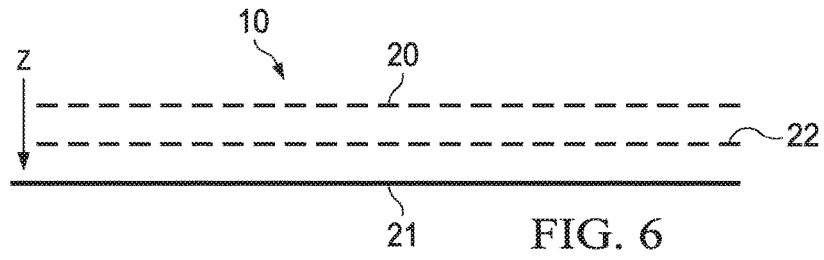
FIG. 6 is a schematic representation of a cross-sectional view of a apertured web having two layers, with both layers being apertured and with the apertures in the layers being aligned in accordance with the present disclosure.

Referring to FIG. 6, a schematic illustration of an example cross-sectional view of another apertured web 10 is illustrated. The apertured web 10 may comprise a first apertured layer 20 and a second apertured layer 22. Apertures of the first apertured layer 20 in FIG. 6 may be 80%, 85%, 90%, 95%, 80% to 100%, or 100% aligned, in the Z-direction (indicated by arrow Z), with apertures the second apertured layer 22, specifically reciting all 0.5% increments within the specified range and all ranges formed therein. The first apertured layer 20 may be combined with, bonded to, or joined to the second patterned aperture layer 22 to form a laminated apertured web. The apertured web 10 of FIG. 6, or any of the other apertured webs of the present disclosure, may comprise a third layer 21 (or more than three layers) that may be non-apertured or apertured. The second apertured layer 22 may be combined with, bonded to, or joined to the third non-apertured layer 21.

Again referring to FIG. 6, the apertures in the second apertured layer 22 may be smaller than (e.g., 10% less area, 20% less area, 30% less area etc.) the apertures in the first apertured layer 20. Such a feature may allow BM penetration through the first layer 20 while also providing adequate liquid bodily exudate fluid strikethrough through the second layer 22 or rewet from the first layer compared to a non-apertured second layer.

Figure 7:
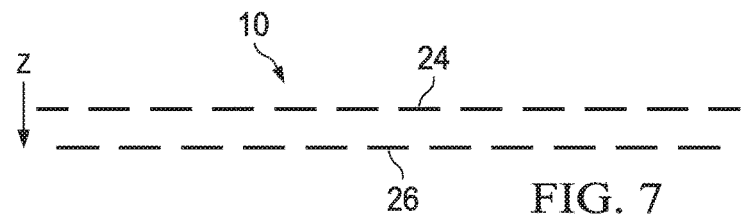
FIG. 7 is a schematic representation of a cross-sectional view of a apertured web having two layers, with both layers being apertured and with the apertures in one layer being fully overlapped by land areas in the other layer in accordance with the present disclosure.

Referring to FIG. 7, a schematic illustration of an example cross-sectional of another apertured web 10 is illustrated. The apertured web 10 may comprise a first apertured layer 24 and a second apertured layer 26. Apertures of the first apertured layer 24 may be fully overlapped by non-apertured portions or "land areas" of the second apertured layer 26 in the Z-direction (indicated by arrow Z). The first apertured layer 24 may be combined with, bonded to, or joined to the second patterned aperture layer 26 to form a laminated apertured web.

Figure 8:
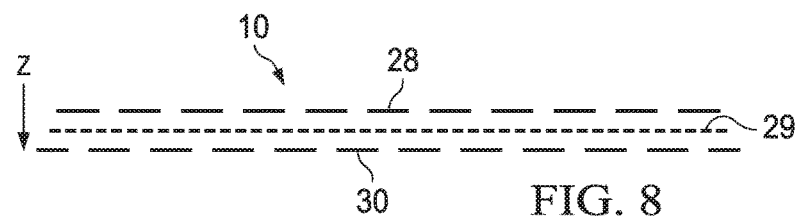
FIG. 8 is a schematic representation of a cross-sectional view of a apertured web having two layers, with both layers being apertured and with the apertures in one layer being partially overlapped by land areas in the other layer in accordance with the present disclosure.

Referring to FIG. 8, a schematic illustration of an example cross-sectional view of another apertured web 10 is illustrated. The apertured web 10 may comprise a first apertured layer 28 and a second apertured layer 30. Apertures of the first apertured layer 28 may be partially overlapped by non-apertured portions or "land areas" of the second apertured layer 30 in the Z-direction (indicated by arrow Z). The first apertured layer 28 may be combined with, bonded to, or joined to the second apertured layer 30 to form a laminated apertured web. The overlap of the areas of the apertures in the first apertured layer 28 and the areas of the apertures in the second apertured layer may be in the range of about 5% to about 95%, about 10% to about 90%, about 20% to about 80%, about 25% to about 75%, about 25%, about 50%, or about 75%, specifically reciting all 0.5% increments within the specified ranges and all ranges formed therein or thereby.

The example apertured web 10 of FIG. 8 may also comprise a pigmented substance (full continuous layer) or a patterned pigmented substance 29 at least partially intermediate the first and second apertured layers 28 and 30. The pigmented substance or patterned pigmented substance 29 may comprise graphics, inks, pigmented adhesives or other pigmented substances and may be viewable through the overlapping areas of the apertures from either side of the apertured web 10. The pigmented substance or patterned pigmented substance 29 may be positioned under the second apertured layer 30 and may still be viewable through the overlapping areas of the apertures when viewing from the first apertured layer 28. The pigmented substance 29 may be viewable through the apertured layer 28. For those instances where the pigmented substance 29 is disposed on a side of the second apertured layer 30 not between the first and second apertured patterned layers can be visible through both the first and second apertured layers 28 and 30.

The first apertured layer 28, the second apertured layer 30, and the pigmented substance or the patterned pigmented substance 29 may be the same color or may each be a different color. Alternatively, the apertured layers 28 and 30 may have a different color as the pigmented substance or the patterned pigmented substance 29. Such forms allow for a three-dimensional appearance to be provided in the apertured web 10 without actually making the apertured web 10 three-dimensional, such as through embossing, for example.

Forms of the present invention are contemplated where the pigmented substance 29 is associated with an apertured layer, e.g. first apertured layer 28, and a non-apertured layer, e.g. third layer 21 (shown in FIG. 6). In such forms, a portion of the pigmented substance 29 may be viewable through the apertures and another portion of the pigmented substance 29 may be viewable through the lands of the apertured layer and/or non-apertured layer.

Materials

Any of the layers of the apertured webs described herein may comprise any materials known in the art including, but not limited to, nonwovens, wovens, cellulosic materials, films, elastic materials, non-elastic materials, highloft materials, and/or foams. The apertured webs may also comprise one or more layers of one or more nonwoven materials, one or more films, combinations of different nonwoven materials, combinations of different films, combinations of one or more films and one or more nonwoven materials, or combinations of one or more different materials, for example. Apertured webs having one or more layers of the same or similar materials are also within the scope of the present disclosure. The basis weight, color, opacity, hydrophilcity, Interaperture Distance, Absolute Feret Angle, Effective Aperture Area, Effective Open Area, or other parameters or characteristics of the various materials in the various layers may be the same or different.

For those instances where the apertured web comprises a plurality of substrates, each substrate may be integrally formed with one another. For example, all substrates of a layer may be produced via a spunbond process. A first substrate may be produced by a first spin beam and a second substrate may be produced via a second spin beam. Additional substrates may be produced via additional spin beams on the same spunbond manufacturing line.

Some precursor web materials may comprise PE/PP bi-component fiber spunbond webs. Other suitable precursor webs may comprise spunbond webs comprising side-by-side crimped fibers (e.g. PE/PP or PP/PP) that are bonded via calendar (thermal point) bonding or through-air bonding. For those configurations with multiple layers a first layer and second layer of the apertured web of the present invention may comprise a crimped spunbond layer. For these configurations, the crimped spunbond layers may be combined from roll stock and joined as provided herein. However, where the apertured web comprises a first substrate and a second substrate, each may be crimped spunbond substrates formed on a spunbond manufacturing line where the first substrate is formed from a first spin beam while the second substrate is formed from a second spin beam.

Other suitable precursor webs may comprise carded staple fibers comprising polypropylene, polyethylene terephthalate, polyethylene/polypropylene bi-component, polyethylene/polyethylene terephthalate bi-component, or the like, which are calendar bonded, through-air bonded, resin bonded or hydroentangled. The precursor webs may comprise microfibers and/or nanofibers, optionally with other fibers. In some circumstances, multiple layer webs may be desired over a single layer webs (even at the same basis weight) due to increased uniformity/opacity and the ability to combine webs having different properties. For example, an extensible spunbond nonwoven carrier layer may be combined with a soft, crimped fiber nonwoven (spunbond or carded) to create an apertured web that is both soft and strong. The layers may have the same or different surface energy, for example, the top layer may be hydrophobic and the lower layer may be hydrophilic. The layers may have different permeability/capillarity, e.g. the upper layer may have higher permeability and the lower layer have higher capillarity in order to set up a capillary gradient and aid in moving fluid away from the surface (or topsheet) of an absorbent article and into an absorbent core of the absorbent article.

Further regarding coloration, the webs of the present invention may comprise pigments, inks or dyes to achieve any color difference as provided herein. The fibers of the first layer and the fibers of the second layer may differ from each other in pigmentation. As used herein, to "differ in pigmentation" or "difference in pigmentation" means (a) the constituent material of a first layer comprises a pigment which is different from the pigment of a second layer; or (b) the constituent material of a first layer comprises a different combination of pigments; or (c) the constituent material of a first layer comprise different amounts of the same pigment(s) versus a second layer; or (d) combinations of any of options a) to c). The pigment or colorant may be added uniformly throughout the constituent material within each layer or may be added to one or both components in same or different type/amount within multicomponent fibers.

A pigment is a material, which can be organic or inorganic and may include activatable, structural and or special effects pigments. A pigment changes the color of reflected or transmitted light as the result of wavelength-selective absorption. This physical process differs from fluorescence, phosphorescence, and other forms of luminescence, in which a material emits light. A pigment is a generally insoluble powder, which differs from a dye, which either is itself a liquid or is soluble in a solvent (resulting in a solution). Dyes are often used to provide a print on the surface of a nonwoven web, such as graphics, pattern or images. Hence, these dyes do not form a part of the fibers of the nonwoven web but are rather applied on the web surface. In the present invention the pigments may be comprised within the fibers of the multilayered nonwoven web, which eliminates the risk of rub-off or wash-off of the color(s) imparted to the multilayered nonwoven web by the pigment.

For the present invention, the pigment will typically be mixed with the thermoplastic material, of which the fibers are made. Often, the pigment is added to the thermoplastic material in the form of a master batch or concentrate at the time of formation of the fibers. Colored master batches useful for the present invention include polypropylene based custom color master batches e.g. supplied by Ampacet; Lufilen and Luprofil supplied by BASF; Remafin for polyolefin fibers, Renol-AT for polyester fibers, Renol-AN for polyamide fibers and CESA for renewable polymers supplied by Clariant. Hence, the pigment will be suspended in the molten thermoplastic material prior to the thermoplastic material being forced through the spinnerets to form and lay down the fibers which form the nonwoven web.

To increase the whiteness and/or opacity of the fibers in either or both layers, titanium dioxide (TiO2) may be used. Different crystal forms are available, however most preferred are rutile or anatase TiO2. Other white pigments include zinc oxide, zinc sulfide, lead carbonate or calcium carbonate. To create a black color, carbon black or any other suitable colorant may be used. Various colored inorganic pigments may be used depending upon the desired color and may include metal oxides, hydroxides and sulfides or any other suitable material. Non-limiting examples of inorganic pigments include cadmium orange, iron oxide, ultramarine, chrome oxide green. One or more pigments may be combined to create the desired color. Non-limiting examples of organic colorants include anthraquinone pigments, azo pigments, benzimidazolone pigments, BONA Lakes, Dioxazine, Naphthol, Perylene, Perinone, Phthalocyanine, Pyranthrone, Quinacridones. Effects pigments including metal, pearlescent and fluorescent may also be used. Various colorants are described in *Plastics Additives Handbook,* 5th Edition.

Webs of the present invention may additionally comprise hydrophobic and/or hydrophilic treatments. Such treatments may be in the form of melt additives and/or spray/coat on chemistries. Some suitable examples of hydrophilic treatments include: Techmer PPM15560; Techmer TPM12713; Polyvel VW351 PP Wetting Agent; Goulston Hydrosorb 1001; as well as those hydrophilic additive disclosed in US Patent Application Publication No. 2012/0077886. One suitable examples of hydrophobic treatments include Techmer PPM17000 High Load Hydrophobic. Other examples of hydrophobic additives are disclosed in U.S. patent application Ser. No. 14/849,630.

Joining of Layers

If more than one layer is provided in a particular apertured web, the layers may be bonded together using any bonding methods known to those of skill in the art, such as adhesive bonding, patterned adhesive coating, ultrasonic bonding, thermal bonding, mechanical bonding, or any combination of these bonding methods. Alternatively, the various layers may be bonded together only at the perimeter of the apertures, through the overbonding step. The bonding may be done in a pattern of bonds or in arrays of bonds. The pattern may be a regular, uniform pattern or an irregular, non-uniform pattern. The bonding patterns may comprise a substantially continuous bond pattern or may be formed of discrete bonding points. The discrete bonding points may form a pattern. The pattern of bonding points may be homogeneous or non-homogeneous. A bond pattern in one region of a apertured web may differ from a bond pattern in another region of the apertured web. For example, the bond pattern may be different in the machine direction or the cross-machine direction of the apertured web laminate. An absorbent article including the apertured web may have a different bond pattern in the front region vs. the back region, the center region vs. side regions, or the crotch region vs. waist regions of the absorbent article, for example. Bonding in apertured webs is typically accomplished by joining the land areas of various layers of the apertured webs. If adhesive is used in the bonding process, the adhesive may be tinted, pigmented, and/or patterned to create a complementary or contrasting pattern compared to the aperture pattern or patterns.

Any suitable method may be utilized to form bonds between layers/substrates described herein. Some suitable examples are ultrasonic, heated rolls, and the like. In a specific example, substrates, layers and/or elements of a disposable absorbent articles may be bonded together via fusion bonding, ultrasonic bonding, or the like. The bonding may comprise a pattern or a plurality of patterns which form graphics and/or other depictions, hereafter "bond indicia". In another example, substrates, layers and/or elements of disposable absorbent articles may be adhesively bonded together.

The mechanical bonding methods, e.g. fusion bond, ultrasonic, etc. can cause localized areas of the web to thin and become film like—in the case of nonwovens. These thinner areas can have different opacity characteristics with respect to the constituent material around the bond. As such, visual/color effects can be achieved. For example, the thinner areas may appear as a different color than the constituent material around the bond.

Some examples of bond indicia are shown in FIGS. 62-66. In order to ensure the integrity of the product and of a topsheet, the total area of the bonding (calculated as a percent area of the outer perimeter of bonding region) may range from 5% to 25%, 10% to 20%, or 12% to 18%. The size of each individual bond nub may range from 0.5 sqmm to 5 sqmm, 1 sqmm to 3 sqmm. The spacing between bond nubs can range from 1 mm to 5 cm, 1.6 mm to 3 cm.

In some forms, the bonds, as stated previously, may be configured in patterns so as to create bond indicia. But apart from forming bond indicia, the bonds can help secure the layers of material together. Additionally, in some forms, the bonds may be utilized to secure a topsheet to subjacent layers of a disposable absorbent article, e.g. a secondary topsheet, absorbent core, etc.

As shown in FIGS. 62-66, bond patterns 3000A, 3000B, 3000C, and 3000D of the present invention may comprise a plurality of bond sites 3002. The bond sites may be any suitable shape. As shown, the bond sites are approximately circular; however, elliptical, diamond, heart, star, clover (3 leaf, 4 leaf), bowtie, combinations thereof, and the like are contemplated. In some forms, the constituent bond sites 3002 of a bond pattern may comprise combinations of shapes.

Figure 66:
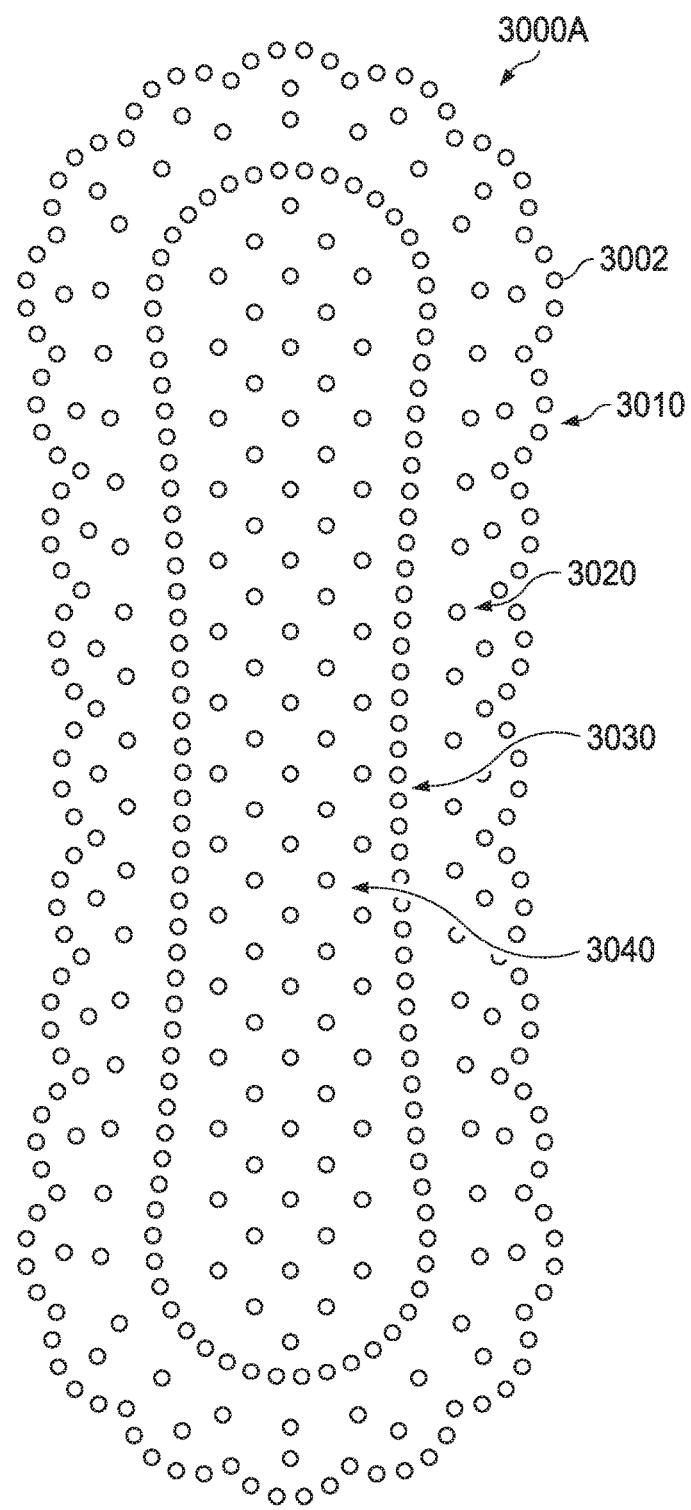
FIGS. 66-69 represent schematic illustrations of bond patterns for materials of the present invention.

As shown in FIG. 66, the bond pattern 3000A may comprise a plurality of arrays of bond sites, e.g. 3010, 3020, 3030, and 3040. The first array 3010 may be a continuous series of bond sites 3002 which enclose the second array 3020, the third array 3030, and the fourth array 3040. As shown, the second array 3020 may be discontinuous and disposed between the first array 3010 and the third array 3030. The third array 3030, much like the first array 3010 may be continuous and may enclosed the fourth array 3040. The fourth array 3040 may be discontinuous and be disposed in a target area on the absorbent article. The target area signifies the location of the article which is likely to receive the fluid insult from the wearer assuming the absorbent product is donned properly.

With the discontinuous fourth array 3040, fluid insults can be provided with adequate access to the nonwoven laminate. Additionally, with the continuous third array 3030, fluid insults are encouraged to stay within the target area as opposed to meandering to outer edges of the article.

Figure 67:
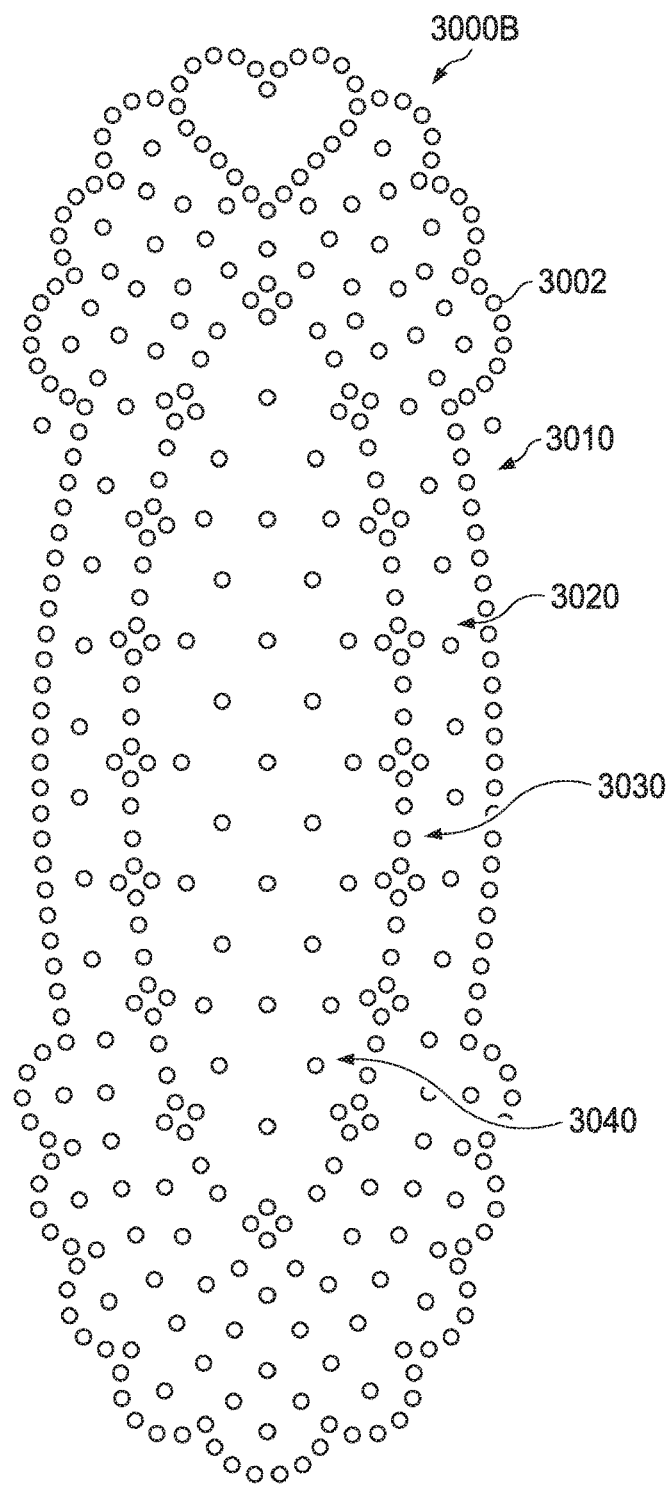

As shown in FIG. 67, the bond pattern 3000B may comprise a plurality of arrays of bond sites. For example, a first array 3010B may be continuous and comprise bond sites which are arranged in the shape of hearts, clouds, etc. A second array 3020B is disposed within the first array 3010B and disposed about a third array 3030B. The third array 3030B is continuous and surrounds the fourth array 3040B. Much like the arrays of the bond pattern 3000A, the arrays of the bond pattern 3000B can provide fluid handling benefits.

Figure 68:
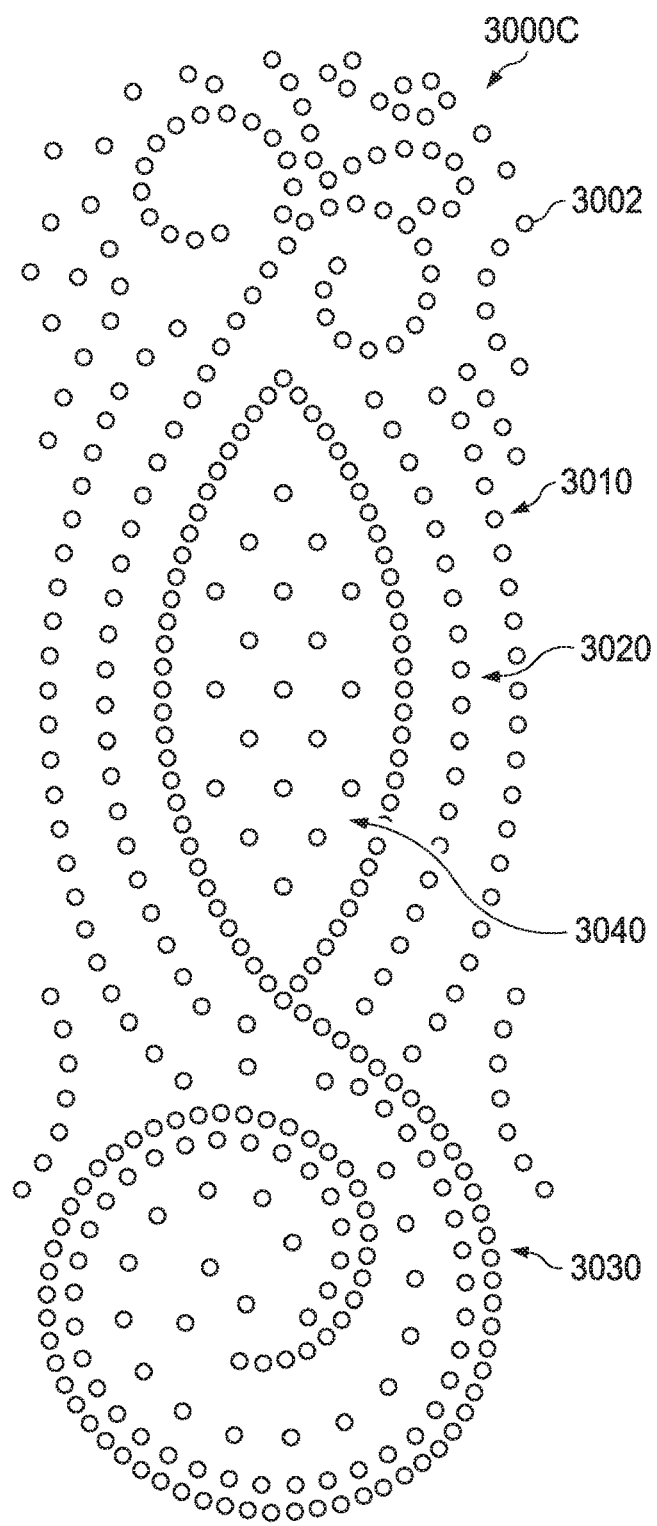

As shown in FIG. 68, a bond pattern 3000C may comprise a plurality of arrays of bond sites. However, in contrast with the previous bond patterns, a first array 3010C may be discontinuous about the entire periphery of a pad. As shown, the first array 3010C comprises a plurality of continuous segments of bond sites each of which is disconnected from one another. A second array 3020C may be disposed inboard of the first plurality 3010C and may also comprise a plurality of continuous segments which are discontinuous. A third array 3030C may comprise continuous bond sites and enclose a fourth array 3040C. The fourth array 3040C comprises a plurality of discontinuous bond sites. Much like the bond patterns discussed previously, the bond pattern 3000C may provide fluid handling benefits.

Figure 69:
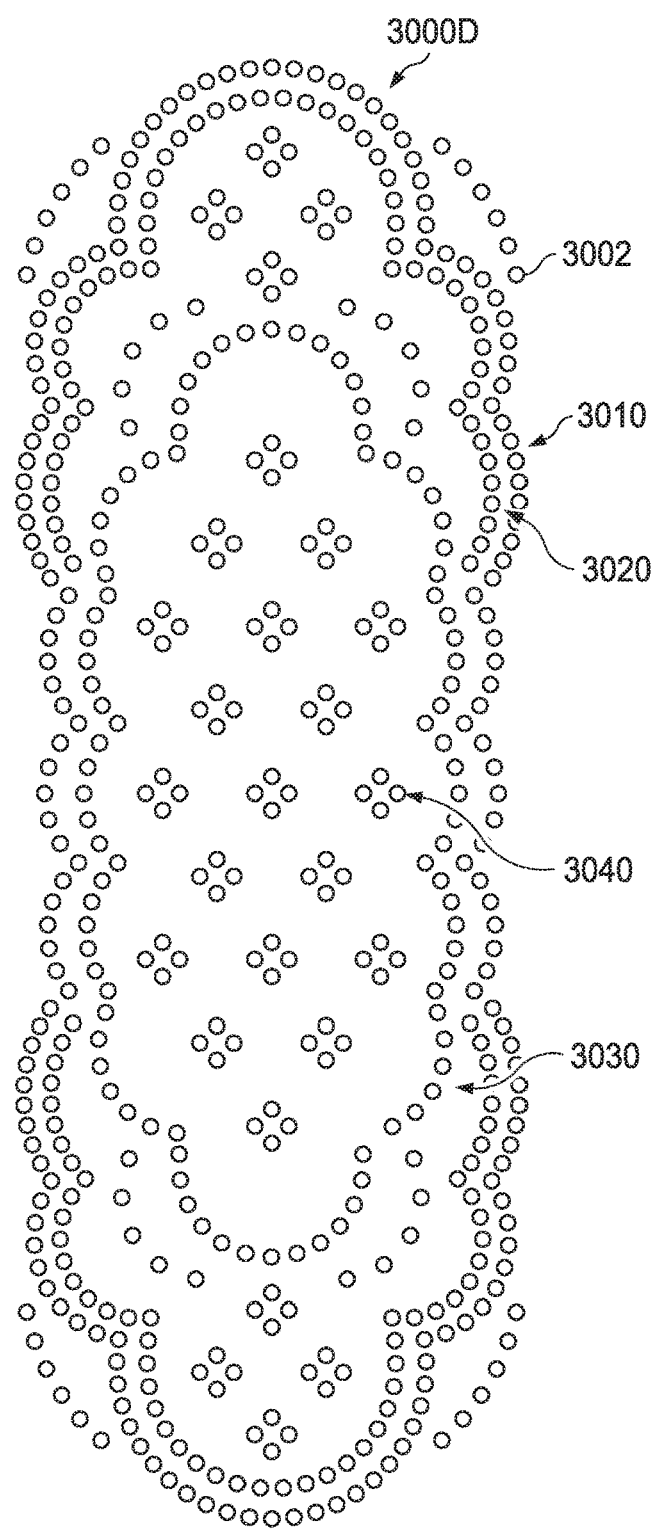

As shown in FIG. 69, a bond pattern 3000D may comprise a plurality of arrays of bond sites. For example, a first array 3010D may comprise a plurality of bond sites which are arranged in a continuous fashion and may enclosed a second array 3020D, a third array 3030D and a fourth array 3040D of bond sites. The second array 3020D may comprise a plurality of bond sites which form continuous elements as well as a plurality of bond sites which form discontinuous elements. These continuous elements may be disposed at a first end and second end of the absorbent article. The third array 3030D of plurality of bond sites may be continuous and may enclosed the fourth array 3040D. The fourth array 3040D may comprise a plurality of bond sites which form a plurality of elements. Each of the elements may be continuous but discontinuous with respect to the other elements. For example, each element may comprise a plurality of bond sites, e.g. 4. The bond sites would be considered continuous for each respective element, but the bond sites from element to element would be discontinuous.

Color

Any of the layers of the apertured webs may have a color that is the same or different than another layer of the apertured web, regardless of whether a layer is apertured or non-apertured. For instance, in a two layer apertured web, a first layer may be blue and a second layer may be white, or a first layer may be dark blue and the second layer may be light blue. There may be a Delta E difference between at least some of the layers. The layers may also have the same opacity or a different, as described in further detail below.

Figure 9:
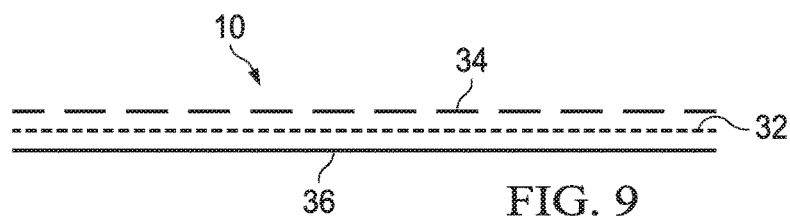
FIG. 9 is a schematic representation of a cross-sectional view of a apertured web having two layers, with a first apertured layer and a second non-apertured layer and with printing or ink on one of the layers in accordance with the present disclosure.

Either in addition to or in lieu of the various layers being colored, referring to FIG. 9, one or more of the layers of the apertured webs 10 of the present disclosure may include printing 32, e.g., with ink or a pigmented or colored pattern. The ink may be deposited via any printing process known in the art including, but not limited to, flexographic printing and digital inkjet printing. The printing may comprise a pattern or a plurality of patterns which form graphics and/or other depictions, hereafter, "printed indicia." The printing may be on an external surface of a first layer 34 of the apertured web 10, between the first and second layers 34, 36 (as illustrated) of the apertured web 10, or may be on a surface beneath the second layer 36 of the apertured web 10. The printing may also be situated in any suitable location if the apertured web has more than two layers (e.g., on the surface of any of the layers). The printing may also be deposited in zones of the apertured web and/or in patterns throughout the apertured web. The printing may be different or the same in different zones of the apertured web. If the printing will be covered by one of the layers (e.g., layer 34), the covering layer (e.g., layer 34) may have a relatively low opacity to enhance the visual appearance of the printing. The density of the printing (e.g., clarity and contrast) may be enhanced by including small-denier fibers in the printed layer including, but not limited to, melt-blown fibers, microfibers, and nanofibers. The printing 32 may be on the first layer 34, the second layer 36, and/or may be on a separate layer positioned at least partially intermediate the first and second layers 34 and 36. In an instance, the printing may indicate the proper orientation of an absorbent article on a wearer (e.g., front/rear). It will be understood that printing may be used with any of the various forms and configurations of the apertured webs disclosed herein. In some forms, more than one type or color, for example, of printing may be used in a single apertured web. Additional layers may also be provided in a pattered apertured web having one or more printed patterns. For those forms of the present invention comprising a single layer apertured web, the apertured web may comprise printing and/or be pigments as described herein.

Figure 10:
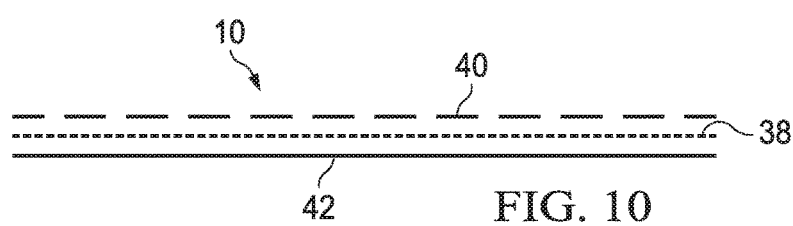
FIG. 10 is a schematic representation of a cross-sectional view of a apertured web having two layers, with a first apertured layer and a second non-apertured layer and with a colored adhesive on one of the layers or positioned intermediate the layers in accordance with the present disclosure.

Either in addition to or in lieu of the various layers being colored and/or having printing, referring to FIG. 10, the apertured webs may comprise a colored adhesive 38 or other colored substance (hereinafter "colored adhesive"). The colored adhesive 38 may include a pigment, a tint, or a dye, for example. The colored adhesive, in a form, may be positioned between a first layer 40 and second layer 42 of an apertured web 10. In some forms, more than one colored adhesive may be used in a single apertured web. The colored adhesive may also be situated in any suitable location if the apertured web has more than two layers (e.g., on the surface of or intermediate any of the layers). The colored adhesive may also be deposited in zones of the apertured web and/or in patterns throughout the apertured web. The colored adhesive may be different or the same in different zones of the apertured web. The colored adhesive may be positioned intermediate the two layers 40, 42 or positioned on any other surfaces of the layers 40, 42. Additional layers may also be provided in a apertured web having one or more colored adhesives. As stated previously, adhesive and particularly colored adhesive may be applied such that the adhesive forms a pattern or a plurality of patterns which form graphics and/or other depictions, referred to as "adhesive indicia." Adhesive indicia are discussed in additional detail hereafter.

In an instance, a colored adhesive may be positioned between two low basis weight materials (e.g., 15 gsm or less, 10 gsm or less) forming an apertured web, so that the colored adhesive may be visible from either side of the apertured web. In a laminate topsheet context, this can provide a high basis weight topsheet to achieve improved softness, while still retaining the benefit of seeing the colored adhesive from either side of the apertured web.

In some forms of the present invention, adhesive indicia may be created from non-colored adhesive. In some forms of the present invention, the provision of clear adhesive can change the appearance of the apertured web. For example, in such forms, the provision of clear adhesive can make the web appear more opaque and/or more dense in the area of adhesive application. As such, the provision of adhesive—whether colored or non-colored (clear)—can form adhesive indicia. As an example, a disposable absorbent article of the present invention may comprise adhesive indicia which comprises a plurality of discrete adhesive bond sites which may comprise a combination of non-colored (clear) adhesive and/or colored adhesive.

Structures

Figure 38A:
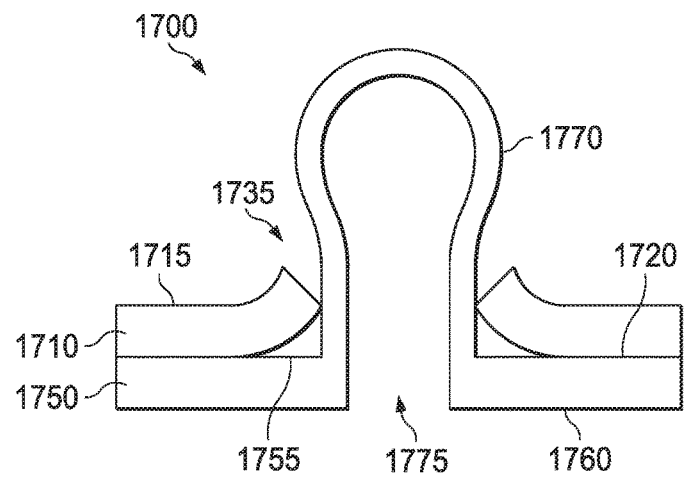
FIGS. 38A-38B illustrate schematic illustrations of examples of apertured webs of the present disclosure, with structures formed thereon.

Apertured webs described herein may additionally comprise an array of structures. For example, a first portion of the apertured web may comprise an array of apertures as described herein while a second portion comprises an array of structures. The structures may be those shown in FIGS. 38A-38B. For example, as shown in FIG. 38A, an apertured web 1700 of the present invention may comprise a looped nonwoven tuft 1770 or any array thereof. As shown, the apertured web 1700 comprises a first nonwoven layer 1710 and a second nonwoven layer 1750. The first nonwoven layer 1710 comprises a generally planar first surface 1715 and a generally planar second surface 1720 opposed to the first surface 1715, and the second nonwoven layer 1750 has a generally planar first surface 1755 and a generally planar second surface 1760. The first nonwoven layer 1710 comprises a first plurality of substantially randomly oriented fibers, and the second nonwoven layer 1750 comprises a second plurality of substantially randomly oriented fibers. At least a portion of the second plurality of fibers in the second nonwoven layer 1750 is in liquid communication with the first nonwoven layer 710. The respective surfaces of the first nonwoven layer 1710 and second nonwoven layer 1750, can be arranged such that the first surfaces 1715 and 1755, respectively, are body-facing surfaces, and the second surfaces 1720 and 1760, respectively, can be arranged as garment-facing surfaces.

As shown in FIG. 38A, the second surface 1720 of the first nonwoven layer 1710 may comprise a first discontinuity 1735. The first discontinuity 1735 may be formed when localized areas of constituent fibers of the first nonwoven layer 1710 are urged in the Z-direction such that these constituent fibers are disposed superjacent to the first surface 1715 of the first nonwoven layer 1710. The urging in the Z-direction of the constituent fibers of the first nonwoven layer 1710 may be such that a plurality of fibers break thereby forming the first discontinuity 1735.

As shown, the second surface 1760 of the second nonwoven layer 1750 may comprise a second discontinuity 1775. With regard to the second discontinuity 1775, localized areas of constituent fibers of the second nonwoven layer 750 are urged in the Z-direction such that these constituent fibers are disposed superjacent to a plane of the first surface 1755 of the second nonwoven layer 1750. This Z-direction urging also forces these constituent fibers to extend through the first of discontinuity 1735 in the second surface 1720 of the first nonwoven layer 1710. The extension of the constituent fibers of the second nonwoven layer 1750 forms a tufts 1770.

Figure 38B:
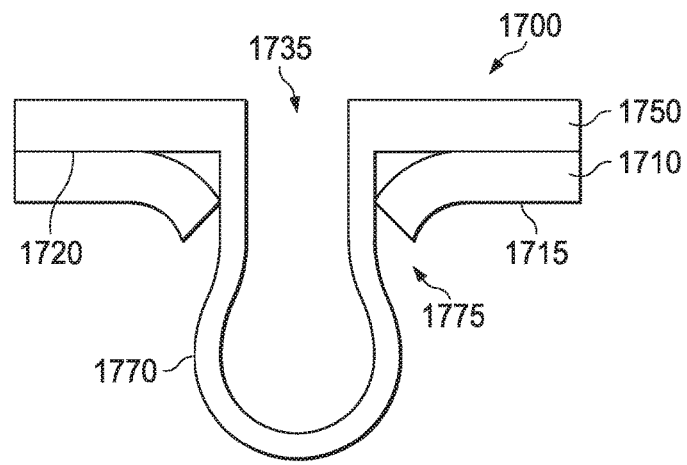
Figure 39:
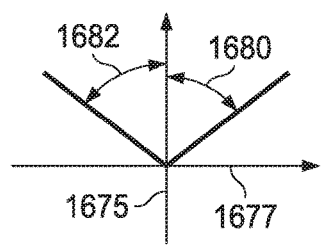
FIG. 39 is a depiction of a coordinate system for the apertured webs of the present invention.
Figure 40:
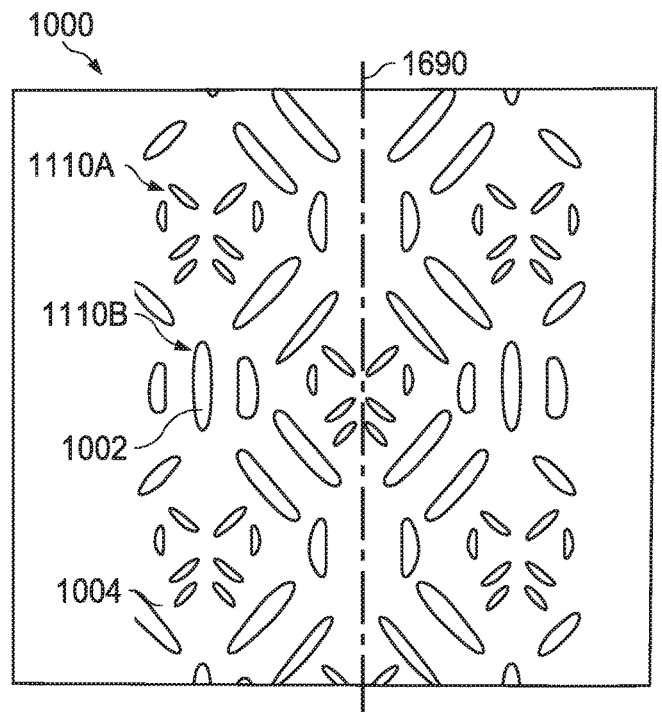
FIGS. 40-53 are photographs of apertured webs constructed in accordance with the present invention.
Figure 41:
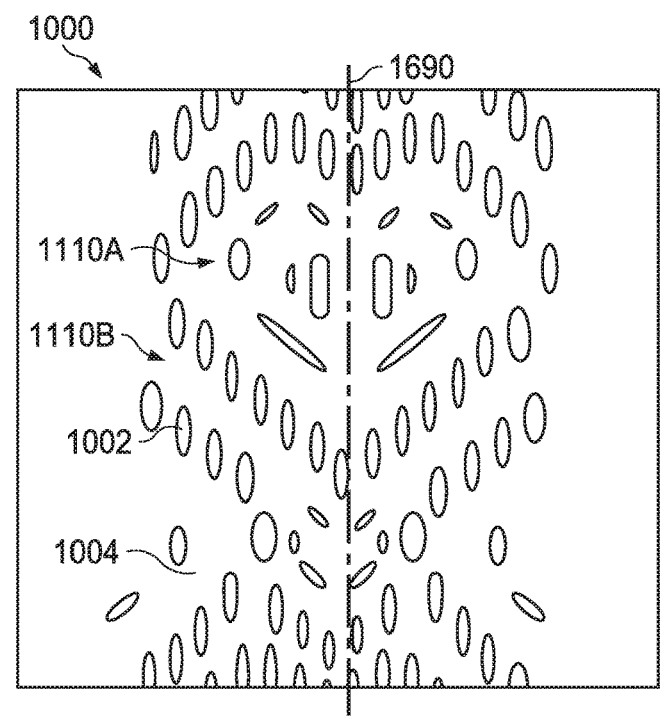
Figure 42:
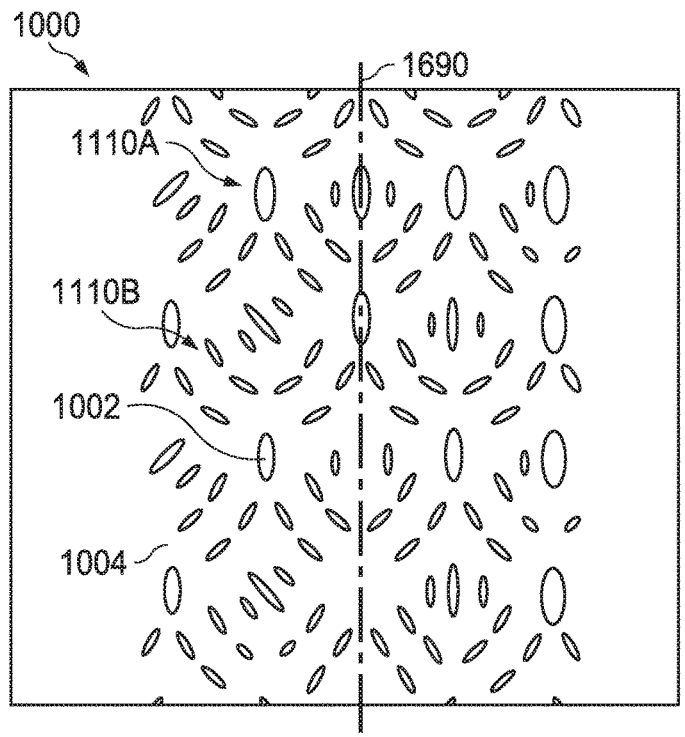
Figure 43:
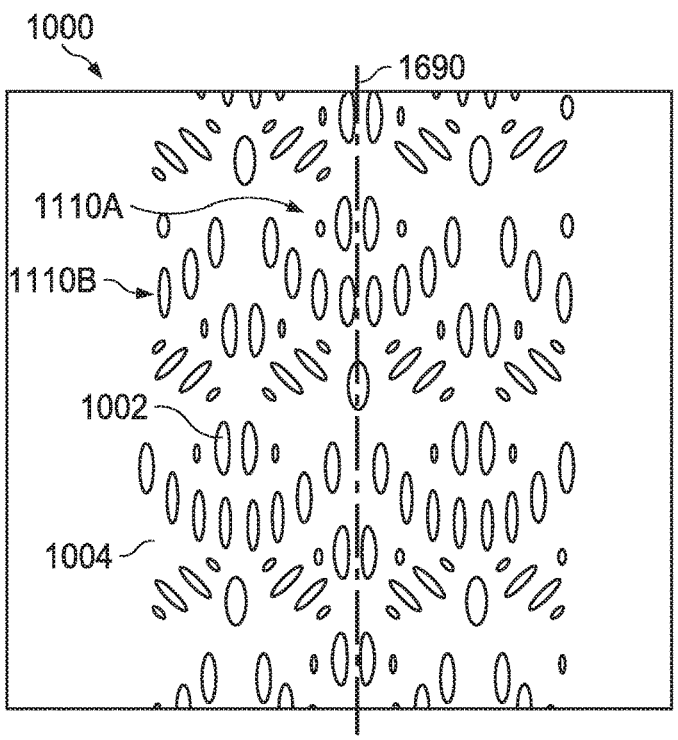
Figure 44:
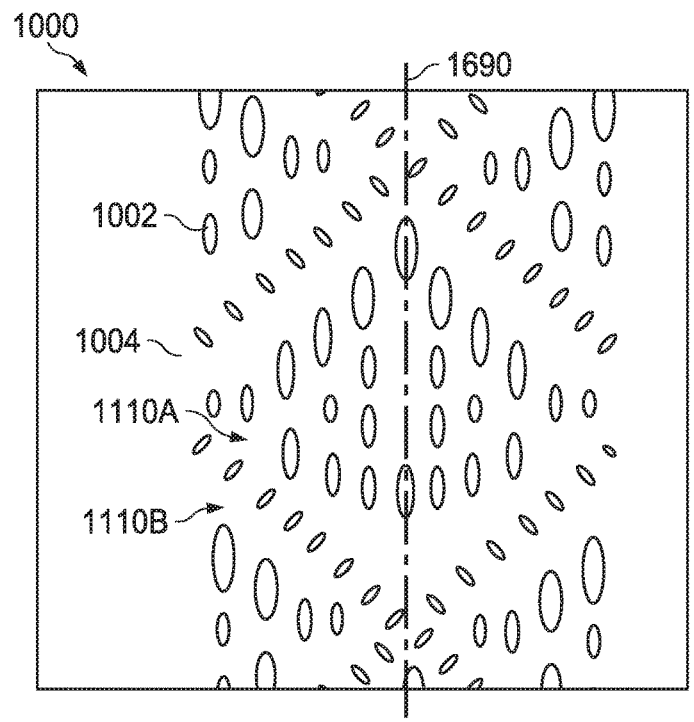
Figure 45:
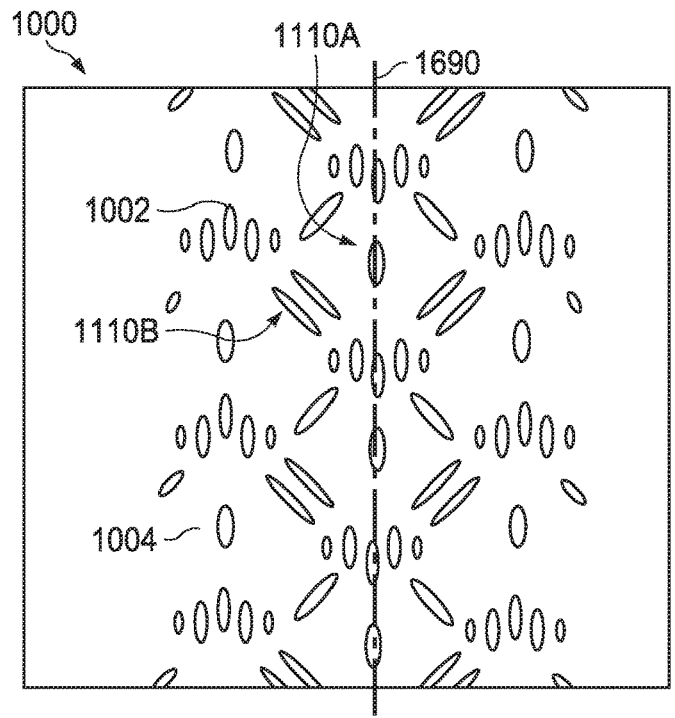
Figure 46:
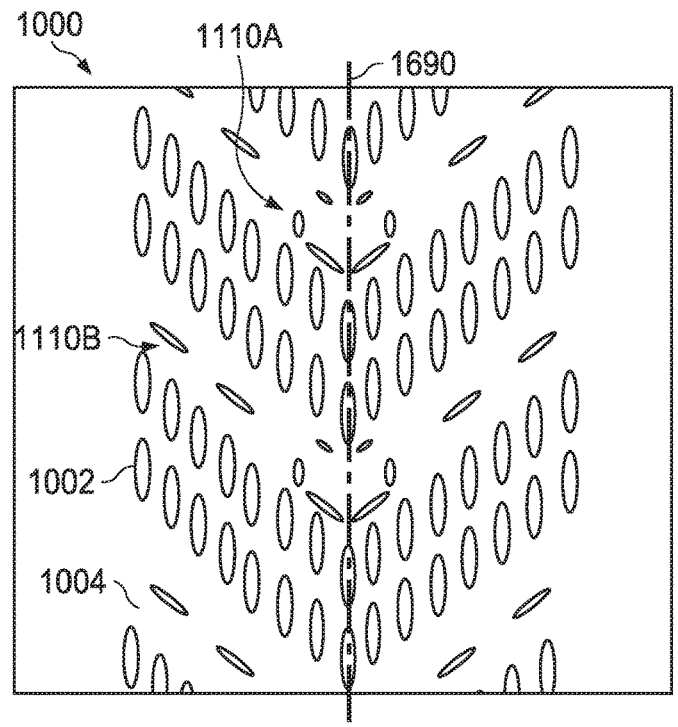
Figure 47:
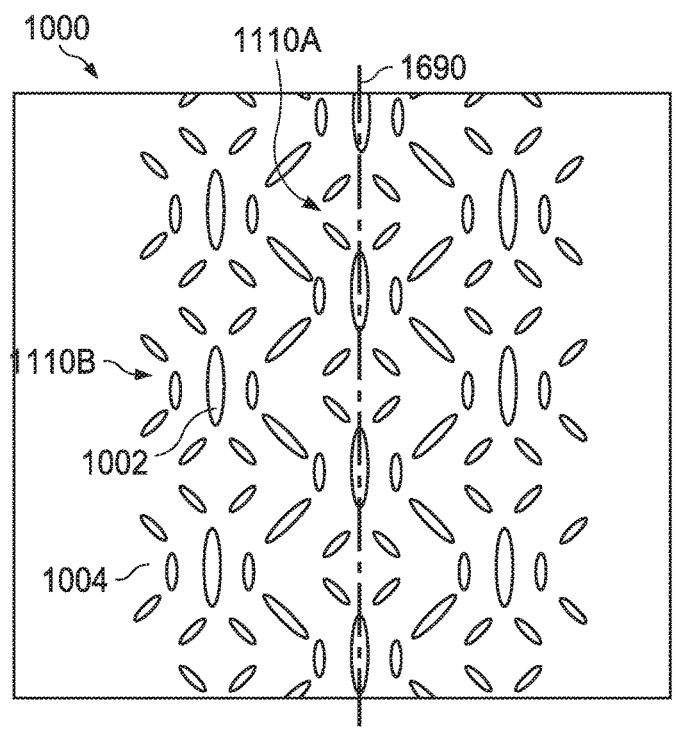
Figure 48:
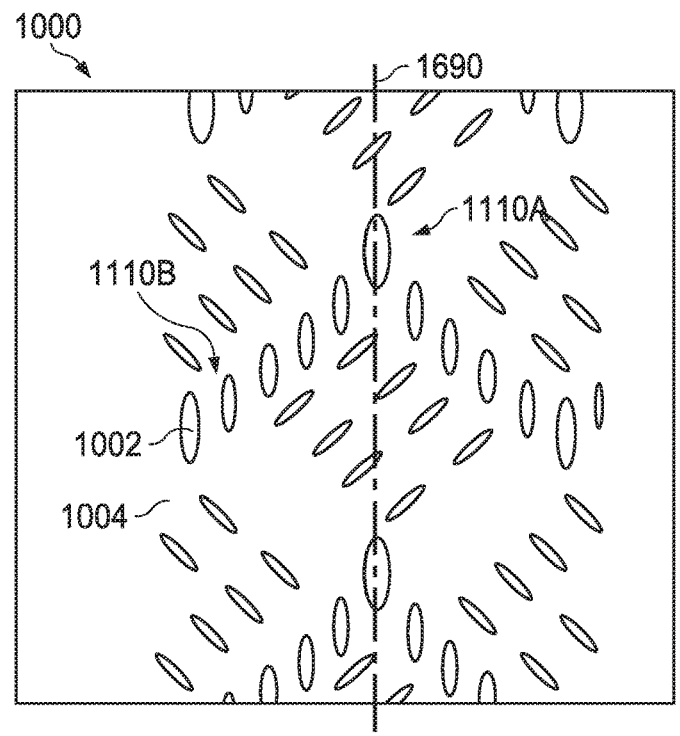
Figure 49:
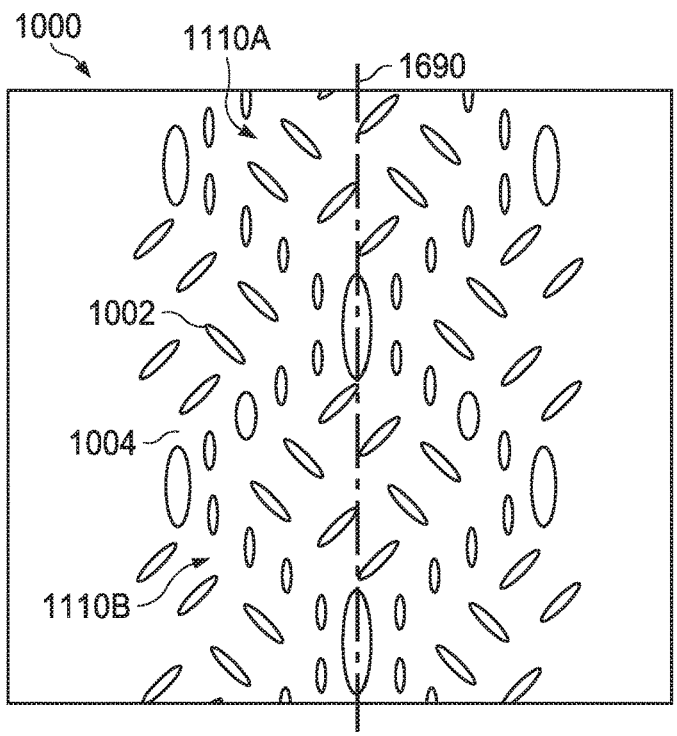
Figure 50:
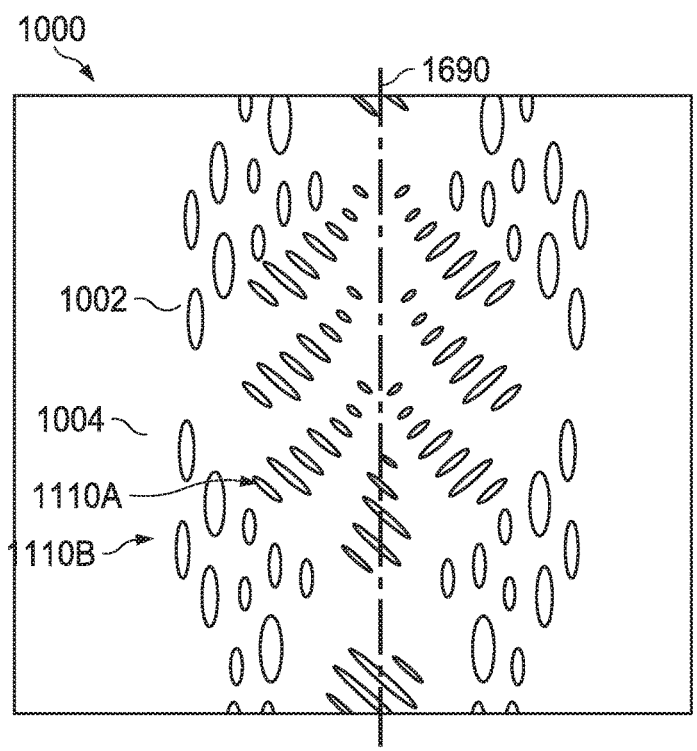
Figure 51:
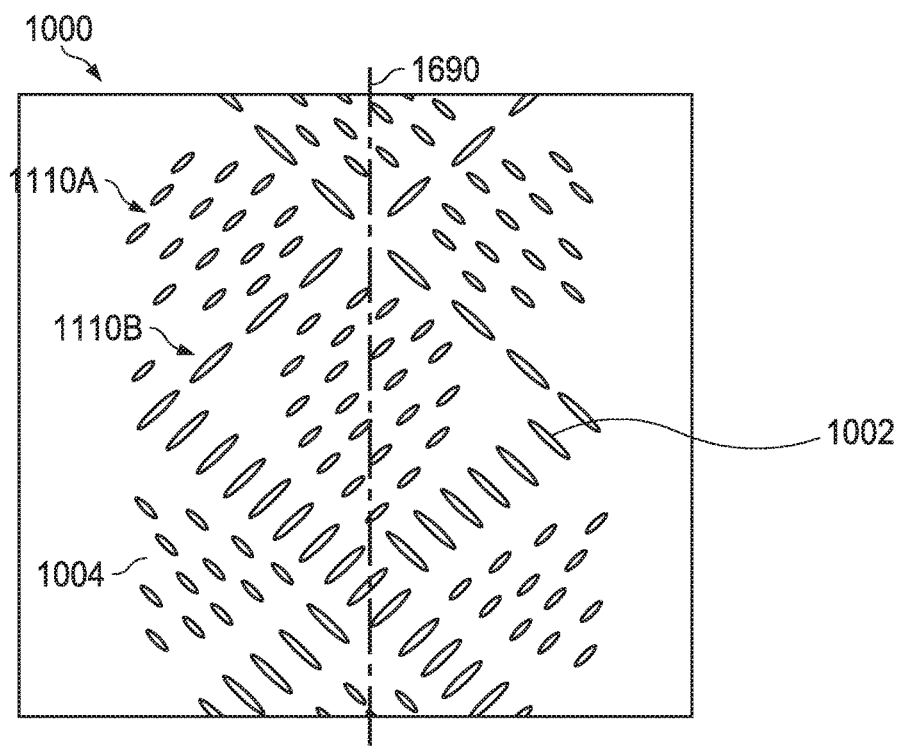
Figure 52:
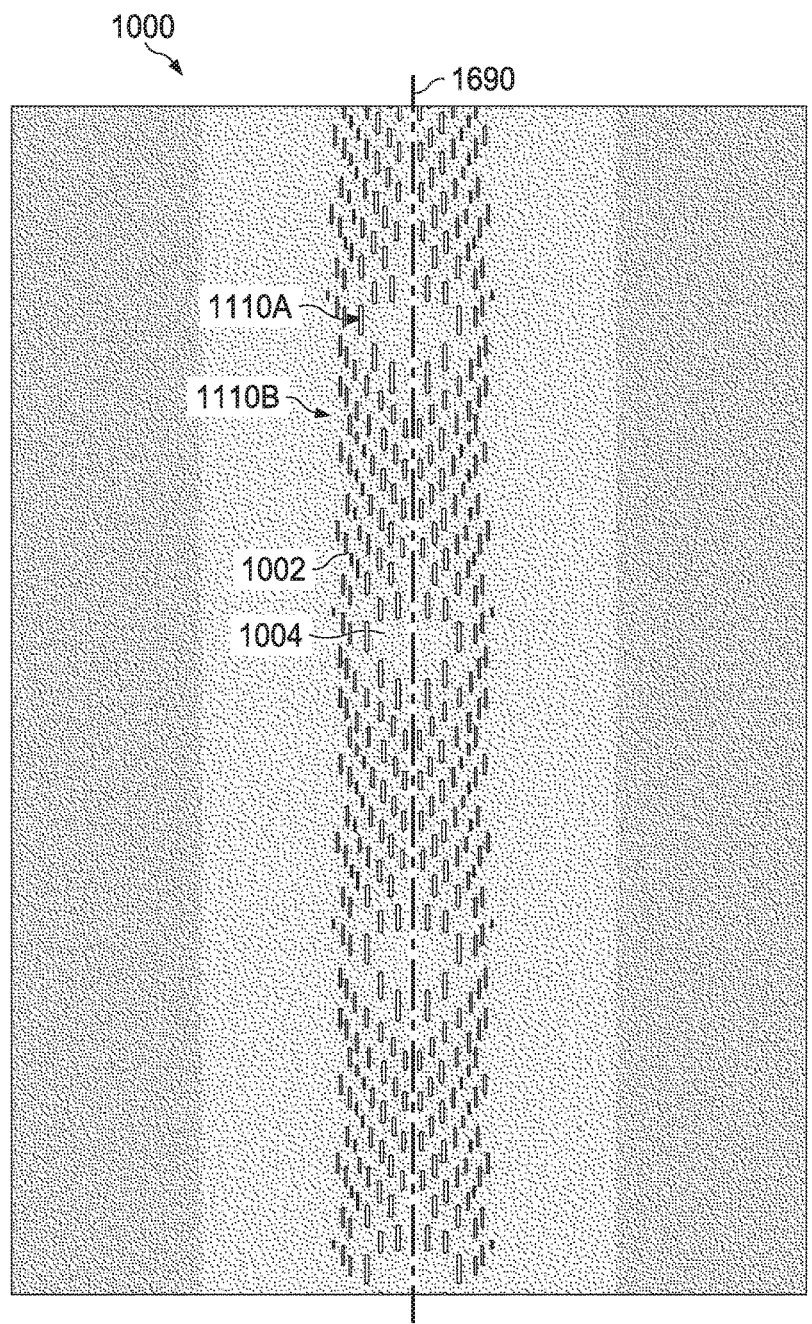
Figure 53:
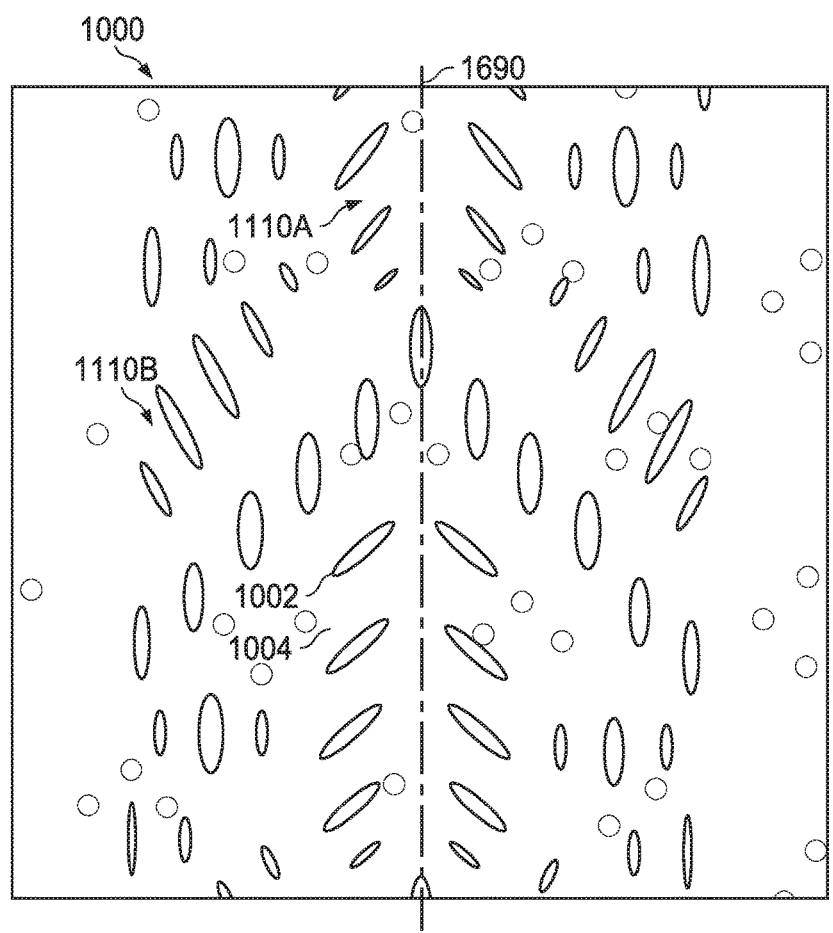

With regard to FIG. 38B, the nonwoven web 1700 may be configured as shown. Namely, as shown, the first surface 1715 of the first nonwoven layer 1710 may comprise the first discontinuity 1735. The first discontinuity 1735 in the embodiment shown in FIG. 38B, is formed when localized areas of constituent fibers of the first nonwoven layer 1710 are urged in the negative Z-direction such that these constituent fibers are disposed subjacent to the first surface 1715 of the first nonwoven layer 1710 thereby forming the tuft 1770. In some embodiments, the tuft 1770 may extend beyond the second surface 1760 of the second nonwoven layer 1750 such that at least a portion of the tuft 1770 is subjacent to the second surface 1760.

As shown, in some embodiments, the tuft 1770 may extend through the second discontinuity 1775. The second discontinuity 1775 may be created when localized areas of constituent fibers of the second nonwoven layer 1750 are urged in the negative Z-direction such that these constituent fibers are disposed subjacent to the first surface 1755 of the second nonwoven layer 1750. The urging in the negative Z-direction of the constituent fibers of the second nonwoven layer 1750 may be such that a plurality of fibers break thereby forming the second discontinuity 1775.

Tufts 1770 can comprise a plurality of looped fibers that are substantially aligned such that each of the tufts 1770 have a distinct linear orientation and a longitudinal axis L. By "looped" fibers it is meant to refer to fibers of the tufts 1770 that are integral with and begin and end in the second layer 1750 but extend generally outwardly in the Z-direction from the first surface 1755 of the second layer 1750 and extend beyond the first surface 1715 of the first layer 1710. Similar orientations are contemplated for the tufts 1770 formed by the first layer 1710.

The tufts 1770 described herein may have longitudinal axes generally aligned in the MD. However, tufts 1770 and, therefore, longitudinal axes L, can, in principle, be aligned in any orientation with respect to the MD or CD. Therefore, in general, it can be said that for each tuft 1770, the looped aligned fibers are aligned generally orthogonal to the longitudinal axis L such that they have a significant vector component parallel to transverse axis and can have a major vector component parallel to the transverse axis.

As described below, another characteristic of tufts 1770 can be their generally open structure characterized by open void area defined interiorly of tufts 1770. The void area may have a shape that is wider or larger at a distal portion of the tuft 1770 and narrower at the tuft base of the tuft 270. This is opposite to the shape of the tooth which is used to form the tuft 270 which is discussed hereafter. The term "void area" is not meant to refer to an area completely free of any fibers. Rather, the term is meant as a general description of the general appearance of tufts 1770.

These structures described with regard to FIGS. 38A-38B are similarly applicable to those apertured webs which comprise a plurality of substrates in addition to those apertured webs which comprise a plurality of layers.

The structures disclosed herein may be provided in arrays or a plurality thereof. Such arrays of structures or plurality of arrays of structures may comprise a pattern or a plurality of patterns which form graphics and/or other depictions, hereafter, "structural indicia." Additional forms are contemplated where the structures described herein may be utilized in any combination.

The structures described herein can aid in fluid management as well as provide a comfortable feel to the user. For example, those structures, e.g. tufts 1770 oriented in the Z-direction can provide a user with a soft feel. As another example, those structures, e.g. tufts 1770 oriented in the negative Z-direction can provide fluid management benefits.

Forms of the present invention are contemplated, where the constituent material of either the first layer or second layer does not break upon the Z-direction urging mentioned heretofore. In such forms, inner tufts 1770 and outer tufts may be created. Some examples of suitable structures and their method of manufacture are described in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226.

Other suitable structures can include ridges/grooves. Such structures and processes for producing ridges and/or grooves are disclosed in U.S. Pat. Nos. 6,458,447; 7,270,861; 8,502,013; 7,954,213; 7,625,363; 8,450,557; and 7,741,235. Additional suitable processes and structures are described in US Patent Application Publication Nos. US2003/018741; US2009/0240222; US2012/0045620; US20120141742; US20120196091; US20120321839; US2013/0022784; US2013/0017370; US2013/013732; US2013/0165883; US2013/0158497; US2013/0280481; US2013/0184665; US2013/0178815; and US2013/0230236700. Still additional suitable processes and structures are described with regard to PCT Patent Application Publication Nos. WO2008/156075; WO2010/055699; WO2011/125893; WO2012/137553; WO2013/018846; WO2013/047890; and WO2013/157365.

Other suitable structures include nubs. Some suitable processes for creating nubs on a web and the resulting structures are described in U.S. Pat. Nos. 7,713,683; 6,852,475; 7,303,861; 8,057,729; 8,287,800; and U.S. Patent Application Publication No. 2004/0121120.

Additional structures include embossing. Embossing of absorbent articles generally results in thinned out areas in the absorbent article. Embossing, similar to fusion bonding, involves the manipulation of material in a first layer and a second layer in the positive and/or negative Z-direction. Generally, embossing does not result in the fusion of layers. Unlike fusion bonds, embossing typically results in macro depressions in an absorbent article. Embossing is further discussed in U.S. Pat. Nos. 8,496,775 and 8,491,742.

Opacity

The opacity of at least one of the layers of an apertured web may differ from the opacity of the other layers of the apertured web. In some instances, the layer of the apertured web closest to an external observer may have a lower opacity than an underlying layer in order to maximize observable contrast differences between the layers and/or to observe printing or colored adhesives. Alternatively, the layer of the apertured web closest to an external observer may have a higher opacity than an underlying layer in order to more effectively mask bodily exudates (e.g., urine, menses, or BM) or to provide for greater color contrast with the layers below. When an apertured web is used as a fluid-permeable topsheet, the layer closest to an external observer would be the wearer-facing surface. In a form, where the apertured web is located on the external surface of an absorbent article (e.g., an outer cover, fastening system element, stretch ear, belt, or side panel), the layer closest to an external observer would be the garment-facing surface. For example, the opacity of a non-apertured layer may be lower than that of an apertured layer, or vice versa, depending on the specific orientation of an apertured web in an absorbent article.

An apertured web may have a high opacity. This enables an aperture pattern to be more easily distinguished, provides contrast to any colors and materials underneath, and in the case of a diaper topsheet or a sanitary napkin topsheet, masks the presence of bodily fluids contained within the absorbent core, providing a cleaner appearance to the wearer. To achieve this benefit, opacities of about 30, about 40, about 50, or about 60 may be desired. In some forms of the present invention, opacities may range from about 40-100 or from about 50-90, specifically reciting all values within these ranges and any ranges created thereby.

Increases in opacity can be achieved via any known suitable product/process. Some suitable examples include adding fillers (e.g. TiO2), fiber shape (e.g. Trilobal vs. round), smaller fiber diameters (including microfibers and/or nano fibers), etc. A specific example of nonwoven web having high opacity is an SMS (spunbond, meltblown, spunbond) or an SMNS (spunbond, meltblown, nano fiber, spunbond) construction. Another specific example is a nonwoven comprising nano fibers, such as those produced by melt film fibrillation as described in U.S. Pat. No. 8,487,156 and U.S. Patent Application Publication No. 2004/0266300. In one specific example, the web of the invention may comprise a layer having meltblown and nanofibers—SMNS construction.

Components of Absorbent Articles

The apertured webs of the present disclosure may be used as components of absorbent articles. More than one apertured web may be used in a single absorbent article. In such a context, the apertured webs may form at least a portion of:

a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) of the apertured web forms the backsheet and a nonwoven material forms the outer cover; a leg cuff; an ear or side panel; a fastener; a waist band; or any other suitable portion of an absorbent article. The apertured webs may take on different configurations and patterns of land and aperture areas depending on their particular use in an absorbent article. The number of layers in a apertured web may also be determined by the apertured webs' particular use.

As referenced above, any of the apertured webs of the present disclosure may be disposed on an external surface of the absorbent article (i.e., the outer cover or garment facing-surface). In such an instance, the aperture arrays, patterns, or properties of the same may be the same or different in different regions of the external surface. In one outer cover form, effective aperture areas and effective open areas may be higher in a waist region than in a crotch region of the outer cover for better breathability. In another outer cover form, the waist regions may include aperture arrays, while the crotch region comprises more uniform aperture patterns. In each of these forms, the effective aperture area and effective open area, or apertures arrays may provide higher air porosity in the waist region than in the crotch region, allowing more sweat evaporation and better breathability in the tightly occluded waist area Feminine Hygiene Products The apertured webs may also be used as components of absorbent articles, such as feminine hygiene products, including sanitary napkins, liners, and tampons. More than one apertured web may be used in a single feminine hygiene product. In a sanitary napkin context, the apertured webs may form at least a portion of: a topsheet; a topsheet and an acquisition layer; a topsheet and a distribution layer; a topsheet and a secondary topsheet; a backsheet; an outer cover; an outer cover and a backsheet; wings; wings and a topsheet or a backsheet; a covering for a tampon; or any other suitable portion of a feminine hygiene product. The apertured webs may take on different configurations and patterns of land and aperture areas depending on their particular use in a feminine hygiene product. The number of layers in an apertured web may also be determined by the apertured webs' particular use. The use of the apertured web in a feminine hygiene article is further disclosed with regard to FIG. 33.

Other Consumer Products

The apertured webs may also be used as components of absorbent articles, such as cleaning substrates, dusting substrates, and/or wipes. More than one apertured web may be used in a single cleaning or dusting substrate and/or a single wipe. The apertured webs may take on different configurations and patterns of land and aperture areas depending on their particular use in a cleaning substrate, dusting substrate, and/or a wipe. The number of layers in a apertured web may also be determined by the apertured webs' particular use.

Physical Characteristics

The apertured webs of the present disclosure may take on different physical characteristics depending on their intended or desired use in absorbent articles, feminine hygiene products, cleaning substrates, dusting substrates, wipes, or other consumer products. For instance, the properties of density, basis weight, aperture pattern, land area pattern, caliper, opacity, three-dimensionality, and/or elasticity, for example, may be varied depending on the desired use of the apertured web. More than one apertured web may be combined with other, similar or different, apertured webs in some instances for certain design criteria.

Method of Making

The apertured webs of the present disclosure may be made generally by using the process generally described in U.S. Pat. No. 5,628,097 entitled "Method for Selectively Aperturing a Nonwoven Web" which issued May 13, 1997 and U.S. Patent Publication 2003/0021951 entitled "High Elongation Apertured Nonwoven Web and Method of Making" which published Jan. 20, 2003. Additional references include U.S. Pat. Nos. 5,658,639; 5,916,661; and 7,917,985. This process is described in further detail below. Additional processes such as hydroforming carded webs, laser cutting, punching, hot pin, etc. are contemplated. These processes are generally known in the art.

Figure 11:
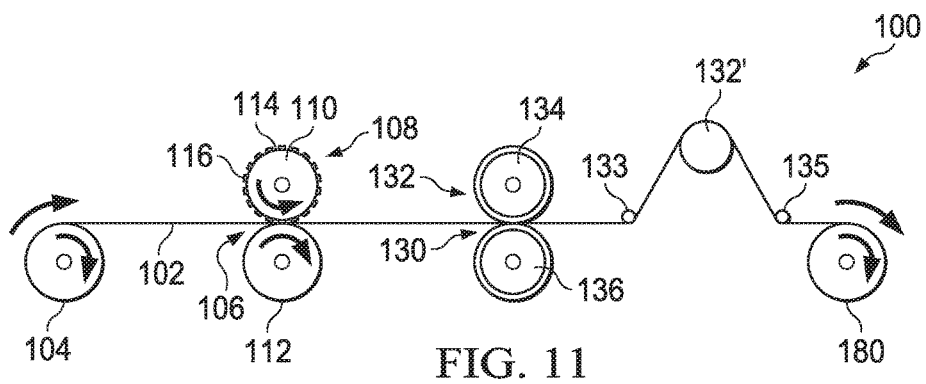
FIG. 11 is a schematic representation of an example process for producing the apertured webs of the present disclosure in accordance with the present disclosure.

Referring to FIG. 11 there is schematically illustrated at 100 one process for forming the apertured webs of the present disclosure. First, a precursor material 102 is supplied as the starting material. The precursor material 102 can be supplied as discrete webs, e.g. sheets, patches, etc. of material for batch processing. For commercial processing, however, the precursor material 102 may be supplied as roll stock, and, as such it can be considered as having a finite width and an infinite length. In this context, the length is measured in the machine direction (MD). Likewise, the width is measured in the cross machine direction (CD).

The precursor material 102 may be one or more nonwoven materials (same or different), one or more films (same or different), a combination of one or more nonwoven materials and one or more films, or any other suitable materials or combinations thereof. The precursor material 102 may be purchased from a supplier and shipped to where the apertured webs are being formed or the precursor material 102 formed at the same location as where the apertured web are being produced.

The precursor material 102 may be extensible, elastic, or nonelastic. Further, the precursor material 102 may be a single layer material or a multilayer material. In an instance, the precursor material 102 may be joined to a polymeric film to form a laminate.

The precursor material 102 may comprise or be made of mono-component, bi-component, multi-constituent blends, or multi-component fibers comprising one or more thermoplastic polymers. In an example, the bi-component fibers of the present disclosure may be formed of a polypropylene core and a polyethylene sheath. Further details regarding bi-component or multi-component fibers and methods of making the same may be found in U.S. Patent Application Publ. No. 2009/0104831, published on Apr. 23, 2009, U.S. Pat. No. 8,226,625, issued on Jul. 24, 2012, U.S. Pat. No. 8,231,595, issued on Jul. 31, 2012, U.S. Pat. No. 8,388,594, issued on Mar. 5, 2013, and U.S. Pat. No. 8,226,626, issued on Jul. 24, 2012. The various fibers may be sheath/core, side-by-side, islands in the sea, or other known configurations of fibers. The fibers may be round, hollow, or shaped, such as trilobal, ribbon, capillary channel fibers (e.g., 4DG). The fibers may comprise microfibers or nanofibers.

The precursor material 102 may be unwound from a supply roll 104 and travel in a direction indicated by the arrow associated therewith as the supply roll 104 rotates in the direction indicated by the arrow associated therewith. The precursor material 102 passes through a nip 106 of a weakening roller (or overbonding) arrangement 108 formed by rollers 110 and 112, thereby forming a weakened precursor material. The weakened precursor material 102 has a pattern of overbonds, or densified and weakened areas, after passing through the nip. At least some of, or all of, these overbonds are used to form apertures in the precursor material 102. Therefore, the overbonds correlate generally to the patterns of apertures created in the precursor material 102.

Figure 12:
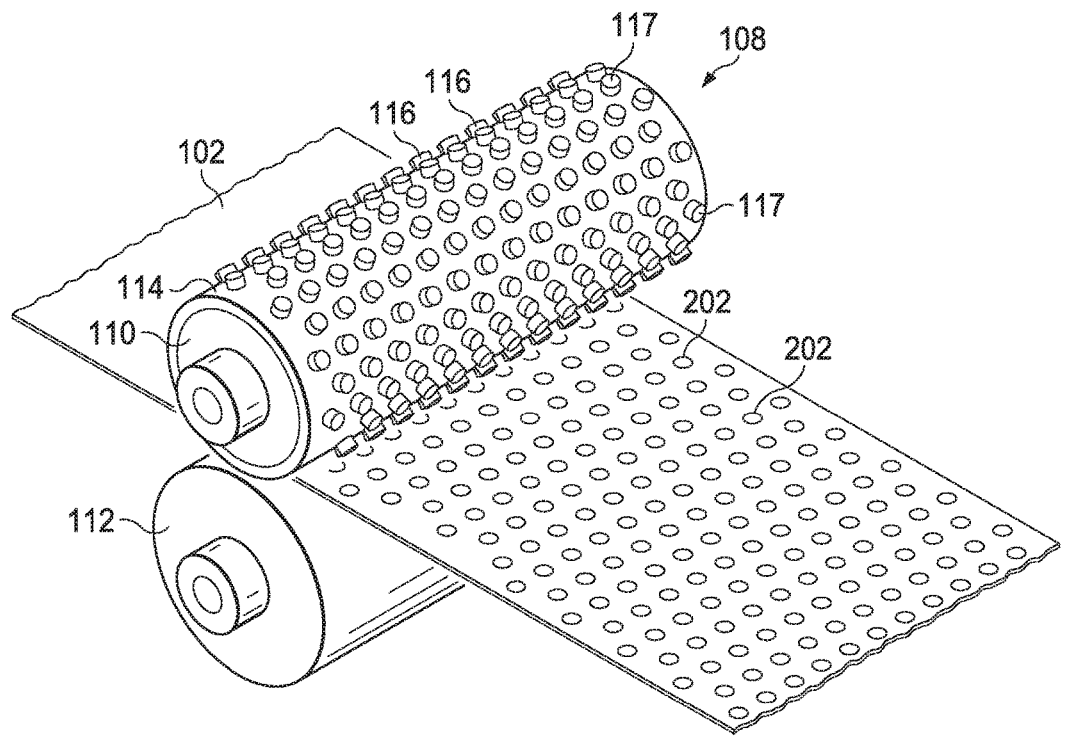
FIG. 12 is a perspective view of a web weakening arrangement of FIG. 11 in accordance with the present disclosure.

Referring to FIG. 12, the precursor material weakening roller arrangement 108 may comprises a patterned calendar roller 110 and a smooth anvil roller 112. One or both of the patterned calendar roller 110 and the smooth anvil roller 112 may be heated and the pressure between the two rollers may be adjusted by known techniques to provide the desired temperature, if any, and pressure to concurrently weaken and melt-stabilize (i.e., overbond) the precursor material 102 at a plurality of locations 202. As will be discussed in further detail below, after the precursor material 102 passes through the weakening roller arrangement 108, the precursor material 102 may be stretched in the CD, or generally in the CD, by a cross directional tensioning force to at least partially, or fully, rupture the plurality of weakened, melt stabilized locations 202, thereby creating a plurality of at least partially formed apertures in the precursor material 102 coincident with the plurality of weakened, melt stabilized locations 202.

The patterned calendar roller 110 is configured to have a cylindrical surface 114, and a plurality of protuberances or pattern elements 116 which extend outwardly from the cylindrical surface 114. The pattern elements 116 are illustrated as a simplified example of a patterned calendar roller 110, but more detailed patterned calendar rollers that can be used to produce apertured webs of the present disclosure will be illustrated in subsequent figures. The protuberances 116 may be disposed in a predetermined pattern with each of the protuberances 116 being configured and disposed to precipitate a weakened, melt-stabilized location in the precursor material 102 to affect a predetermined pattern of weakened, melt-stabilized locations 202 in the precursor material 102. The protuberances 116 may have a one-to-one correspondence to the pattern of melt stabilized locations in the precursor material 102. As shown in FIG. 12, the patterned calendar roller 110 may have a repeating pattern of the protuberances 116 which extend about the entire circumference of surface 114. Alternatively, the protuberances 116 may extend around a portion, or portions of the circumference of the surface 114. Also, a single patterned calendar roller may have a plurality of patterns in various zones (i.e., first zone, first pattern, second zone, second pattern).

Figure 13:
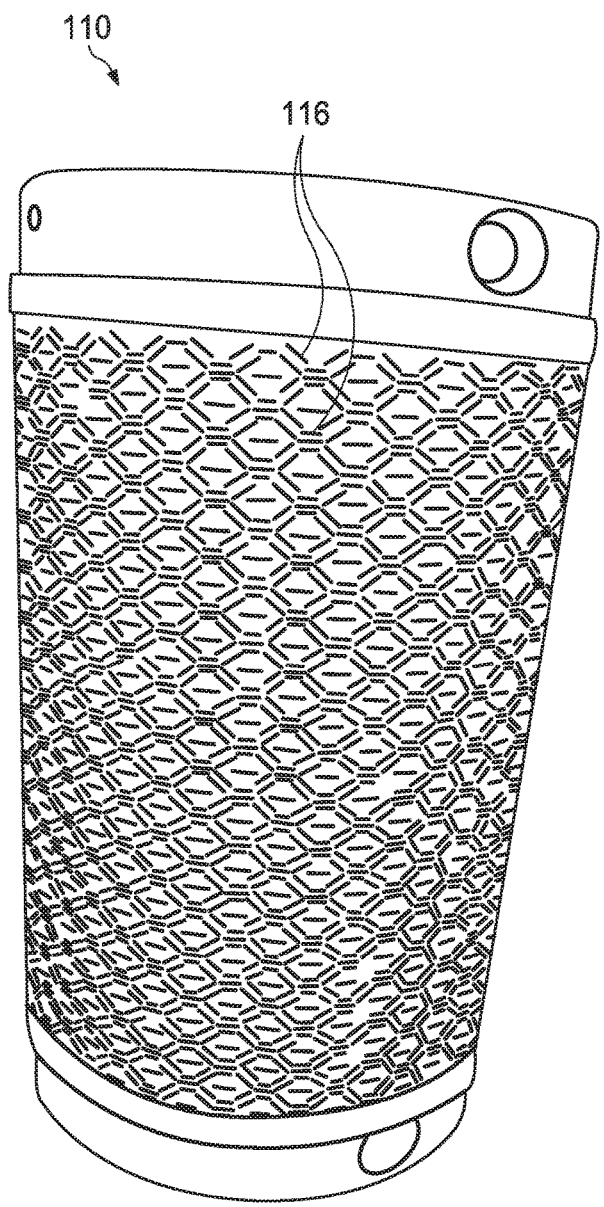
FIG. 13 is a photograph of an exemplary roller that can be used as roller 110 in the weakening arrangement of FIG. 12 in accordance with the present disclosure.
Figure 14:
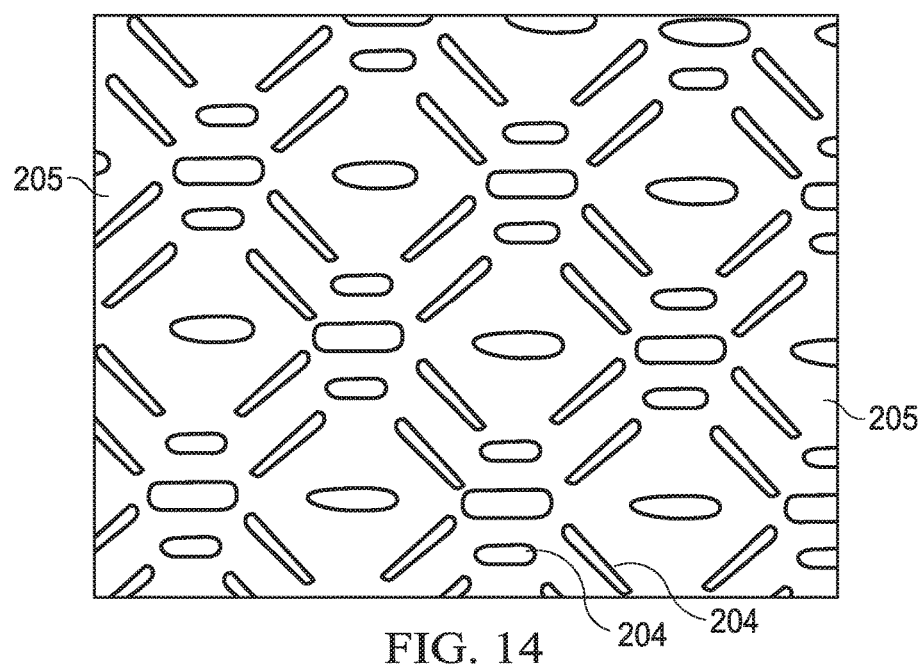
FIG. 14 is a photograph of an example apertured web produced using the roller of FIG. 13 in the weakening arrangement in accordance with the present disclosure.
Figure 15:
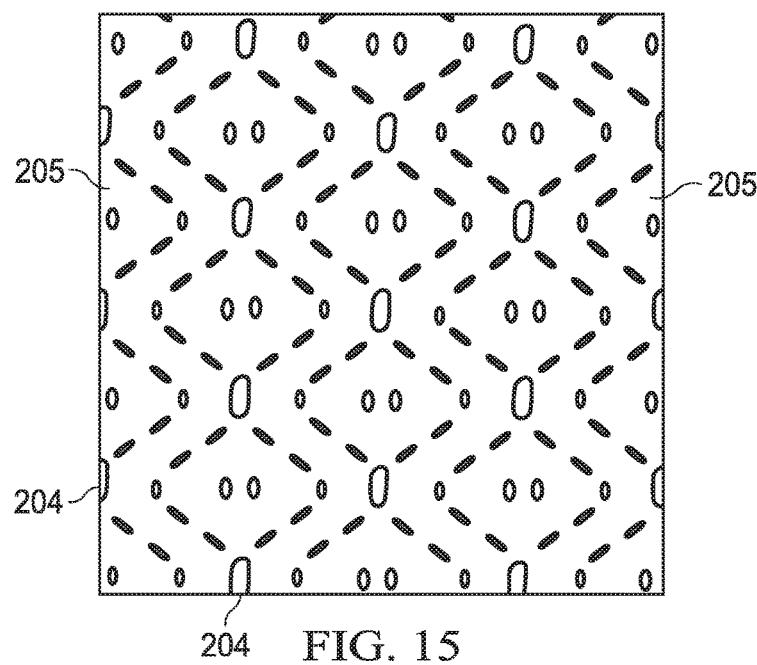
FIG. 15 is a photograph of an example apertured web produced using a weakening arrangement in accordance with the present disclosure.
Figure 16:
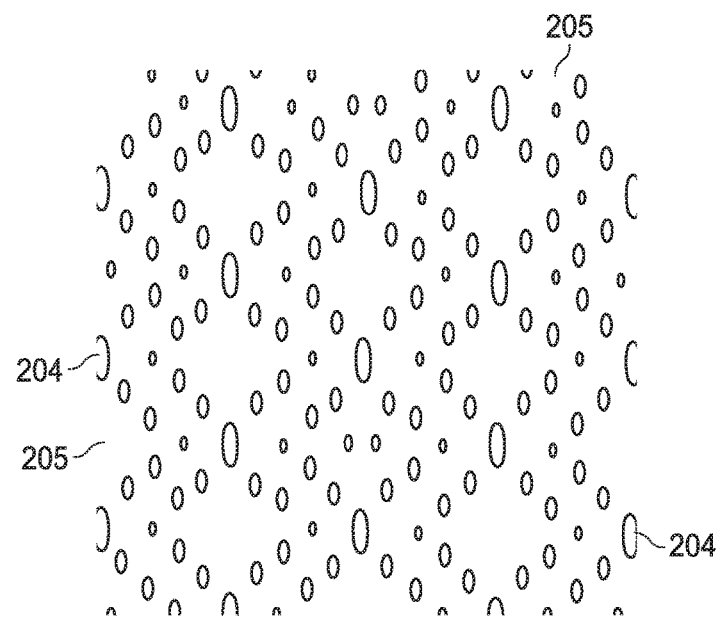
FIG. 16 is a photograph of an example apertured web produced using a weakening arrangement in accordance with the present disclosure.

A photograph of an exemplary roller that may be used as patterned calendar roller 110 in the process 100 of FIG. 11 to produce the apertured webs of the present disclosure are illustrated in FIG. 13. The pattern of protuberances 116 on the rollers in FIG. 13 would be formed in the precursor web 102, much like the melt-stabilized locations 202 of FIG. 12. Exemplary apertured webs produced from the various rolls after cross-directional tensioning of the precursor material 102 are illustrated in FIGS. 14, 15, and 16, with the apertures being indicated as element 204 and the land areas (i.e., non-apertured areas) being indicated as element 205. As seen in FIGS. 14, 15, and 16, apertures 204 and/or aperture arrays have been formed in the webs 102. The land areas 205 in FIGS. 14, 15, and 16 correspond to areas in the precursor material 102 that have not been melt stabilized or overbonded. Stated another way, the land areas have not been contacted by a protuberance on the roller 110.

The protuberances 116 may extend radially outwardly from surface 114 and have distal end surfaces 117. The anvil roller 112 may be a smooth surfaced, circular cylinder of steel, rubber or other material. The anvil roller 112 and the patterned calendar roller 110 may be switched in position (i.e., anvil on top) and achieve the same result.

From the weakening roller arrangement 108, the material 102 passes through a nip 130 formed by an incremental stretching system 132 employing opposed pressure applicators having three-dimensional surfaces which at least to a degree may be complementary to one another.

Figure 17:
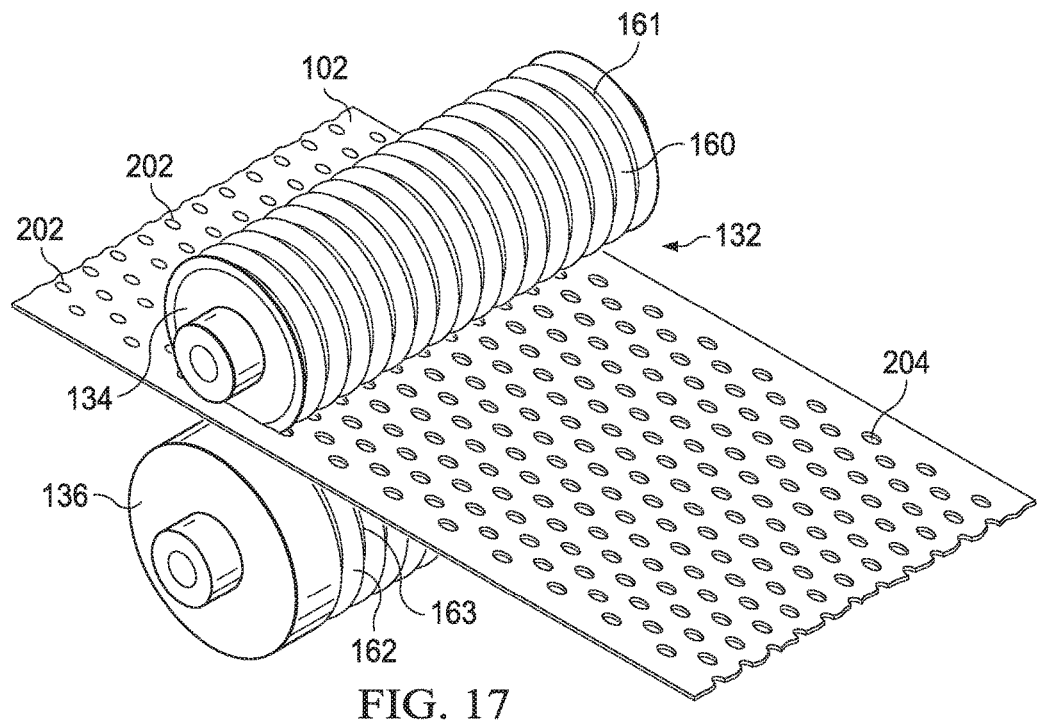
FIG. 17 is a perspective view of an incremental stretching system of the process of FIG. 11 in accordance with the present disclosure.

Referring now to FIG. 17, there is shown a fragmentary enlarged view of the incremental stretching system 132 comprising two incremental stretching rollers 134 and 136. The incremental stretching roller 134 may comprise a plurality of teeth 160 and corresponding grooves 161 which may about the entire circumference of roller 134. The incremental stretching roller 136 may comprise a plurality of teeth 162 and a plurality of corresponding grooves 163. The teeth 160 on the roller 134 may intermesh with or engage the grooves 163 on the roller 136 while the teeth 162 on the roller 136 may intermesh with or engage the grooves 161 on the roller 134. As the precursor material 102 having weakened, melt-stabilized locations 202 passes through the incremental stretching system 132 the precursor material 102 is subjected to tensioning in the CD causing the material 102 to be extended (or activated) in the CD, or generally in the CD. Additionally the material 102 may be tensioned in the MD, or generally in the MD. The CD tensioning force placed on the material 102 is adjusted such that it causes the weakened, melt-stabilized locations 202 to at least partially, or fully, rupture thereby creating a plurality of partially formed, or formed apertures 204 coincident with the weakened melt-stabilized locations 202 in the material 102. However, the bonds of the material 102 (in the non-overbonded areas) are strong enough such that they do not rupture during tensioning, thereby maintaining the material 102 in a coherent condition even as the weakened, melt-stabilized locations rupture. However, it may be desirable to have some of the bonds rupture during tensioning.

Figure 18:
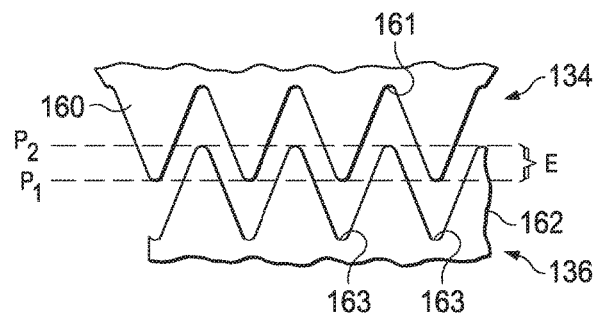
FIG. 18 is an enlarged view showing the details of teeth of the incremental stretching system of FIG. 17 in accordance with the present disclosure.

Referring to FIG. 18, a more detailed view of the teeth 160 and 162 and the grooves 161 and 163 on the rollers 134 and 136 is illustrated. The term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth is measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 160 in one roll may be offset by about one-half of the pitch from the teeth 162 in the other roll, such that the teeth of one roll (e.g., teeth 160) mesh in the valley (e.g., groove 163) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 18, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular laminate webs may be dependent upon the height and the pitch of the teeth and/or the structure of the material. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

As the material 102 having the weakened, melt-stabilized locations 202 passes through the incremental web stretching apparatus 132, the material 102 is subjected to tensioning in the cross machine direction, or substantially in the cross machine direction, thereby causing the nonwoven web 102 to be extended in the cross machine direction. The tensioning force placed on the material 102 may be adjusted by varying the pitch, DOE, or teeth size, such that the incremental stretching is sufficient to cause the weakened, melt-stabilized locations 202 to at least partially, or fully rupture, thereby creating, or at least partially creating, a plurality of apertures 204 coincident with the weakened, melt-stabilized locations 202 in the material 102.

Figure 19:
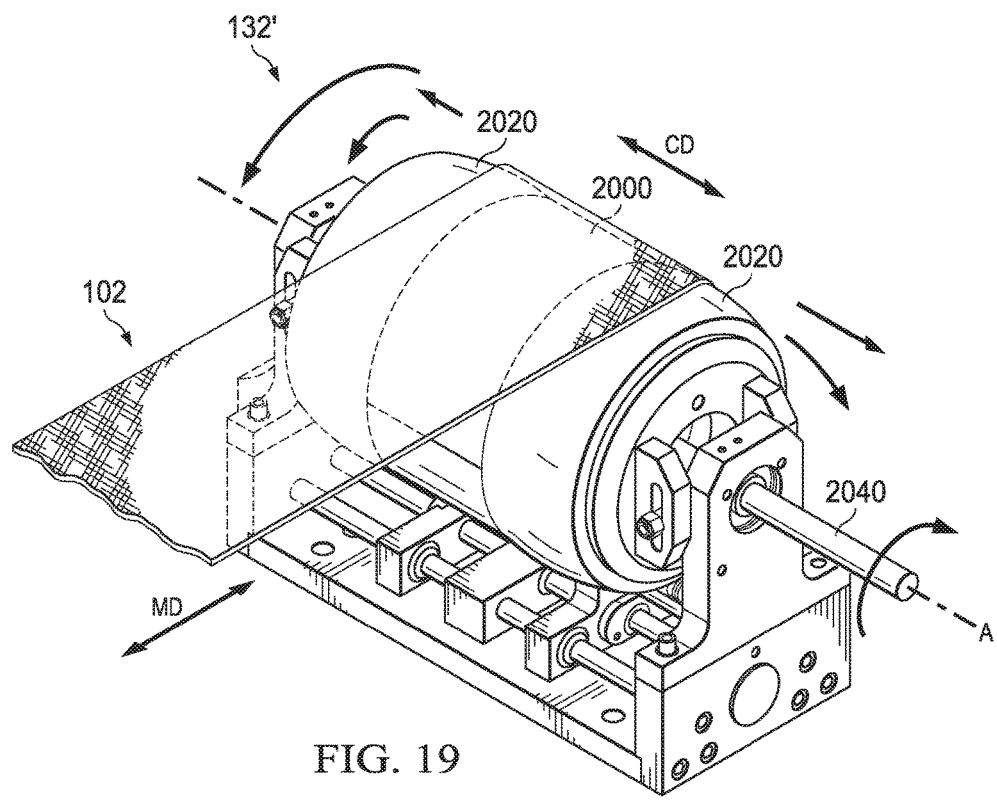
FIG. 19 is a perspective view of an example cross machine directional tensioning apparatus of the process of FIG. 11 in accordance with the present disclosure.

After the material 102 passes through the incremental web stretching apparatus 132, the web 102 may be advanced to and at least partially around a cross machine directional tensioning apparatus 132' (see e.g., FIGS. 11 and 19). The cross machine directional tensioning apparatus 132' may be offset from the main processing line by running the web partially around two idlers 133 and 135 or stationary bars, for example. In other instances, the cross machine tensioning apparatus 132' may be positioned in line with the main processing line. The cross machine directional tensioning apparatus 132' may comprise a roll that comprises at least one outer longitudinal portion that expands along a longitudinal axis, A, of the roll, relative to a middle portion of the roll, to stretch and/or expand the material 102 in the cross machine direction. Instead of or in addition to expanding along the longitudinal axis, A, of the roll, the outer longitudinal portion may be angled relative to the longitudinal axis, A, of the roll in a direction away from the material 102 being advanced over the roll to stretch the material 102 in the cross machine direction or generally in the cross machine direction. In an instance, the roll may comprise two outer longitudinal portions that each may expand in opposite directions generally along the longitudinal axis, A, of the roll. The two outer portions may both be angled downwards in a direction away from the material 102 being advanced over the roll. This movement or positioning of the outer longitudinal portions of the roll allows for generally cross machine directional tensioning of the material 102, which causes the plurality of weakened locations 202 to rupture and/or be further defined or formed into apertures 204.

The outer longitudinal portions of the roll may comprise vacuum, a low tack adhesive, a high coefficient of friction material or surface, such as rubber, and/or other mechanisms and/or materials to hold the material 102 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the material 102 from slipping relative to the longitudinal axis, A, of the roll during stretching of the outer lateral portions of the material in the cross machine direction or generally in the cross machine direction.

FIG. 19 is a top perspective view of the example cross machine directional tensioning apparatus 132'. The cross machine directional tensioning apparatus 132' may comprise a roll comprising a middle portion 2000 and two outer longitudinal portions 2020 situated on either end of the middle portion 2000. The roll may rotate about its longitudinal axis, A, on a drive shaft 2040. The roll may rotate relative to the drive shaft 2040 or in unison with the drive shaft 2040, as will be recognized by those of skill in the art. The material 102 may be advanced over the entire cross machine directional width of the middle portion 2000 and at least portions of the cross machine directional widths of the outer longitudinal portions 2020. The material 102 may be advanced over at least about 5% up to about 80% of the circumference of the roll so that the cross machine directional stretching may be performed.

Figure 20:
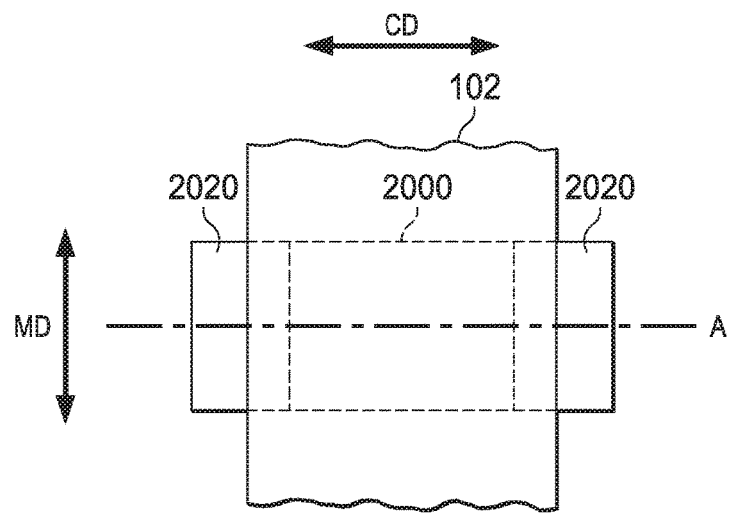
FIG. 20 is a schematic representation of a front view of an example cross machine directional tensioning apparatus with outer longitudinal portions in an unexpanded and non-angled position relative to a middle portion in accordance with the present disclosure.
Figure 21:
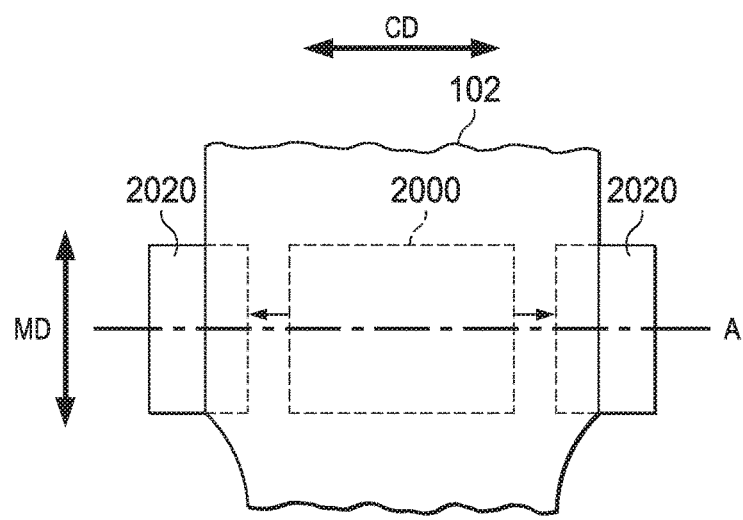
FIG. 21 is a schematic representation of a front view of the cross machine directional tensioning apparatus of FIG. 20 with the outer longitudinal portions in a longitudinally expanded position relative to the middle portion in accordance with the present disclosure.
Figure 22:
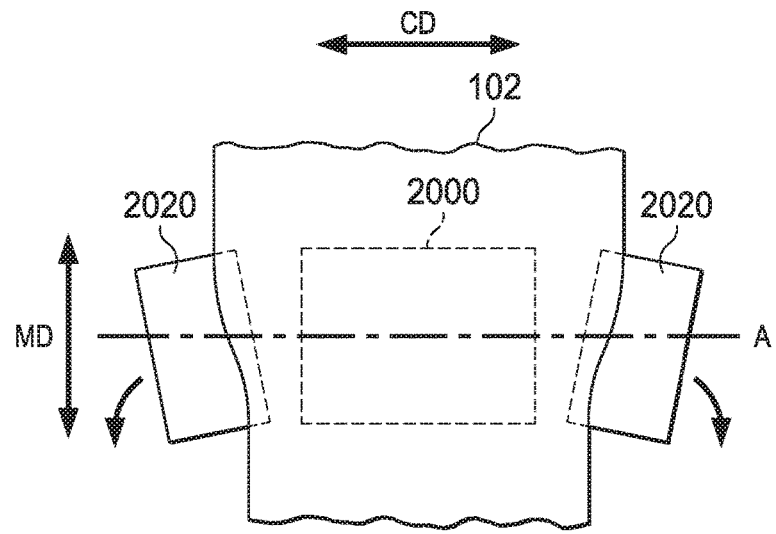
FIG. 22 is a schematic representation of a front view of the cross machine directional tensioning apparatus of FIG. 20 with the outer longitudinal portions in an angled and expanded position relative to the middle portion in accordance with the present disclosure.
Figure 23:
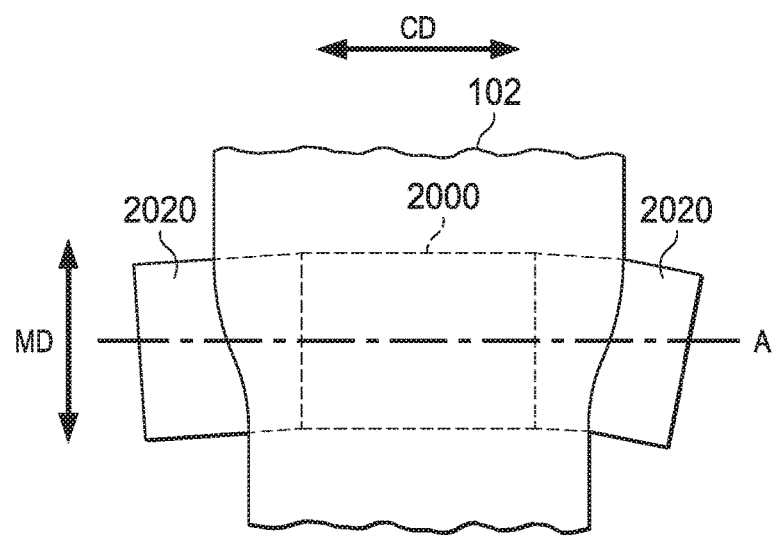
FIG. 23 is a schematic representation of a front view of a cross machine directional tensioning apparatus with outer longitudinal portions fixed in an angled position relative to a middle portion in accordance with the present disclosure.

FIG. 20 is a schematic representation of a front view of an example cross machine directional tensioning apparatus with outer longitudinal portions 2020 in an unexpanded or non-angled position relative to the middle portion 2000. FIG. 21 is a schematic representation of a front view of the cross machine directional tensioning apparatus of FIG. 20 with the outer longitudinal portions 2020 in a longitudinally expanded position relative to the middle portion 2000. FIG. 22 is a schematic representation of a front view of the cross machine directional tensioning apparatus of FIG. 20 with the outer longitudinal portions 2020 in an angled and expanded position relative to the middle portion 2000. In regard to FIG. 22, the outer longitudinal portions 2020 may merely move or slide in a direction generally perpendicular to the machine direction of the material passing over the roll to apply the cross machine directional tensioning force to the material 102. FIG. 23 is a schematic representation of a front view of a cross machine directional tensioning apparatus with the outer longitudinal portions 2020 fixed in an angled position relative to the middle portion 2000 to apply the cross machine directional tensioning force to the material 102. In such a form, the middle portion 2000 and each of the outer longitudinal portions 2020 may comprise a separate roll.

Regardless of whether one or both of the outer longitudinal portions 2020 is moved, slid, rotated, fixed, and/or expanded relative to the middle portion 2000, this relative motion or positioning between the outer longitudinal portions 2020 and the middle portion 2000 stretches the materials 102 in a cross machine direction to further rupture or further define the weakened locations 2020 in the material 102 and create, or further form, a plurality the apertures 2040 the material 102. The cross machine directional tensioning force applied by the cross machine directional tensioning apparatus 132' may be, for example, 10-25 grams or 15 grams. In an instance, the cross machine directional tensioning apparatus may be similar to, or the same as, the incremental stretching apparatus 132 to apply the cross machine directional tensioning force. In still other instances, any suitable cross machine directional tensioning apparatus may be used to apply the cross machine directional tensioning force to the material 102.

If desired, the incremental stretching step or the cross machine directional stretching step described herein may be performed at elevated temperatures. For example, the material 102 and/or the rolls may be heated. Utilizing heat in the stretching step may serve to soften the material, and may aid in extending the fibers without breaking.

Referring again to FIG. 11, the material 102 may be taken up on wind-up roll 180 and stored. Alternatively, the material 102 may be fed directly to a production line where it is used to form a portion of an absorbent article or other consumer product.

It is important to note that the overbonding step illustrated in FIGS. 11 and 12 could be performed by the material supplier and then the material may be shipped to a consumer product manufacturer to perform step 132. In fact, the overbonding step may be used in the nonwoven production process to form overbonds, which may be in addition to, or in lieu of, primary bonds formed in the nonwoven production process. Alternatively, the material supplier may fully perform the steps illustrated in FIG. 11 and then the material may be shipped to the consumer product manufacturer. The consumer product manufacturer may also perform all of the steps in FIG. 11 after obtaining a nonwoven material from a nonwoven material manufacturer.

One of ordinary skill in the art will recognize that it may be advantageous to submit the material 102 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the material or only in certain regions of the material depending on the final desired characteristics.

Returning now to FIGS. 14, 15, and 16, there is shown photographs of example apertured webs after having been subjected to the tensioning force applied by the incremental stretching system 132 and the cross machine directional tensioning apparatus 132'. As can be seen in the photographs of FIGS. 14, 15, and 16, the apertured webs now include a plurality of apertures 204 which are coincident with the weakened, melt-stabilized locations made by the rolls 17-19, respectively. A portion of the circumferential edges of an aperture 204 may include remnants of the melt-stabilized locations. It is believed that the remnants help to resist further tearing of the material particularly when the material is used as a portion of an absorbent article or another consumer product.

Percent of CD Stretch

Figure 24:
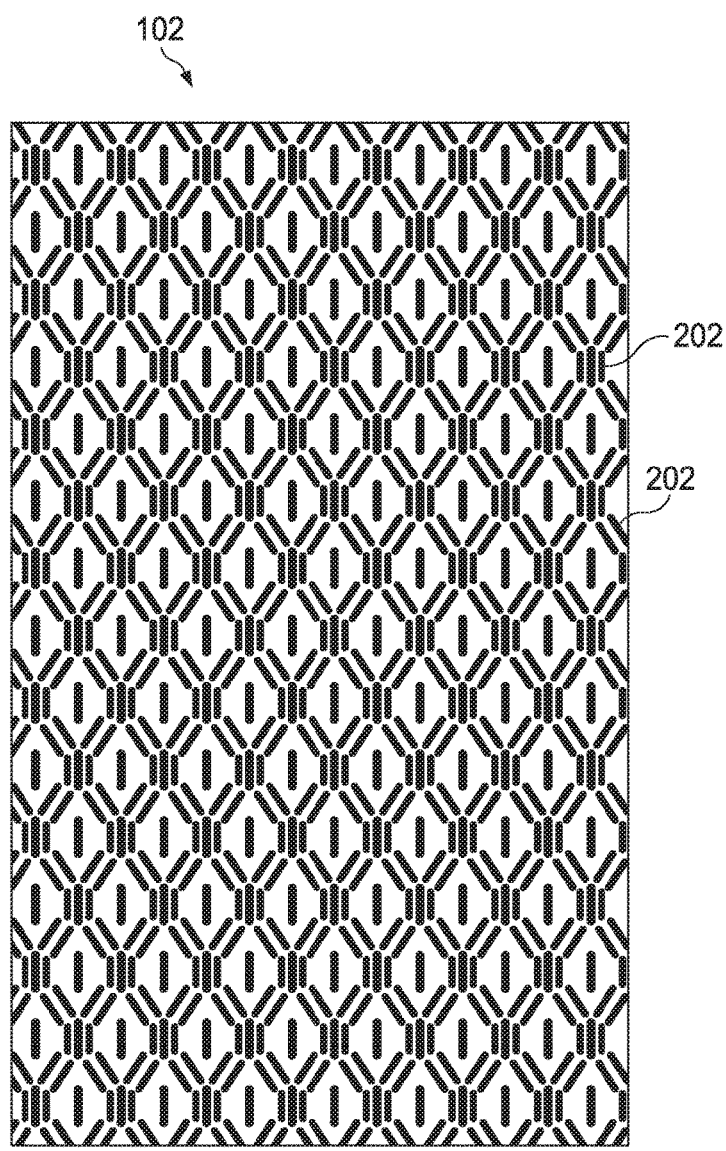
FIG. 24 is an example overbond bond pattern for the roller 110 of FIG. 13 in accordance with the present disclosure.
Figure 25:
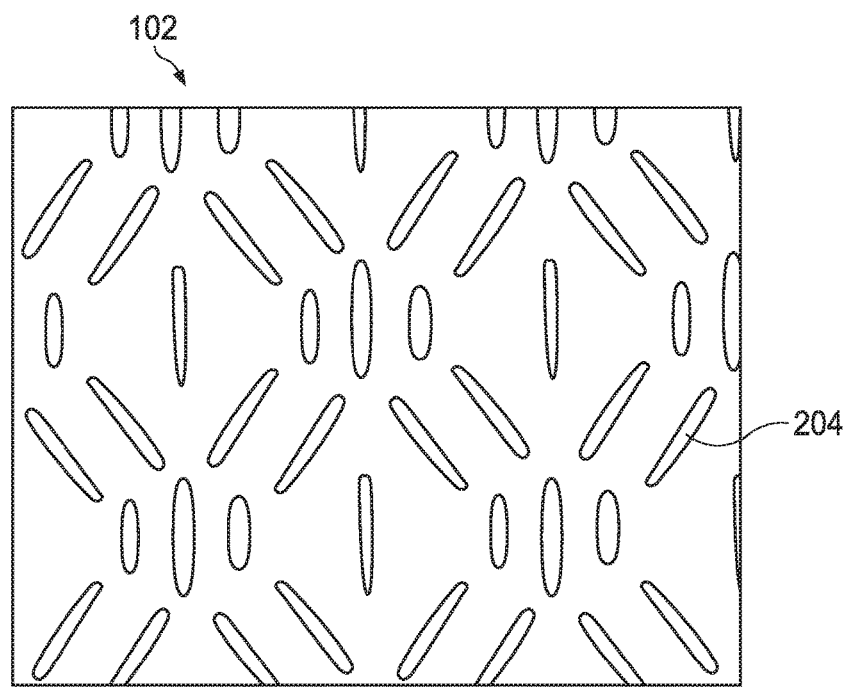
FIG. 25 is a photograph of an example apertured web produced using the overbond pattern of FIG. 24 and having been subjected to a 25% cross directional stretch using the equipment illustrated in FIG. 20 in accordance with the present disclosure.
Figure 26:
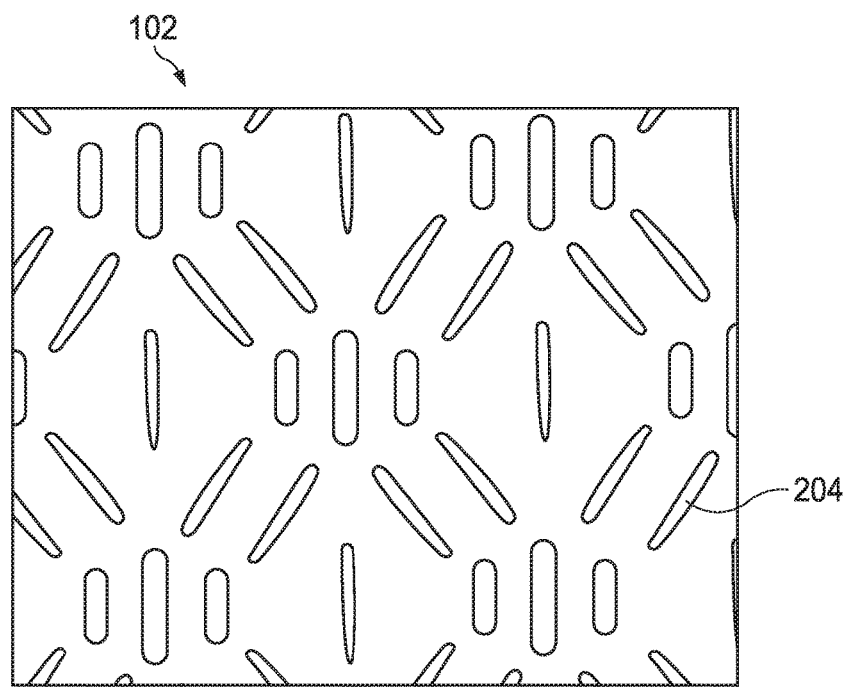
FIG. 26 is a photograph of an example apertured web produced using the overbond pattern of FIG. 24 and having been subjected to a 35% cross directional stretch using the equipment illustrated in FIG. 20 in accordance with the present disclosure.
Figure 27:
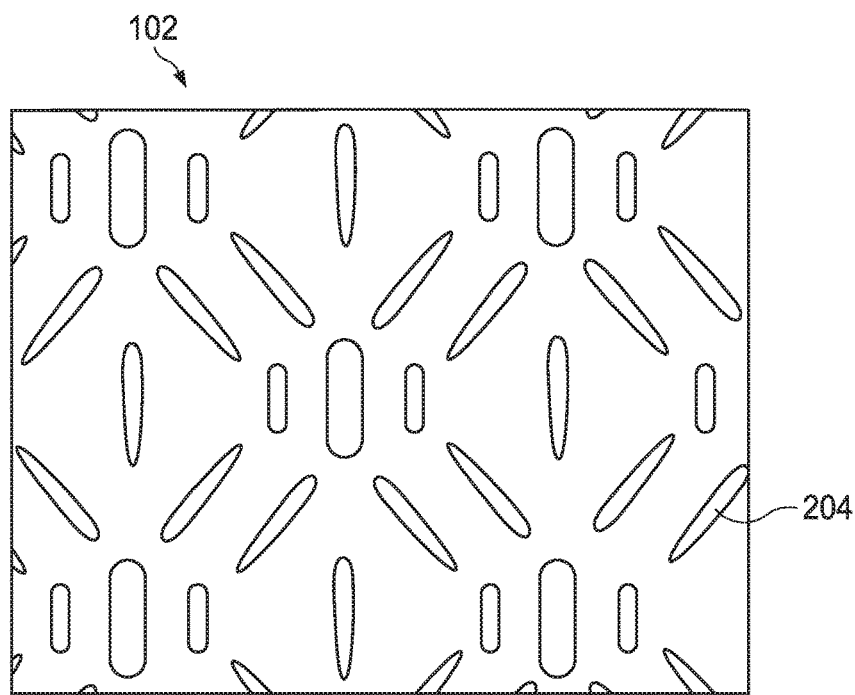
FIG. 27 is a photograph of an example apertured web produced using the overbond pattern of FIG. 24 and having been subjected to a 45% cross directional stretch using the equipment illustrated in FIG. 20 in accordance with the present disclosure.
Figure 28:
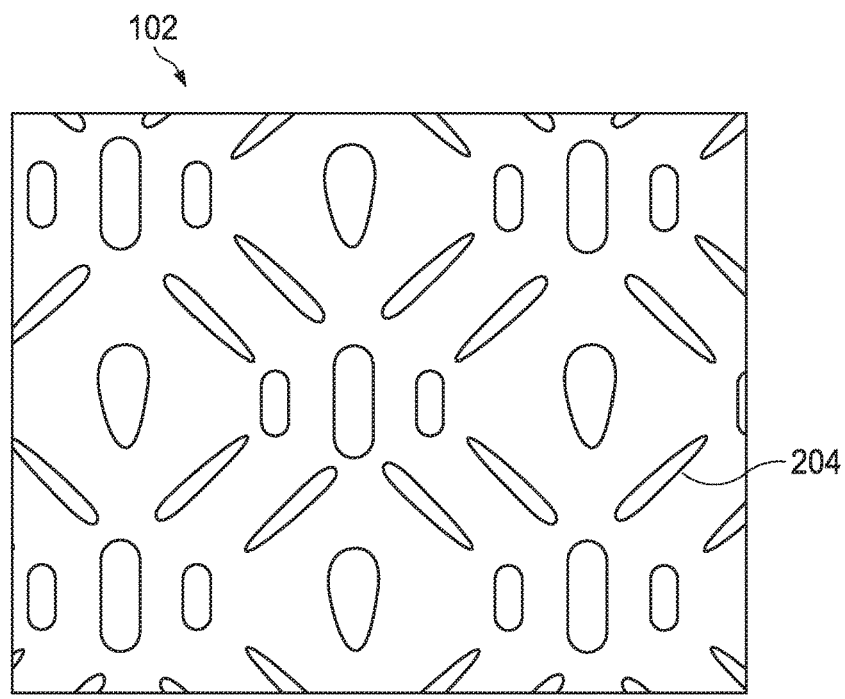
FIG. 28 is a photograph of an example apertured web produced using the overbond pattern of FIG. 24 and having been subjected to a 55% cross directional stretch using the equipment illustrated in FIG. 20 in accordance with the present disclosure.

The extent to which the material 102 is stretched in the CD may have a correlation to the size, shape, and area of the apertures. In general, the apertures may have a larger area and be more open the more the material 102 is stretched in the CD direction by the cross machine directional tensioning apparatus 132'. As such, a manufacturer can further vary an aperture pattern based on the amount of CD tensioning applied to a material even when the melt-stabilized pattern in the material is the same. As an example, FIG. 24 illustrates an overbond pattern in a material 102 prior to the incrementally stretching step 132 and the cross machine directional tension step 132. The plurality of melt stabilized locations are indicated as 202. The material is then run through the incrementally stretching step 132 and the cross machine directional tensioning apparatus 132'. The cross machine directional tensioning apparatus 132' may be set to extend the material 102 to over 100% of its CD width "W" after exiting the incremental stretching apparatus 132, such as 125%, 135%, 145%, 155% of W. In other instances, the material 102 may be stretched in the cross machine direction in the range of about 110% to about 180% of W, about 120% to about 170% of W, specifically reciting all 0.5% increments within the specified ranges and all ranged formed therein or thereby. FIG. 25 illustrates an example of the material 102 with the overbond pattern of FIG. 24 and stretched to 125% of W. FIG. 26 illustrates an example of the material 102 with the overbond pattern of FIG. 24 and stretched to 135% of W. FIG. 27 illustrates an example of the material 102 with the overbond pattern of FIG. 24 and stretched to 145% of W. FIG. 28 illustrates an example of the material 102 with the overbond pattern of FIG. 24 and stretched to 155% of W. As illustrated, the amount of CD stretch can be a significant factor on the apertured web produced.

Other suitable processes for forming apertures in a web are described in U.S. Pat. Nos. 8,679,391 and 8,158,043, and U.S. Patent Application Publication Nos. 2001/0024940 and 2012/0282436. Other suitable processes are described in U.S. Pat. Nos. 3,566,726; 4,634,440; and 4,780,352.

Absorbent Article

Figure 29:
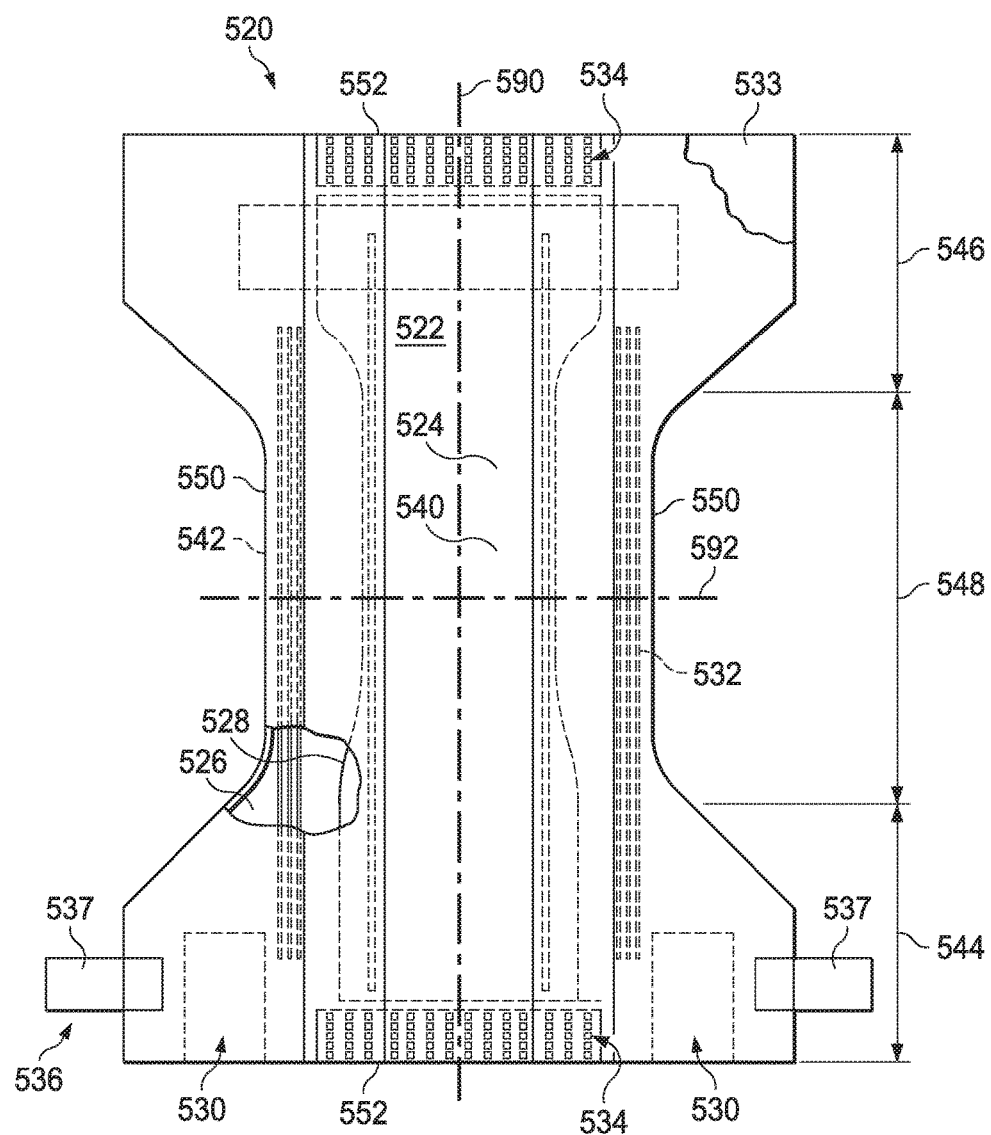
FIG. 29 is a plan view of an example disposable absorbent article having portions cut away to reveal underlying structure that may comprise one or more apertured webs, the inner surface of the absorbent article is facing the viewer in accordance with the present disclosure.

As described herein, the apertured webs of the present disclosure may be used as one or more components of an absorbent article. An example absorbent article is set forth below. FIG. 29 is a plan view of an example absorbent article that is a diaper 520 in its flat-out, uncontracted state (i.e., with elastic induced contraction pulled out) with portions of the structure being cut-away to more clearly show the construction of the diaper 520 and with the portion of the diaper 520 which faces the wearer, the inner surface 540, facing the viewer. The diaper 520 may comprise a chassis 522 comprising a liquid pervious topsheet 524, a liquid impervious backsheet 526 joined to the topsheet, and an absorbent core 528 positioned at least partially between the topsheet 524 and the backsheet 526. The diaper 520 may comprise elasticized side panels 530, elasticized leg cuffs 532, elasticized waistbands 534, and a fastening system 536 that may comprise a pair of securement members 537 and a landing member (not illustrated) on a garment-facing surface or outer surface 542. The diaper 520 may also comprise an outer cover 533 that may comprise one or more of the patterned adhesive webs of the present disclosure. The outer cover 533 may comprise nonwoven materials and/or films.

The diaper 520 is shown to have an inner surface 40 (facing the viewer in FIG. 29), an outer surface 542 opposed to the inner surface 540, a rear waist region 544, a front waist region 546 opposed to the rear waist region 544, a crotch region 548 positioned between the rear waist region 544 and the front waist region 546, and a periphery which is defined by the outer perimeter or edges of the diaper 520 in which the longitudinal edges are designated 550 and the end edges are designated 552. The inner surface 540 of the diaper 520 comprises that portion of the diaper 520 which is positioned adjacent to the wearer's body during use (i.e., the inner surface 540 generally is formed by at least a portion of the topsheet 524 and other components joined to the topsheet 524). The outer surface 542 comprises that portion of the diaper 520 which is positioned away from the wearer's body (i.e., the outer surface 542 is generally formed by at least a portion of the backsheet 526 and other components joined to the backsheet 526). The rear waist region 544 and the front waist region 546 extend from the end edges 552 of the periphery to the crotch region 548.

The diaper 520 also has two centerlines, a longitudinal centerline 590 and a transverse centerline 592. The term "longitudinal", as used herein, refers to a line, axis, or direction in the plane of the diaper 520 that is generally aligned with (e.g., approximately parallel with) a vertical plane which bisects a standing wearer into left and right halves when the diaper 520 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The chassis 522 of the diaper 520 is shown in FIG. 29 as comprising the main body of the diaper 520. The containment assembly 522 may comprise at least the topsheet 524, the backsheet 526, and the absorbent core 528. When the absorbent article 520 comprises a separate holder and a liner, the chassis 522 may comprise the holder and the liner (i.e., the chassis 522 comprises one or more layers of material to define the holder while the liner comprises an absorbent composite such as a topsheet, a backsheet, and an absorbent core.) For unitary absorbent articles (or one piece), the chassis 522 comprises the main structure of the diaper with other features added to form the composite diaper structure. Thus, the chassis 522 for the diaper 520 generally comprises the topsheet 524, the backsheet 526, and the absorbent core 528.

FIG. 29 shows a form of the chassis 522 in which the topsheet 524 and the backsheet 526 have length and width dimensions generally larger than those of the absorbent core 528. The topsheet 524 and the backsheet 526 extend beyond the edges of the absorbent core 528 to thereby form the periphery of the diaper 520. While the topsheet 524, the backsheet 526, and the absorbent core 528 may be assembled in a variety of well-known configurations know to those of skill in the art.

The absorbent core 528 may be any absorbent member which is generally compressible, conformable, non-irritating to the wearer's skin, and capable of absorbing and retaining liquids such as urine and other certain body exudates. As shown in FIG. 29, the absorbent core 528 has a garment-facing side, a body-facing side, a pair of side edges, and a pair of waist edges. The absorbent core 528 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. The absorbent core may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 528 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 528 may also be varied to accommodate wearers ranging from infants through adults. However, the total absorbent capacity of the absorbent core 528 should be compatible with the design loading and the intended use of the diaper 520.

Figure 30:
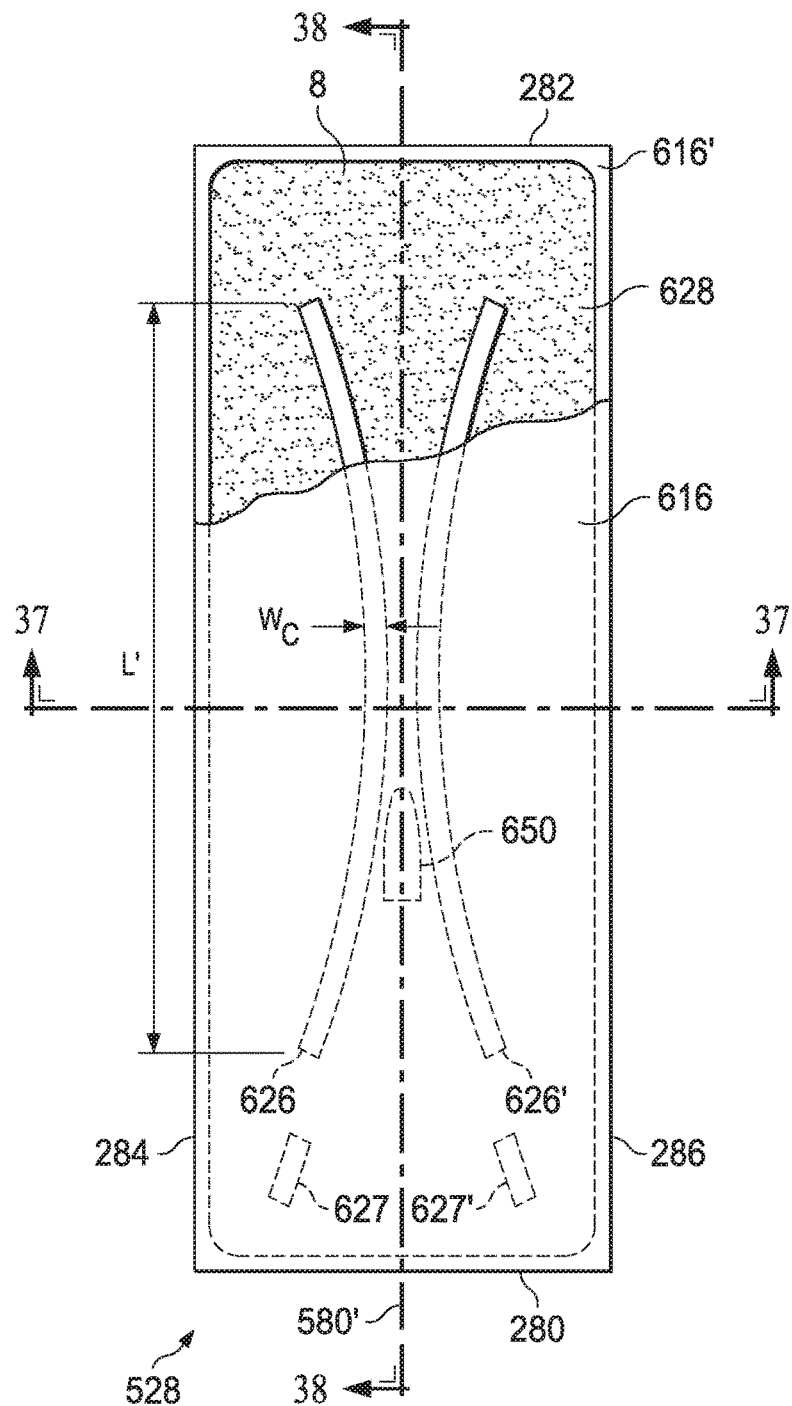
FIG. 30 is a top view of an example absorbent core of an absorbent article with some layers partially removed, wherein the absorbent core comprises one or more channels in accordance with the present disclosure.
Figure 31:
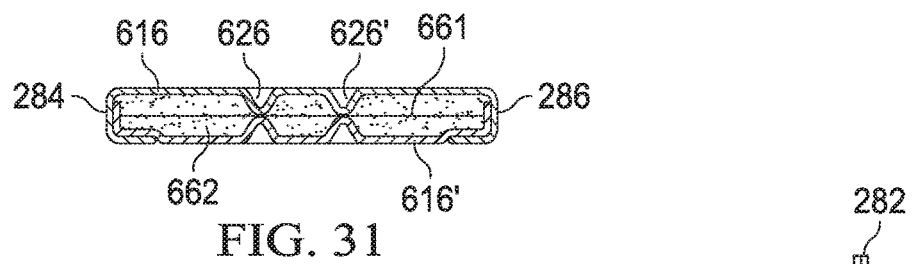
FIG. 31 is a cross-sectional view of the absorbent core taken about line 37-37 of FIG. 30 in accordance with the present disclosure.
Figure 32:
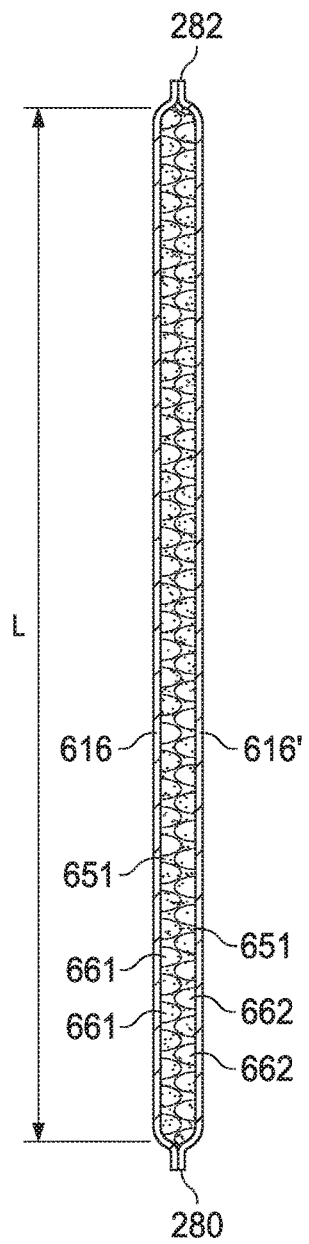
FIG. 32 is a cross-sectional view of the absorbent core taken about line 38-38 of FIG. 30 in accordance with the present disclosure.

Referring to FIGS. 30-32, the absorbent core 528 of the absorbent articles may comprise one or more channels 626, 626', 627, 627' (627 and 627' are shown in dash in FIG. 30), such as two, three, four, five, or six channels. The absorbent core 528 may comprise a front side 280, a rear side 282, and two longitudinal sides 284, 286 joining the front side 280 and the rear side 282. The absorbent core 528 may comprise one or more absorbent materials. The absorbent material 628 of the absorbent core 528 may be distributed in higher amounts towards the front side 280 than towards the rear side 282 as more absorbency may be required at the front of the absorbent core 528 in particular absorbent articles. The front side 280 may be positioned generally in the front waist region of an absorbent article and the rear side 282 may be positioned generally in the rear waist region of an absorbent article.

A core wrap (i.e., the layers enclosing the absorbent material of the absorbent core 528) may be formed by two nonwoven materials, substrates, laminates, films, or other materials 616, 616'. The core wrap may be at least partially sealed along the front side 280, the rear side 282, and/or the two longitudinal sides 284, 286 of the absorbent core 528 so that substantially no absorbent material is able to exit the core wrap. In a form, the core wrap may only comprise a single material, substrate, laminate, or other material wrapped at least partially around itself. The first material, substrate, or nonwoven 616 may at least partially surround a portion of the second material, substrate, or nonwoven 116' to form the core wrap, as illustrated as an example in FIG. 31. The first material 616 may surround a portion of the second material 616' proximate to the first and second side edges 284 and 286 and/or the front side 280 and the rear side 282.

The absorbent core 528 of the present disclosure may comprise one or more adhesives, for example, to help immobilize the SAP or other absorbent materials within the core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

The absorbent material may comprise one or more continuous layers present within the core wrap with channels having no, or little (e.g., 0.1%-10%) absorbent material positioned therein. In other forms, the absorbent material may be formed as individual pockets or stripes within the core wrap. In the first case, the absorbent material may be, for example, obtained by the application of the continuous layer(s) of absorbent material, with the exception of the absorbent material free, or substantially free, channels. The continuous layer(s) of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 to Hundorf et al., for example. The absorbent core 528 may comprise a first absorbent layer and at least a second absorbent layer. The first absorbent layer may comprise the first material 616 and a first layer 661 of absorbent material, which may be 100% or less of SAP, such as 85% to 100% SAP, 90% to 100% SAP, or even 95% to 100% SAP, specifically including all 0.5% increments within the specified ranges and all ranges formed therein or thereby. The second absorbent layer may comprise the second material 616' and a second layer 662 of absorbent material, which may also be 100% or less of SAP (including the ranges specified above). The absorbent core 528 may also comprise a fibrous thermoplastic adhesive material 651 at least partially bonding each layer of the absorbent material 661, 662 to its respective material 616, 616'. This is illustrated in FIGS. 31 and 32, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis 580' of the core 528.

The fibrous thermoplastic adhesive material 651 may be at least partially in contact with the absorbent material 661, 662 in the land areas and at least partially in contact with the materials 616 and 616' in the channels 626, 626'. This imparts an essentially three-dimensional structure to the fibrous layer of thermoplastic adhesive material 651, which in itself is essentially a two-dimensional structure of relatively small thickness, as compared to the dimension in length and width directions. Thereby, the fibrous thermoplastic adhesive material 651 may provide cavities to cover the absorbent material in the land areas, and thereby immobilizes this absorbent material, which may be 100% or less of SAP (including the ranges specified above).

The channels 626, 626' may be continuous or discontinuous and may have a length of L' and a width, $W_c$, for example, or any other suitable length or width. The channels 626, 626', 627, and 627' may have a lateral vector component and a longitudinal vector component or may extend entirely longitudinally or entirely laterally. The channels may each have one or more arcuate portions. One or more channels may extend across the lateral axis or the longitudinal axis 580' of the absorbent core 528, or both.

Referring to FIG. 31, it can be seen that the channels 626 and 626' do not comprise absorbent material. In other instances, the channels 626 and 626' may comprise a relatively small amount (compared to the amount of the absorbent material within the remainder of the absorbent core 528) of absorbent material. The relatively small amount of absorbent material within the channels may be in the range of 0.1% to 20%, specifically reciting all 0.1% increments within the specified ranges and all ranges formed therein.

Referring again to FIG. 30, the absorbent core 528 may comprise one or more pockets 650 (shown in dash). The one or more pockets 650 may be provided in addition to the one or more channels or instead of the one or more channels. The pockets 650 may be areas in the absorbent core 528 that are free of, or substantially free of absorbent material, such as SAP (including the ranges specified above). The pockets 650 may overlap the longitudinal axis 580' and may be positioned proximate to the front side 280, the rear side 282, or may be positioned at a location intermediate the front side 280 and the rear side 282, such as longitudinally centrally, or generally longitudinally centrally between the front side 280 and the rear side 282.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The diaper 520 may have an asymmetric, modified T-shaped absorbent core 528 having ears in the front waist region 546 but a generally rectangular shape in the rear waist region 544. Example absorbent structures for use as the absorbent core 528 of the present disclosure that have achieved wide acceptance described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345 entitled "High Efficiency Absorbent Articles For Incontinence Management", issued to Young et al. on Sep. 15, 1992.

The backsheet 526 is positioned adjacent the garment-facing surface of the absorbent core 528 and may be joined thereto by attachment methods (not shown) such as those well known in the art. For example, the backsheet 526 may be secured to the absorbent core 528 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core is not joined to the backsheet 526, the topsheet 524, or both in order to provide greater extensibility in the front waist region 546 and the rear waist region 544.

The backsheet 526 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 526 may prevent, or at least inhibit, the exudates absorbed and contained in the absorbent core 528 from wetting articles which contact the diaper 520 such as bed sheets and undergarments, however, the backsheet 526 may permit vapors to escape from the absorbent core 528 (i.e., is breathable). Thus, the backsheet 526 may comprise a polymeric film such as thermoplastic films of polyethylene or polypropylene. A suitable material for the backsheet 526 is a thermoplastic film having a thickness of from about 0.012 mm (0.5 mil) to about 0.051 mm (2.0 mils), for example.

The topsheet 524 is positioned adjacent the body-facing surface of the absorbent core 528 and may be joined thereto and to the backsheet 526 by attachment methods (not shown) such as those well known in the art. Suitable attachment methods are described with respect to joining the backsheet 526 to the absorbent core 528. The topsheet 524 and the backsheet 526 may be joined directly to each other in the diaper periphery and may be indirectly joined together by directly joining them to the absorbent core 528 by the attachment methods (not shown).

The topsheet 524 may be compliant, soft feeling, and non-irritating to the wearer's skin. Further, the topsheet 524 may be liquid pervious permitting liquids (e.g., urine) to readily penetrate through its thickness. A suitable topsheet 524 may comprise one or more of the apertured webs of the present disclosure forming one or more layers. As described herein, the apertured webs of the present disclosure may form any other suitable components of an absorbent article or the example diaper 520, such as an over cover, an ear panel, and/or an acquisition material, for example.

Sanitary Napkin

Figure 33:
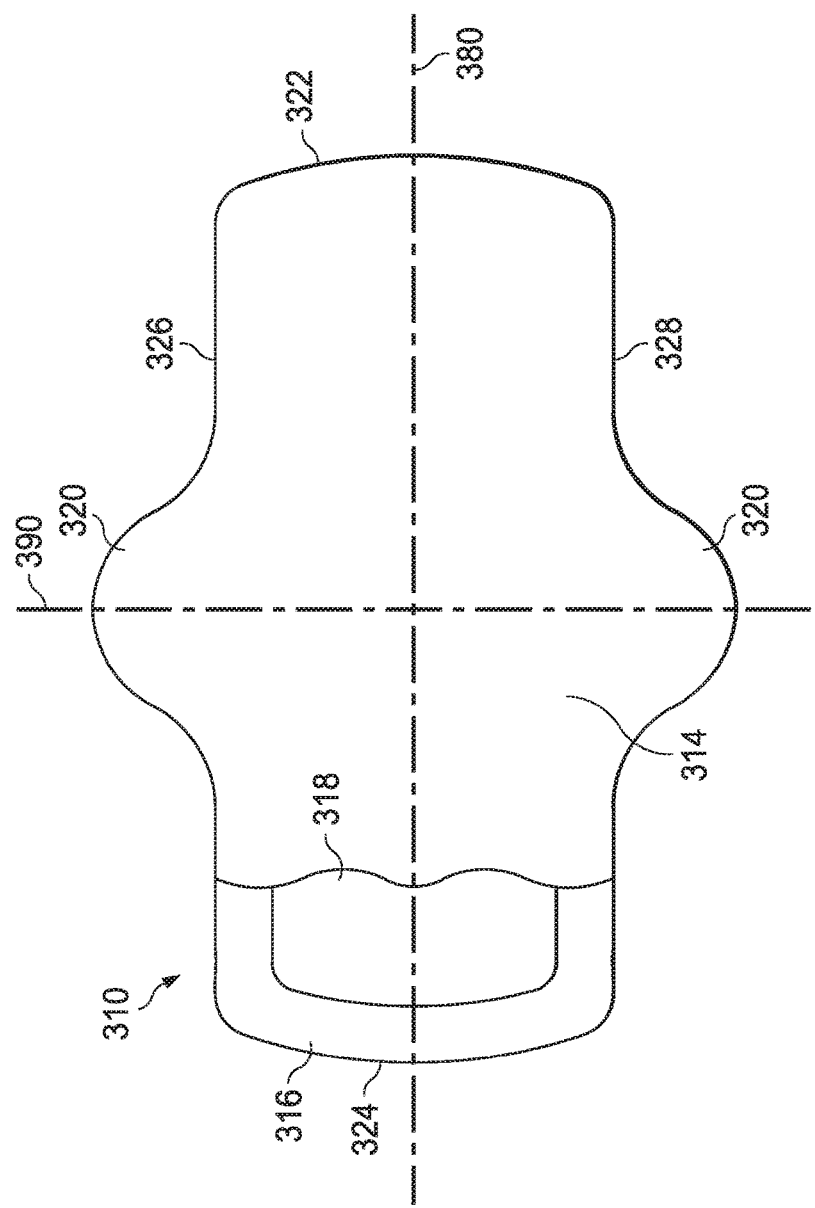
FIG. 33 is a top view of an absorbent article of the present disclosure, having portions cut away to reveal underlying structure, that is a sanitary napkin in accordance with the present disclosure.

Referring to FIG. 33, the absorbent article may be a sanitary napkin 310. A topsheet, a secondary topsheet, wings, or another portion of the sanitary napkin may comprise one or more of the apertured webs of the present disclosure. The sanitary napkin 310 may comprise a liquid permeable topsheet 314, a liquid impermeable, or substantially liquid impermeable, backsheet 316, and an absorbent core 318 positioned intermediate the topsheet 314 and the backsheet 316. The absorbent core 318 may have any or all of the features described herein with respect to the absorbent cores 528 and, in some forms, may have a secondary topsheet instead of the acquisition layer(s) disclosed above. The sanitary napkin 310 may comprise wings 320 extending outwardly with respect to a longitudinal axis 380 of the sanitary napkin 310. The sanitary napkin 310 may also comprise a lateral axis 390. The wings 320 may be joined to the topsheet 314, the backsheet 316, and/or the absorbent core 318. The sanitary napkin 310 may also comprise a front edge 322, a rear edge 324 longitudinally opposing the front edge 322, a first side edge 326, and a second side edge 328 laterally opposing the first side edge 326. The longitudinal axis 380 may extend from a midpoint of the front edge 322 to a midpoint of the rear edge 324. The lateral axis 390 may extend from a midpoint of the first side edge 328 to a midpoint of the second side edge 328. The sanitary napkin 310 may also be provided with additional features commonly found in sanitary napkins as is known in the art.

For those instances where the apertured webs of the present invention are utilized as a topsheet, 314, arrays of apertures may not cover all of the topsheet 314. For example, an array of apertures may be disposed adjacent to the longitudinal axis 380 while further outboard of the longitudinal axis 380, the topsheet 314 may comprise no array of apertures. The array of apertures may straddle the longitudinal axis 380 and extend laterally outboard therefrom such that the array of apertures is about 10 mm wide. In some forms, the array of apertures is about 15 mm wide, about 20 mm wide, about 30 mm wide, about 35 mm wide, about 40 mm wide, about 45 mm wide, about 50 mm wide, or about 55 mm wide including all values and ranges included therein. Yet in other forms, the array of apertures may extend the full width of the topsheet 314 and extend from the first side edge 326 to the second side edge 328.

Figure 89:
FIG. 89 is a cross sectional view of a disposable absorbent article or a portion thereof, constructed in accordance with the present invention.

Forms of the present invention are contemplated where apertured webs of the present invention comprise structures as described herein in the negative Z-direction. In such forms, the urging of the material of the apertured web in the negative Z-direction may fracture material of an absorbent core or a portion thereof. As shown in FIG. 89, a sanitary pad, or portion thereof, may comprise the apertured web 8914, an absorbent material 8918, and a support layer 8916. As shown the structures described herein may cause fracturing of the absorbent material 8918, particularly where the absorbent material comprises a high internal phase emulsion foam. However, other forms of the invention are contemplated where the absorbent material 8918 comprises SAP. Still in other forms, the apertured web 8914 may comprise the topsheet, the absorbent material 8918 may comprise a first liquid retention layer, and the support layer 8916 may comprise a secondary topsheet or acquisition layer. In such forms, additional absorbent cores in addition to a backsheet may be provided.

The depressions in the apertured web 8914 and absorbent material 8918 may extend through the thickness of the absorbent material 8918 such that a plurality of discrete pieces of absorbent material are produced. In other forms, the depressions in the apertured web 8914 and the absorbent material 8918 may only partially extend through the thickness of the absorbent material 8916 such that absorbent material remains a continuous element.

High internal phase emulsion foams are known in the art. Methods of making high internal phase emulsion foams are described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

Patterned Adhesive

As stated previously, the adhesive utilized to bond/join layers and/or elements of disposable absorbent articles using the apertured web of the present invention may comprise adhesive indicia. Accordingly, the apertured webs and/or absorbent articles of the present disclosure, or portions thereof, may comprise one or more patterned adhesives applied thereto or printed thereon. The patterned adhesives may be present within the apertured webs or under the apertured webs such that at least a portion of the patterned adhesives can be viewable through the apertured webs, either though apertures or land areas. Patterned adhesives are adhesives that are applied to one or more layers of the apertured webs, or between layers of the same, in particular patterns to provide the absorbent articles, or portions thereof, with certain patterns, visible patterns, and/or certain textures. Examples of printed adhesive patterns are illustrated in FIGS. 34, 35 and 82-88.

Figure 34:
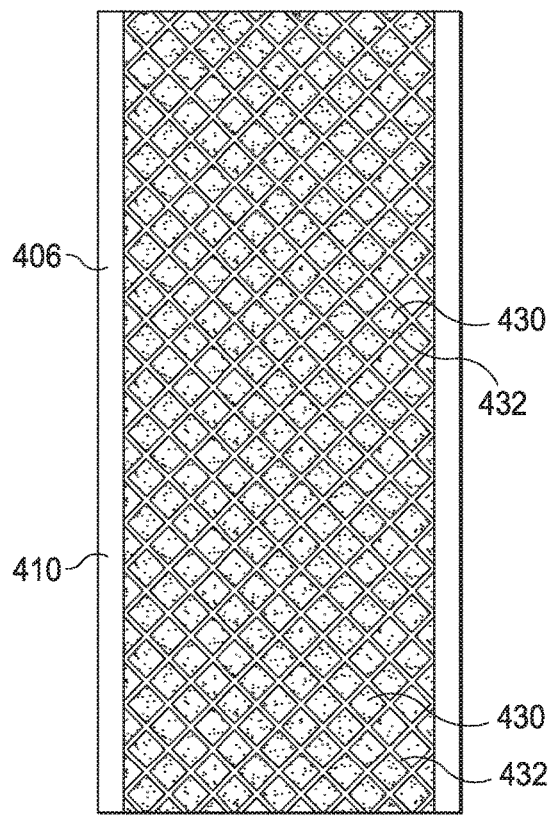
FIG. 34 is a top view of a patterned adhesive applied to a substrate for an absorbent article in accordance with the present disclosure.
Figure 35:
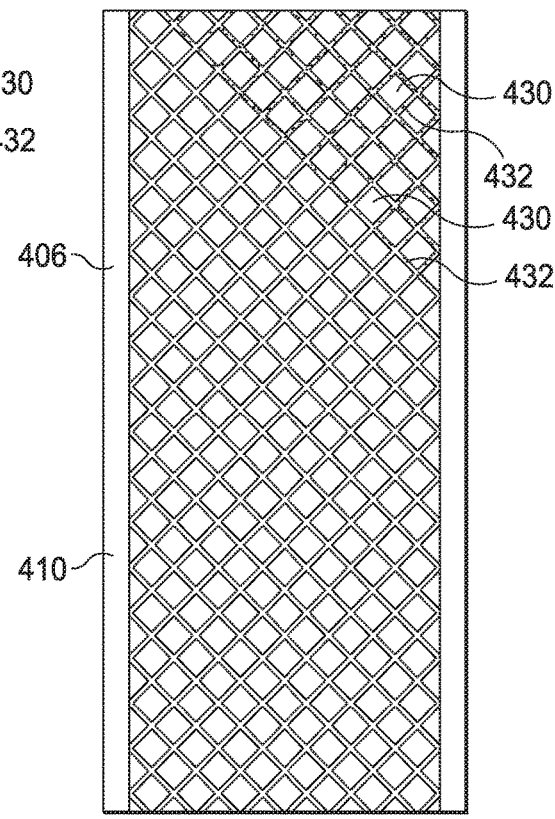
FIG. 35 is a top view of another patterned adhesive applied to a substrate for an absorbent article in accordance with the present disclosure.

In FIGS. 34 and 35, element 406, as an example, is a non-apertured layer of a apertured web onto which the patterned adhesive is applied, element 410 is a surface of the layer 406 to which the patterned adhesive is applied, element 430 is a fluid that is applied to the layer 406, such as an adhesive, and element 432 is a discrete pattern area. The two figures illustrate some examples of patterned adhesives that may be used in the apertured webs of the present disclosure. Other adhesive patterns having any suitable configuration are also within the scope of the present disclosure. The patterned adhesives may be printed on or otherwise applied to any suitable layer of the apertured webs or applied above or beneath them. Methods for applying patterned adhesives to layers or substrates by adhesive printing are disclosed, for example, in U.S. Pat. No. 8,186,296, to Brown et al., issued on May 29, 2012, and in U.S. Pat. Appl. Publ. No. 2014/0148774, published on May 29, 2014, to Brown et al. Other methods of applying patterned adhesives to substrates known to those of skill in the art are also within the scope of the present disclosure.

A patterned adhesive may have the same color or a different color as at least one layer of an apertured web. In some instances, the patterned adhesive may have the same or a different color as both or all layers of an apertured web. In some instances, aperture patterns in at least one layer of a apertured web may coordinate with a patterned of a patterned adhesive to visually create a three-dimensional appearance. The apertured patterns may be the same or different than patterns of the patterned adhesive.

In an instance, an apertured web may comprise a first layer comprising a plurality of apertures and a plurality of land areas and a second layer comprising a plurality of apertures and a plurality of land areas. A patterned pigmented substance, such as ink or a patterned adhesive, may be positioned at least partially intermediate the first layer and the second layer. The plurality of apertures of the first layer may be at least partially misaligned with the plurality of apertures of the second layer (see e.g., FIG. 8). The patterned pigmented or colored substance (29 of FIG. 8) may be at least partially viewable through the misaligned portions of the apertures in the first and second layers.

Figure 82:
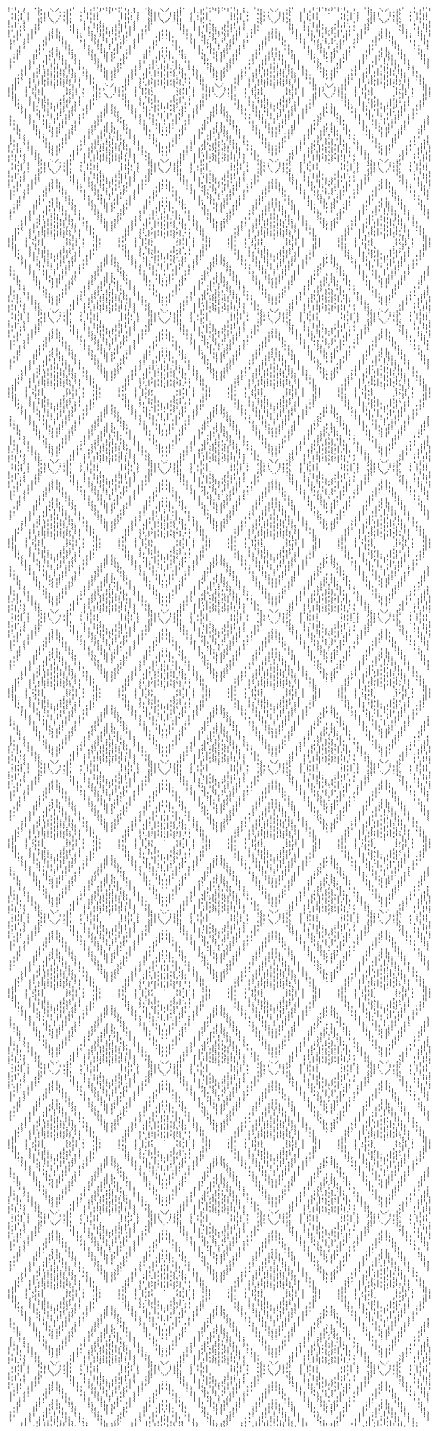
FIGS. 82-88 are illustrations showing overbonds, patterned adhesive and combination of overbonds and patterned adhesive, respectively.
Figure 83:
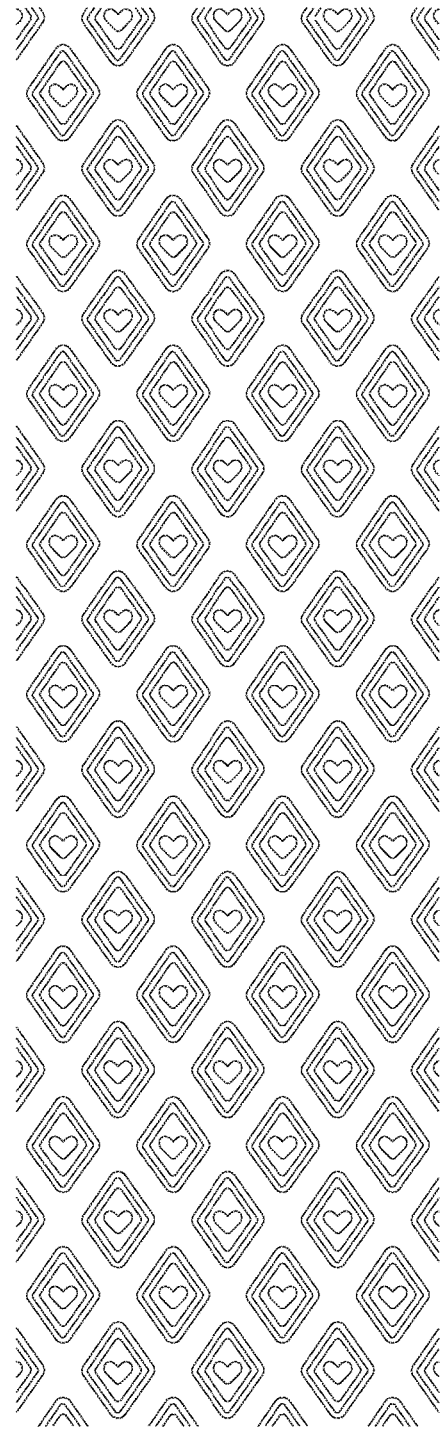
Figure 84:
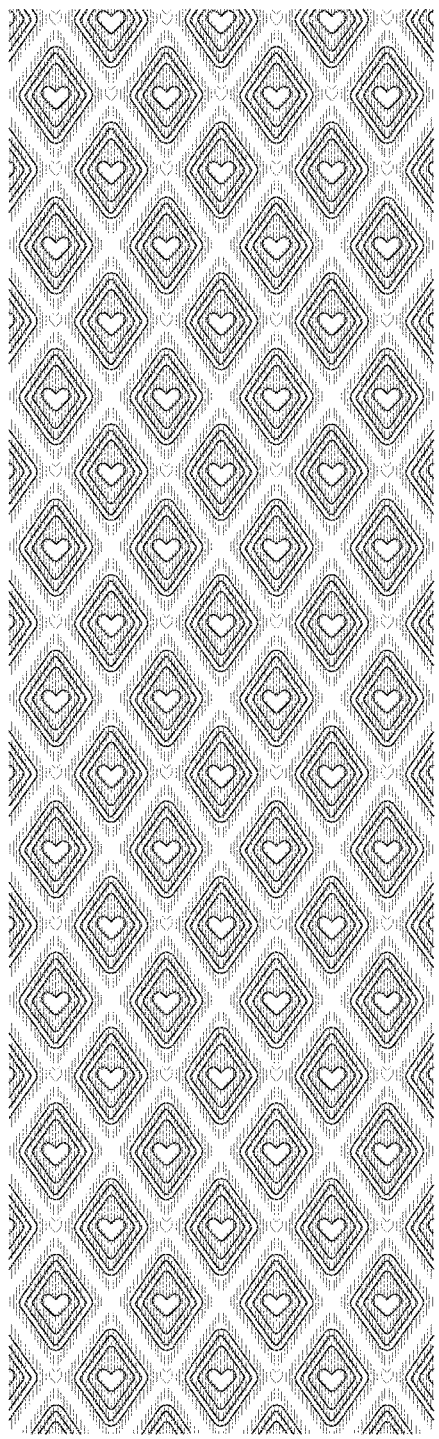
Figure 85:
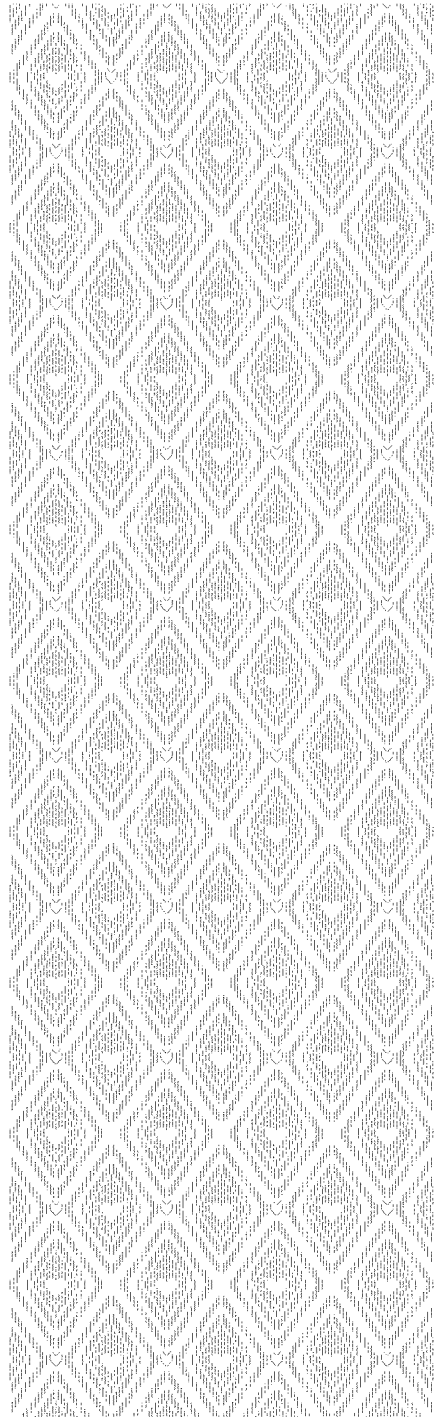
Figure 86:
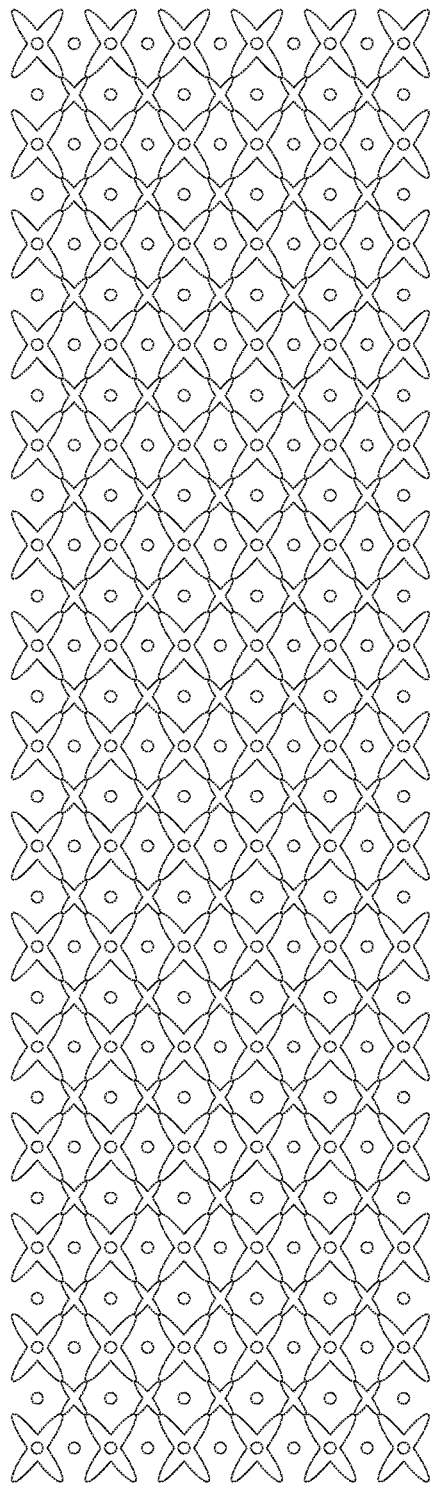
Figure 87:
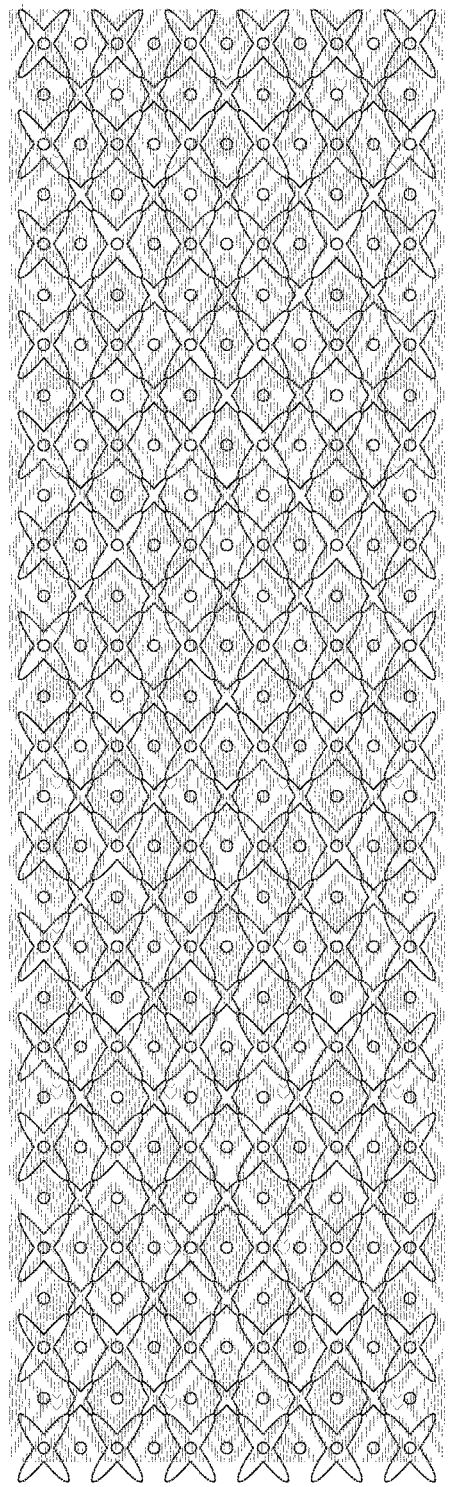

Regarding FIGS. 82-84, a plurality of overbonds are shown on a web arranged in a plurality of arrays which will eventually—when processed as described herein—produce apertured indicia. In FIG. 83 adhesive indicia on a web is depicted. As noted previously, the adhesive may comprise a color or may be clear in some forms. Regarding FIG. 84, a combination of the overbonds of FIG. 82 and the adhesive indicia of FIG. 83 are shown. Note that given the arrangement of the overbonds of FIG. 82, the resulting apertured indicia would appear similar (coordinated) with the adhesive indicia shown in FIG. 83. In such forms, it may be beneficial to register the apertured indicia with the adhesive indicia to produce the desired visual effect. Adhesive indicia and apertured indicia which may not require registration are depicted in FIGS. 85-87. A similar effect is depicted in FIG. 88.

Figure 88:
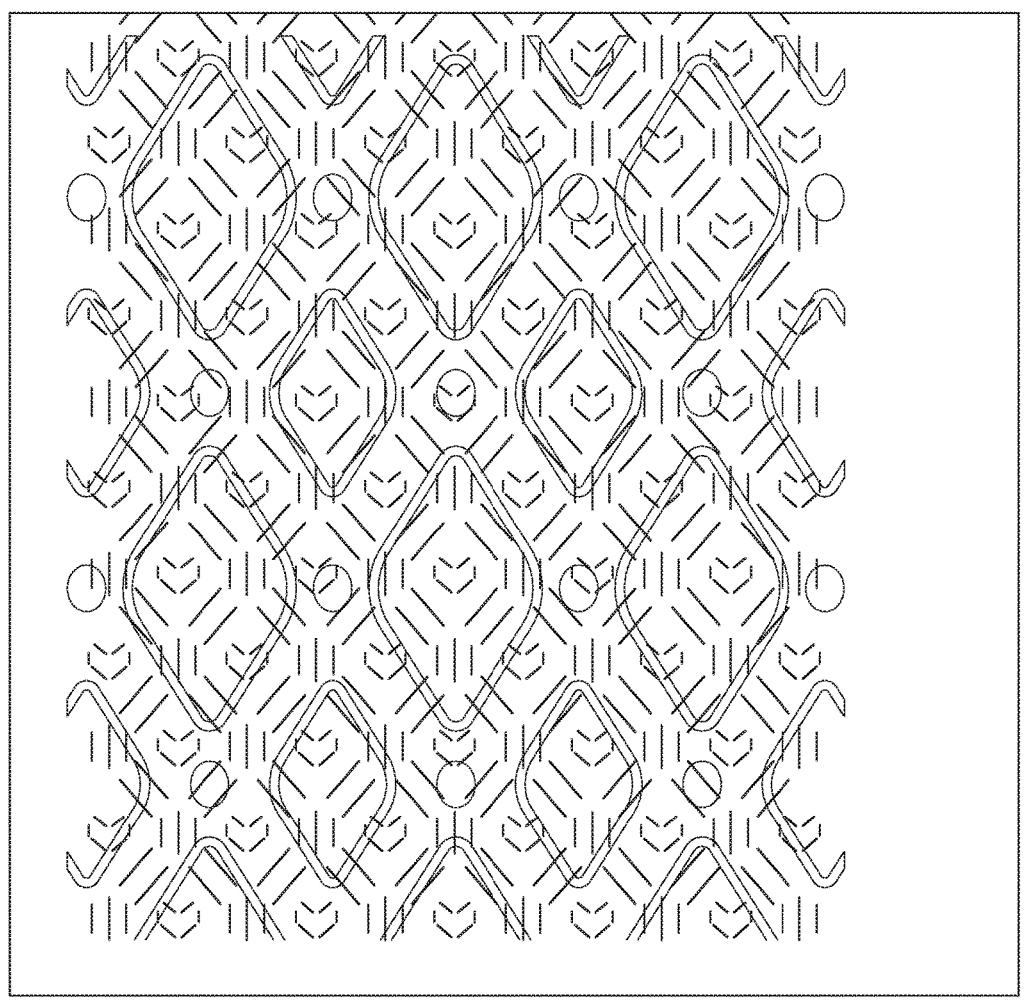

Regarding FIG. 88, a combination of apertured indicia and adhesive indicia is shown on a web. The apertured indicia and the adhesive indicia are not registered. As such, portions of the adhesive indicia are visible through only a portion of the apertures. The effect can highlight portions of the adhesive indicia which are visible through the apertures. The remainder of the adhesive indicia may still be visible through the web which comprises the apertured indicia.

Patterns

The apertures in at least one layer of an apertured web may be grouped in spaced arrays of apertures (see e.g., FIGS. 1-4 and 40-53). An aperture array includes two or more apertures having much closer spacing between the apertures than the distance between the aperture arrays. The distance between the array and other apertures is at least about 1.5, at least about 2 times, or at least about 3 times the Interaperture distance between apertures in the array. The aperture arrays may form a regular or recognizable shape, such as a heart shape, polygon, ellipse, arrow, chevron, and/or other shapes known in the pattern art. The apertures arrays may differ in one portion of the apertured web compared to another portion of the apertured web. In an absorbent article context, the aperture arrays may differ in one region of the absorbent article compared to another region of the absorbent article. Additionally, the aperture arrays may be coordinated in regions of the absorbent article where the aperture arrays are present. The apertures of the aperture arrays may perimeters which are concave, convex, or may include concavities and convexities. The aperture arrays may be organized into "macro-arrays" having a higher order structure. For example, an apertured web may comprise aperture arrays that may be separated by a continuous, inter-connected land area pattern. In such an instance, the land area pattern may function as a fluid distribution pathway and the aperture arrays may function as fluid "drains" thereby promoting fluid access to the underlying absorbent material or absorbent core. The shape of the aperture arrays may enhance the ability of the arrays to manage fluid, such as bodily exudates (i.e., urine, runny BM, menses). For example, aperture arrays including a concavity facing a fluid insult location in an absorbent article may function as fluid collection "traps" as the fluid may travel along the "land area" in the concavity to a point where the concavity ends. At this location, the fluid may enter the apertures in the direction of the fluid path or those on either side of the concavity if the fluid turns in either lateral direction. Example aperture array shapes having a concavity include heart shapes, star shapes, some polygons, crescents, and chevrons, to name a few examples.

In some forms, apertures, or arrays thereof, in an apertured web, may form one or more continuous or semi-continuous patterns, resulting in discrete "macro" land areas. In such an instance, the discrete macro land areas may function as fluid deposition regions. Fluid moving from the discrete macro land areas in any direction may be absorbed into the apertures of the continuous or semi-continuous pattern.

In other forms, the apertures, or aperture arrays thereof, in an apertured web may form linear patterns alternating with continuous or semi-continuous land areas. The apertured webs may include unidirectional or multi-directional (and intersecting) aperture or aperture array patterns. Linear aperture or array patterns may be oriented parallel to the longitudinal or lateral axis, or at an angle between 0 and 90 degrees, specifically reciting all 0.5 degree increments within the specified range and all ranges formed therein, from either the longitudinal or lateral axis. Linear apertures or aperture array patterns may function to restrict fluid movement along the apertured web to a greater degree in one direction compared to another direction.

Additional examples of apertures or arrays thereof in a patterned web are shown in FIGS. 40-53. A patterned web 1000 may comprise an array of apertures comprising a plurality of patterns 1110A and 1110B with continuous or semi-continuous land areas. As shown, a first pattern 1110A may comprise a first plurality of apertures which are oriented in a direction which is generally parallel to a machine direction 1675 as well as a second plurality of apertures which are oriented at multiple angles with respect to the machine direction. Similarly, a second pattern 1110B may comprise a third plurality of apertures which are oriented at multiple angles with respect to the machine direction 1675 as well as a fourth plurality of apertures which are generally parallel to the machine direction 1675. As shown, the apertures of the first pattern 1110A and/or the second pattern 1110B may be of different lengths, different angles with respect to the machine direction 1675, and/or different Effective Aperture AREAs. Effective Aperture Areas are discussed hereafter.

Additionally, at least one or a plurality of apertures in the first pattern 1110A may be substantially enclosed by the second pattern 1110B, e.g. third plurality of apertures and fourth plurality of apertures. For example, the second pattern may form a quilt like pattern, e.g. diamond shaped boundaries or any other suitable shape, with the first pattern disposed within the second pattern thereby forming a unit. The combination of the first pattern and the second pattern may repeat so that there are a plurality of units. Additionally, the first pattern within the second pattern may be different from one unit to the next. Additional patterns may be utilized. The apertures angled with respect to the machine direction 1675 are believed to aid in fluid acquisition/distribution. For example, fluid moving along the patterned web 1164 in the machine direction 1675 may be diverted, in part, because of the angled apertures.

Referring to FIGS. 39-53, as noted previously, the first pattern 1110A and/or the second pattern 1110B may comprise a plurality of apertures of which at least a portion are angled with respect to the machine direction 1675 at a first angle 1680 and another portion are angled with respect to the machine direction at a second angle 1682. The first angle 1680 and the second angle 1682 may be different from one another. In some forms, the second angle 1682 may be the mirror image of the first angle 1680. For example, the first angle may be about 30 degrees from an axis parallel to the machine direction 1675 while a second angle is −30 degrees from the axis parallel to the machine direction 1675. Similarly, the first pattern 1110A and/or the second pattern 1110B may comprise a plurality of apertures which are oriented generally parallel to the machine direction 1675. As mentioned previously, apertures which are oriented generally parallel to the machine direction 1675 generally have a lower aspect ratio (discussed hereafter) and larger Effective Aperture AREA (described hereafter) as opposed to those apertures which are angled with respect to the machine direction 1675. It is believed that those apertures with increased Effective Aperture AREA allow for quicker fluid acquisitions time. While any suitable angle may be utilized, as discussed hereafter, once the first angle 1680 and the second angle 1682 are increased beyond 45 degrees from the machine direction 1675 (−45 in the case of the second angle 1682), the forces of the cross-direction 1677 stretching act more along a long axis of the aperture than perpendicular thereto. So, apertures which are angled more than 45 degrees with respect to the machine direction 1675 (−45 degrees in the case of the second angle 1682) typically comprise less Effective Aperture AREA than those which are angled to a lesser extent with respect to the machine direction 1675.

As stated previously, the angled apertures are believed to provide additional fluid handling benefits for the patterned web 1164. In some forms, greater than about 10 percent of the apertures are angled with respect to the machine direction 1675. Additional forms are contemplated where greater than about 20 percent, greater than about 30 percent, greater than about 40 percent, greater than about 50 percent, greater than about 60 percent, greater than about 70 percent, greater than about 80 percent and/or less than 100 percent, less than about 95 percent, less than about 90 percent, less than about 85 percent of the apertures are angled with respect to the machine direction 1675 including any number or any ranges encompassed by the foregoing values.

Referring to FIGS. 40-53, the population density of apertures may be greater nearer a centerline 1690 of the patterned web 1000. For example, interaperture distance between adjacent apertures near the centerline 1690 may be a first distance while interaperture distance between adjacent apertures further away from the centerline 1690 may be a second distance. The first distance may be less than the second distance. As an example, interaperture distance between adjacent apertures can be about 1 mm. As such, the first distance may be about 1 mm while the second distance may be about 5 mm or greater. Additional forms are contemplated where the interaperture distance between adjacent apertures increases with increasing distance from the centerline. Interaperture distances are discussed further hereafter.

Additionally, in some instances, apertures nearer the centerline 1690 may be angled at the first angle 1680 while apertures further from the centerline 1690 are positioned at the second angle 1682. The first angle 1680 may be greater than the second angle 1682 with respect to the centerline 1690. For, example, the apertures further from the centerline 1690 may be oriented such that they are generally parallel to the centerline 1690 while the apertures positioned closer to the centerline 1690 are angled with respect to the centerline 1690. In some forms, the angle at which apertures are positioned relative to the centerline 1690 may decrease as the distance from the centerline 1690 increases. For example, a first aperture adjacent the centerline 1690 may be oriented at a first angle of 30 degrees with respect to the centerline 1690, while a second aperture 1 mm from the centerline 1690 may be oriented at 20 degrees from the centerline. The apertures positioned furthest away from the centerline 1690 may be generally parallel to the centerline 1690. Additional configurations are contemplated where apertures near the centerline 1690 are angled to a lesser extent than those further from the centerline 1690. In some embodiments, the apertures near the centerline 1690 may be generally parallel to the centerline 1690 while the apertures further from the centerline 1690 are angled with respect to the centerline 1690. Feret angles of apertures are discussed further hereafter.

As stated previously the lengths of the apertures may vary as well. In conjunction with being angled as disclosed above or independently therefrom, in some embodiments, the apertures adjacent the centerline 1690 may be longer than those which are further away from the centerline 1690. Similarly, the size of the apertures may vary. Variances in aperture size (Effective Aperture AREA) may be employed in conjunction with the variation of aperture angle and/or the variation in aperture length, or variances in aperture size may be employed independently of the variation of aperture angle and/or variation in aperture length. For those embodiments where aperture size may vary, larger apertures may be positioned adjacent the centerline 1690 while apertures having a smaller Effective Aperture AREA are positioned further away from the centerline 1690. For example, apertures adjacent the centerline 1690 may have an Effective Aperture AREA of 15 square millimeters while apertures further away from the centerline may have less Effective Aperture AREA, e.g. 1.0 square mm. Any of the values/ranges of Effective Aperture AREA provided herein may be utilized for configuring the Effective Aperture AREA variance described above.

As mentioned previously, the angle of orientation of the aperture can impact the fluid handling capabilities of the apertured web 1164. Moreover, length of the aperture, width of the aperture, Effective Aperture AREA, spacing between apertures, as well as aperture density can similarly impact fluid handling. However, many of length of apertures, width of apertures, angle of orientation, spacing and density can have competing/negative impacts on the other variables. As stated previously, apertures which are at a greater angle to the machine direction 1675 tend to open less and therefore have less Effective Aperture AREA than apertures which are either parallel to the machine direction 1675 or which have a smaller angle with respect to the machine direction 1675. Similarly, angled apertures which are too closely spaced together tend to open less and therefore have less Effective Aperture AREA. As such, Interaperture distance between adjacent angled apertures may be increased over that which is between apertures which are generally oriented parallel to the machine direction 1675.

Coordinated Patterns

The array of apertures in an apertured web of the present invention may comprise a pattern or a plurality of patterns which form graphics and/or other depictions, hereafter, "apertured indicia." The apertured indicia may coordinate with graphics, indicia, printing, inks, color, and/or patterned adhesives, for example, located beneath the apertured web or within the apertured web. In an instance, the apertured web may be used a topsheet, an outer cover, an ear, or other portion of an absorbent article. Each of the heretofore mentioned indicia may be visible from a wearer-facing surface, e.g. topsheet, of a disposable absorbent article. In some forms, the heretofore mentioned indicia may be visible from a garment-facing surface, e.g. backsheet, of a disposable absorbent article. Still in other forms, the heretofore mentioned indicia may be visible from both the wearer-facing and garment-facing surfaces of a disposable absorbent article.

The aperture pattern in an apertured web may coordinate with features under it, such as bond sites, material edges, channels, and/or discolored or colored materials. In some specific executions, the apertured web may be used to accentuate or block/hide these features. The aperture patterns of a apertured web may also be used to indicate the correct front vs. rear, left vs. right orientation of an absorbent article or other consumer product.

Forms are contemplated where the apertured indicia is coordinated with printed indicia elsewhere on the product and/or packaging. For example, comprise disposable absorbent article of the present invention may comprise apertured indicia which provides the appearance of a snowflake. The feminine article may additionally comprise printed indicia elsewhere on the feminine article itself and/or its packaging, wherein the printed indicia provides the appearance of a snowflake. In such embodiments, the feminine article may comprise a release liner which includes a printed snowflake pattern and/or be placed in a package comprising a printed snowflake pattern.

Forms are contemplated where the apertured indicia is coordinated with adhesive indicia, bond indicia, and/or structural indicia. Embodiments are contemplated where at least two of the following are coordinated on an absorbent article: apertured indicia, adhesive indicia, printed indicia, bond indicia, structural indicia. Similar embodiments are contemplated with regard to the packaging for the disposable absorbent articles described herein (including release liners and/or secondary packaging). Additionally, the aforementioned indicia may be coordinated across the absorbent article, its packaging, and/or its secondary packaging (including release liners) or any combination thereof.

In some specific forms of the present invention, while a portion of the topsheet may include apertured indicia, other portions of the topsheet—the non-apertured portion(s)—may include printed indicia which is coordinated with the apertured indicia. In other embodiments, a sub-layer, e.g. acquisition layer, secondary topsheet, and/or absorbent core may comprise printed indicia which is coordinated with the apertured indicia of the topsheet. Still in other embodiments, the backsheet may comprise printed indicia which is coordinated with the apertured indicia of the topsheet. Forms are contemplated where a portion of the topsheet includes apertured indicia, the backsheet includes printed indicia coordinated with the apertured indicia, packaging of the feminine article includes printed indicia coordinated with the apertured indicia, a non-apertured portion of the topsheet includes printed indicia which is coordinated with the apertured indicia and/or a sub-layer, e.g. acquisition layer, secondary topsheet, and/or absorbent core comprise printed indicia which is coordinated with the apertured indicia. Similar embodiments are contemplated with adhesive indicia, structural indicia, bond indicia, and/or any combinations thereof.

In other specific forms, the topsheet may comprise apertured indicia and first printed indicia. The first printed indicia may coordinate with printed indicia on secondary packaging while apertured indicia may coordinate with printed indicia on primary packaging for the absorbent article.

Indicia is visually coordinated when one or more elements of the indicia have two or more visual characteristics that are either matched or are caused to match. As used herein, the term "match" or "matched" is used to describe the way or degree to which apertured indicia, printed indicia, bond indicia, adhesive indicia, and/or structural indicia, or characteristics thereof visually fit together or are caused to fit together. For example, apertured indicia and printed indicia are considered matched if some aspects of the apertured indicia are identical to similar aspects of the printed indicia. In one form of match, for example, apertured indicia and printed indicia that resemble each other are said to match. The same can be true for any combination of the heretofore mentioned indicia. As used herein, the term "coordinate" or "coordination" is used to describe how indicia of the overall absorbent article and/or its packaging visually belong together. Components or elements are considered to be coordinated if they match, or are caused to match. As used herein, the term "caused to match" is used to describe how any combination of aforementioned indicia are made to appear matched to one another by using coordinating indicia (any combination of the above) which has a coordinating feature which ties the aforementioned indicia together. For example, if apertured indicia and printed indicia each have a visual characteristic different from one another and coordinating indicia has visual characteristics which match each of the apertured indicia and printed indicia, the coordinating feature causes the apertured indicia and printed indicia to be matched to one another.

Additionally, patterns comprising multiple features may be coordinated. As an example, a first array of apertures may be grouped with adjacent bond sites to form a pattern unit. This pattern unit may be repeating. For example, a first pattern unit may be disposed adjacent a first end of an absorbent article while a second pattern unit is disposed adjacent a second end of an absorbent article. As another example, the first pattern unit may be disposed adjacent a first end of an absorbent article while the second pattern unit is disposed adjacent a transverse axis of the absorbent article. Still another example may comprise additional pattern units which may be disposed in any suitable location on an absorbent article. Pattern units may comprise any combination of features. For example a pattern unit may comprise apertures, bonds, print, structures, or combinations thereof.

Some examples of coordinated indicia include theme related indicia. In some embodiments, indicia described herein may be coordinated where at least two of the indicia, e.g. apertured and printed include at least one of items generally thought of as lucky, e.g. hearts, stars, horseshoes, clovers, moons (printed indicia may include blue moons), pots of gold, rainbows, balloons, and the like or combinations thereof. Other examples of coordinated indicia include numbers, letters, combinations of numbers and letters; winter themes including snowflakes and/or the like; spring themes including flowers, bees, birds, trees, sun, geometric shapes, squares, rectangles, triangles, oval, circles; curves including uni-radial arcs, multi-radial arcs, spirals, truncated sinusoidal waves.

Apertured webs of the present invention may be utilized in multiple areas of the disposable absorbent articles described herein. For example, in some embodiments, an apertured web of the present invention may be utilized as a leg cuff of an absorbent article, a backsheet and/or outer cover, and/or a topsheet. For such embodiments, the array of apertures utilized for the topsheet may be coordinated with the array of apertures utilized for the leg cuffs and/or backsheet. In some embodiments, the array of apertures in the leg cuff may coordinate with the array of apertures for the backsheet but not for the topsheet. In other embodiments, the array of apertures of the backsheet may coordinate with the array of apertures for the topsheet.

If an apertured web is used as part, or all of, an outer cover (garment-facing layer) of an absorbent article, the aperture pattern or patterns may provide enhanced breathability in certain regions (e.g., waist, hips) or reduced breathability in areas over an absorbent core, for example. The aperture pattern or patterns in an apertured web used as an outer cover may also provide enhanced textures and/or signals in certain regions of the outer cover. Such texture and/or signals may provide intuitive instructions on how to property apply the absorbent article, where to grip the absorbent article, and/or where/how to fasten the absorbent article, among other functions, such as to enhance graphics or aesthetics.

If an apertured web is used as a portion of a fastener (e.g., taped fastener) of an absorbent article, an apertured pattern of an apertured web of the fastener may indicate how to grip and fasten the fastener and indicate when it is and is not fastened correctly. An apertured pattern of the apertured web used as a fastener, or portion thereof, may coordinate with an aperture pattern of an apertured web used as a topsheet and/or an outer cover of the same absorbent article to signal a holistic function.

The optimum balance of bodily exudate acquisition speed and rewet in an absorbent article comprising an apertured web as a topsheet and/or topsheet and acquisition system may be derived from a combination of aperture diameter, shape or area, depth or thickness of the apertured web, and the spacing between the various apertures or aperture arrays within the apertured web.

An absorbent article comprising an apertured web as a topsheet and/or a topsheet and an acquisition system may comprise a longitudinal axis, much like the longitudinal axis of 590 of FIG. 29. Arrays of apertures in the apertured web may repeat themselves along a line that is angled about 20 degrees to about 160 degrees, specifically reciting all 1 degree increments within the specified range and all ranges formed therein, relative to the longitudinal axis. Additionally, there may be a plurality of aperture sizes, shapes, or areas along the line or the spacing between the apertures may not the same between all of the apertures along the line for purposes of channeling liquid bodily exudates into preferred areas of the absorbent article or the absorbent core thereof to help avoid leakage.

An aperture pattern in an apertured web may form a recognizable visual element, such as a heart or a water droplet, for example. An aperture pattern that forms one or more water droplet shapes in an apertured web used as a topsheet or an outer cover of an absorbent article may be used to aid communication of absorbency and/or wetness. Such a feature may be combined with a wetness indicator of an absorbent article.

Various commonly understood shapes may be created in an apertured web. These shapes may be shapes that have commonly understood proper orientations, such as hearts, for example. An example is the use of one or more hearts on an outer cover or topsheet of a front waist region and/or a back waist region of a diaper. The caregiver would understand to place the diaper on the wearer with the point of the heart facing toward the wearer's feet because of the common knowledge of the orientation of hearts.

In an instance, an apertured web may comprise a first non-apertured layer comprising a pattern having a color and a second apertured layer comprising a pattern of apertures. The pattern on the first non-apertured layer may be printed on the layer, for example, and may form graphics or other indicia. At least 50% to 100% of the pattern on the first non-apertured layer may be aligned with the pattern of apertures in the second apertured layer to draw attention to the apertures. The alignment, or partial alignment, of the pattern of apertures on the first layer with the pattern having a color of the second layer may make aid in aligning the product on a wearer if the apertured web is provided on an absorbent article.

The apertured indicia, printed indicia, adhesive indicia, bond indicia when used on a topsheet and/or backsheet of a disposable absorbent article, may be utilized to ensure proper alignment of the absorbent article. For example, any one of apertured indicia, printed indicia, adhesive indicia, bond indicia, and/or combinations thereof, may be utilized to highlight proper alignment. In one specific example, printed indicia may be utilized to communicate to a wearer the proper orientation of a feminine hygiene pad. Proper orientation of the feminine hygiene pad can reduce the likelihood of leakage.

Additionally, the apertured indicia, printed indicia, adhesive indicia, bond indicia when used on a topsheet and/or backsheet of a disposable absorbent article may be utilized to highlight features of the absorbent article which would otherwise not be noticeable by simple visual inspection of the article. For example, absorbent cores of disposable absorbent articles are generally disposed between the topsheet and the backsheet. In many instances, upon visual inspection, a wearer may not be able to discern the boundaries of the absorbent core which are typically inboard of the periphery of the absorbent article. In such instances, at least one of apertured indicia, printed indicia, adhesive indicia, bond indicia or any combination thereof, may be utilized to communicate the boundaries of the absorbent core. This may provide some reassurance to the wearer regarding the "zone" of absorbency. Still in other configurations, at least one of apertured indicia, printed indicia, adhesive indicia, bond indicia or any combination thereof, may be utilized to communicate a particular area of the absorbent core. For example, an absorbent article may comprise an absorbent core having variable absorbing capacity. In such instances, at least one of the apertured indicia, printed indicia, adhesive indicia, bond indicia or any combination thereof, may be utilized to highlight an area of the core having higher absorbing capacity than other areas. Conversely, apertured indicia, printed indicia, adhesive indicia, bond indicia or any combination thereof, may be utilized to highlight those portions of the absorbent core which have lower capacity than another portion of the absorbent core. Still other executions are contemplated where a first array of apertured indicia, printed indicia, adhesive indicia, bond indicia or any combination thereof is utilized to communicate to the wearer a portion of the absorbent core having higher absorbing capacity than other portions while a second array of apertured indicia, printed indicia, adhesive indicia, bond indicia or any combination thereof are used to communicate to the wearer regarding other portions of the absorbent core having lower absorbing capacity. In such executions, the first array and the second array may or may not be coordinated.

Zones

In any context of an apertured web, but especially in an absorbent article context, the apertured webs may be employed in a zonal fashion. For instance, a first zone of a topsheet of an absorbent article may have a first apertured web having a first pattern, while a second zone of a topsheet of an absorbent may have a second apertured web having a second, different pattern. The patterns in the different zones may be configured to receive certain bodily exudates or inhibit or encourage their flow in any desired direction. For example, the first pattern may be better configured to receive and/or direct the flow of urine, while the second pattern may be better configured to receive and/or direct the flow of runny BM. In other instances where the apertured webs are used as a topsheet of an absorbent article, a first apertured web having a first pattern may be configured to receive heavy gushes of bodily exudates while a second apertured web having a second different pattern may be configured to restrict lateral bodily exudate flow in any desired direction. The first pattern may be situated in, for instance, the middle of the absorbent article or in the crotch region, while the second pattern may be situated in the front and rear waist regions or outer perimeter topsheet regions of the absorbent article.

The zones in an apertured web may be positioned in the machine direction, the cross direction, or may be concentric. If a product, such as an absorbent article, has two different zones in the machine direction, the zones may have the same or a similar cross-direction width (e.g., +/−2 mm) for ease in processing. One or more of the zones may have curved or straight boundaries or partial boundaries.

Any suitable zones, including more than two, of different or the same apertured webs are envisioned within the scope of the present disclosure. The various zones may be in the topsheet as mentioned above, but may also be present on an outer cover or a cuff for example. In some instances, the same or a different pattern of zones of apertured webs may be used on the wearer-facing surface (e.g., topsheet) and the garment-facing surface (e.g., outer cover).

In an instance, a topsheet or other portion of an absorbent article may have two or more zones in an apertured web. A first zone of the apertured web may have a different aperture pattern than a second zone. The first zone and the second zone may have different functionalities owing to the different aperture patterns. A functionality of the first zone may be to provide liquid bodily exudate distribution (fluid moving on the apertured web), while the functionality of the second zone may be to provide liquid bodily exudate acquisition (fluid penetrating the apertured web). Benefits of such a zoned apertured web can be better use of an absorbent core and more efficient liquid bodily exudate distribution within the absorbent core. This is especially important if an air-felt free core is used in that typical air-felt free cores may distribute liquid bodily exudates to a lesser extent.

In an instance, an absorbent article may comprise an apertured web that forms a first portion and a second, different portion thereof. Aperture patterns in each portion of the apertured web may be the same, substantially similar, or different. In another instance, an absorbent article may comprise an apertured web that comprises a first portion of an absorbent article, and wherein a second portion of the absorbent article has graphics, printing, patterned adhesives, or other indicia that forms a pattern that is similar to, substantially similar to, coordinates with, or is different than an aperture pattern in the apertured web.

In an instance, an apertured web may have a plurality of zones. A first zone may have at least some apertures having a first angle (central longitudinal axis of aperture vs. MD), first size, and/or first shape, while a second zone (or third or fourth zone etc.) may have apertures having a second, different angle (central longitudinal axis of aperture vs. MD), second, different size, and/or second, different shape.

Figure 54:
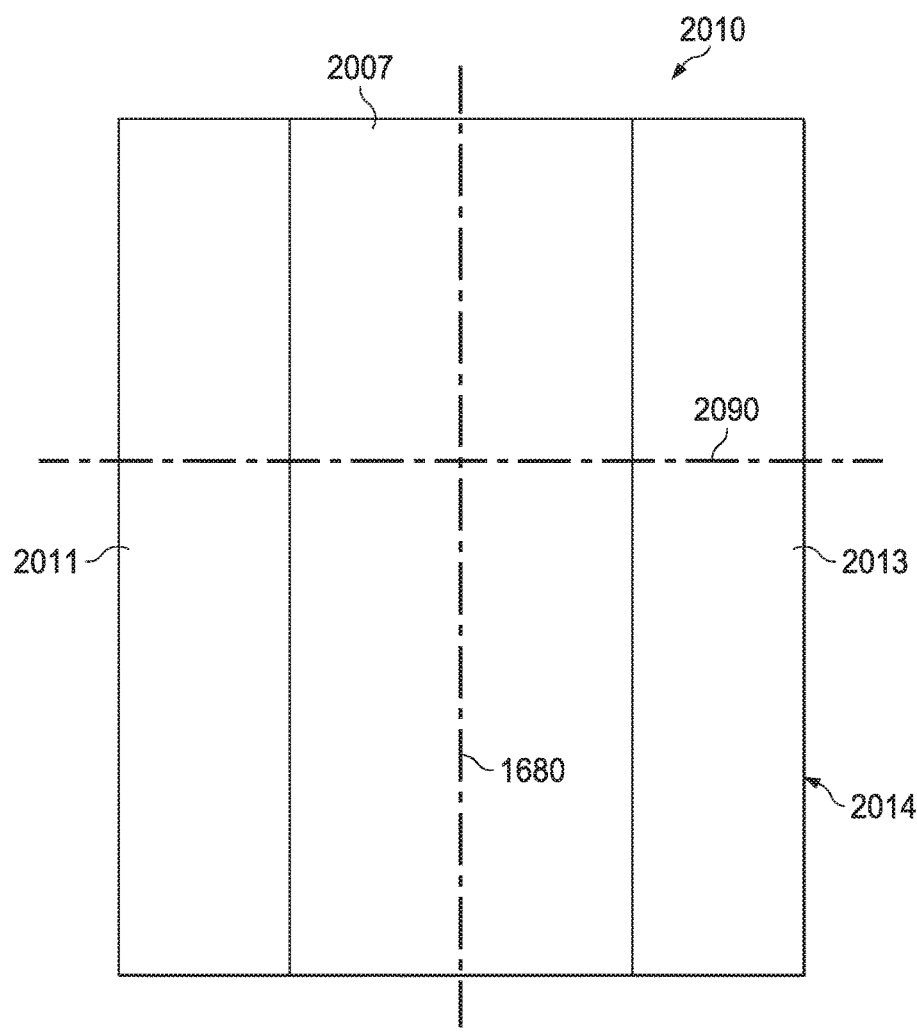
FIGS. 54-58 represents a schematic illustration of a disposable absorbent article comprising a plurality of zones in accordance with the present invention.

As stated previously, the apertured webs of the present invention may be utilized in a number of different components of absorbent articles. Referring to FIG. 54, in one specific example, disposable absorbent articles utilizing the apertured web of the present invention may comprise a plurality of zones. As shown, a topsheet 2014 of a disposable absorbent article 2010, may comprise a first zone 2007, a second zone 2011 and a third zone 2013. Absorbent articles may comprise more zones or less zones as described hereafter.

The first zone 2007 may comprise an array of apertures as described herein. As shown the first zone 2007 may have a width parallel to a lateral axis 2090 which does not extend the full width of the topsheet 2014. Instead, the second zone 2011 and the third zone 2013 may be placed on either side of the first zone 2007. In some embodiments, the second zone 2011 and the third zone 2013 may comprise a first array of structures and a second array of structures, respectively. For these embodiments, the array of apertures in the first zone 2007 may form apertured indicia which may be coordinated with the array of structures in the second zone 2011 and/or the array of structures in the third zone 2013. In a specific execution, the first zone 2007 comprises an array of apertures, the second and third zones 2011 and 2013, respectively, comprise an array of structures, wherein the array of structures in both the second zone 2011 and the third zone 2013 comprise tufts 1770 oriented in the Z-direction or negative Z-direction.

Still in other forms, the first zone 2007 may comprise an array of structures while the second zone 2011 and the third zone 2013 comprise a first array of apertures and a second array of apertures, respectively. In such embodiments, the array of structures may be coordinated with the array of apertures in the second zone 2011 and the third zone 2013.

In some forms, the first zone 2007 may comprise the array of apertures as well as an array of bonds. The bonds, as mentioned previously, may be configured to provide bond indicia. In some embodiments, bond indicia may be coordinated with the apertured indicia in the first zone 2007. In other embodiments, bond indicia may be present, in addition to the first zone 2007, in the second zone 2011 and/or third zone 2013. In such embodiments, the bond indicia may be coordinated with the apertured indicia in the first zone 2007 or may be un-coordinated with respect to the apertured indicia. Adhesive indicia, printed indicia may similarly be provided in the first zone 2007, the second zone 2011, and/or the third zone 2013. In such embodiments, the adhesive indicia, printed indicia may be coordinated with the apertured indicia or may be un-coordinated with the apertured indicia. In a specific execution, the first zone 2007 comprises an array of apertures forming apertured indicia and an array of bonds forming bond indicia. The second zone 2011 and the third zone 2013 may each comprise an array of structures, wherein the array of structures comprise tufts 1770 oriented in the Z-direction. In such executions, the apertured indicia may be coordinated with bond indicia. In other executions, bond indicia may not be coordinated with apertured indicia.

In some forms, the first zone 2007, the second zone 2011 and/or the third zone 2013 may comprise a plurality of indicia selected from printed indicia, apertured indicia, adhesive indicia, structural indicia, and bond indicia. In such embodiments, any combination of the plurality of indicia may be coordinated with indicia within its respective zone and/or with regard to one of the other or both zones.

Webs without apertures and webs without patterned apertures may similarly comprise variable zones. For example, the first zone 2007 may comprise printed indicia while the second zone 2011 and the third zone 2013 comprise structural indicia. The printed indicia and the structural indicia may be coordinated. In other examples, the first zone 2007 may comprise adhesive indicia while the second and the third zones 2011 and 2013, respectively, comprise structural indicia. The adhesive indicia may be coordinated with the structural indicia. In yet another example, the first zone 2007 may comprise bond indicia while the second zone 2011 and third zone 2013 comprise structural indicia. The bond indicia may be coordinated with the structural indicia. Still in other forms, the first zone 2007 may comprise apertured indicia and printed indicia while the second zone 2011 and the third zone 2013 comprise structural indicia. The structural indicia may be coordinate with the apertured indicia which in turn may be coordinated with the printed indicia.

Other suitable configurations of zones are described with regard to FIGS. 54-58. FIGS. 54-58 may represent a portion of a wearer-facing surface of an absorbent article, such as a diaper, an adult incontinence product, and/or a sanitary napkin.

Figure 55:
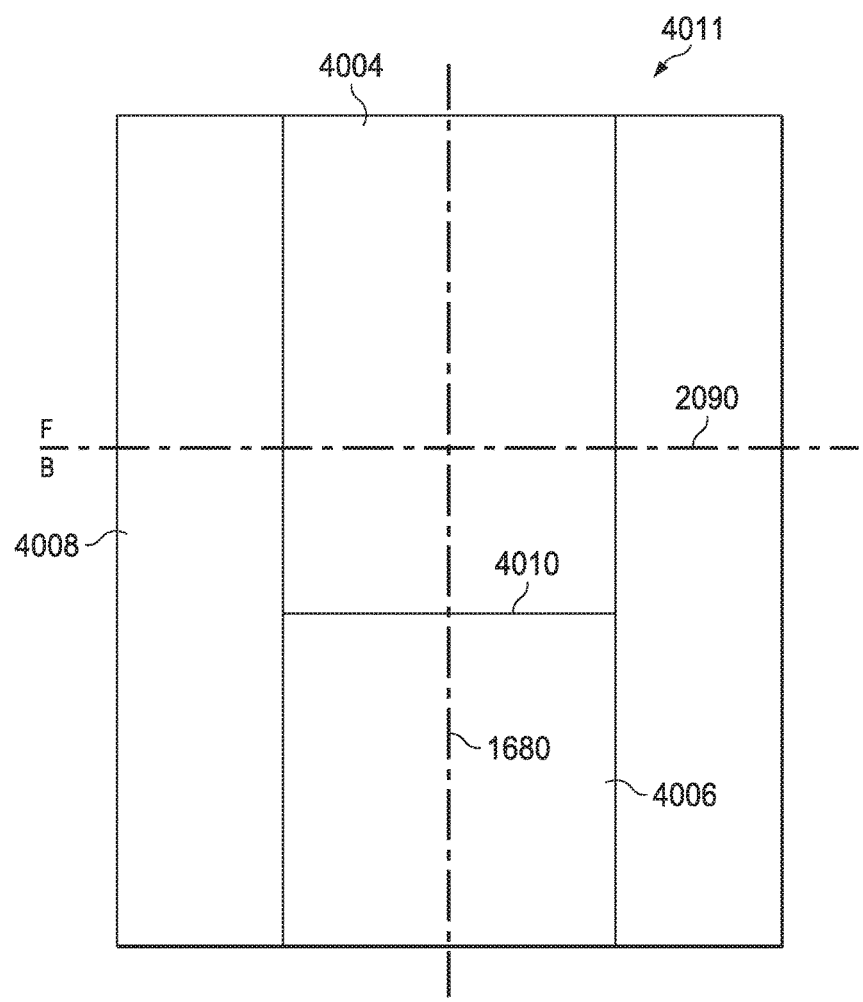

FIG. 55 illustrates an example of a substrate having three zones. The front portion, F, may be positioned in a front portion of an absorbent article or a back portion of an absorbent article. The back portion, B, may be positioned in a front portion of an absorbent article or a back portion of an absorbent article. A first zone 4004 and a second zone 4006 may be positioned intermediate two portions of the third zone 4008. The zones 4004, 4006, and 4008 may be provided as separate pieces of material that are partially overlapped and joined or bonded together or may be provided as one piece of material. In an instance, the first zone 4004 and the second zone 4006 may be provided as one piece of material or as two pieces of material that partially overlapped and joined or bonded together.

The first zone 4004 may comprise a plurality of three-dimensional protrusions as described above with reference to FIGS. 2A-9B. The three-dimensional protrusions may extend upwardly out of the page or downwardly into the page. The second zone 4006 may comprise a plurality of three-dimensional protrusions as described above with reference to FIGS. 38A-38B. The three-dimensional protrusions may extend upwardly out of the page or downwardly into the page. The second zone 4006 may have a different or the same pattern, shape, size, and/or orientation of the three-dimensional protrusions compared to the pattern, shape, size, and/or orientation of the first zone 4004. The third zone 4008 may comprise a pattern of apertures, wherein at least two apertures of the pattern of apertures have different sizes, shapes, and/or orientations. The pattern of apertures may be any of the various patterns described herein or other suitable patterns. A substantially-laterally extending separation element, 4010, may extend between the intersection of the first zone 4004 and the second zone 4006.

In another instance, still referring to FIG. 55, the first zone 4004 may comprise a pattern of apertures, wherein at least two apertures of the pattern of apertures have different sizes, shapes, and/or orientations. The pattern of apertures may be any of the various patterns described herein or other suitable patterns. The second zone 4006 may comprise a pattern of apertures, wherein at least two apertures of the pattern of apertures have different sizes, shapes, and/or orientations. The pattern of apertures may be any of the various patterns described herein or other suitable patterns. The second zone 4006 may have a different or the same pattern of apertures as the first zone 4004. The third zone 4008 may comprise a plurality of three-dimensional protrusions as described above with reference to FIGS. 2A-9B. The three-dimensional protrusions may extend upwardly out of the page or downwardly into the page. A substantially-laterally extending separation element, 4010, may extend between the intersection of the first zone 4004 and the second zone 4006.

Figure 56:
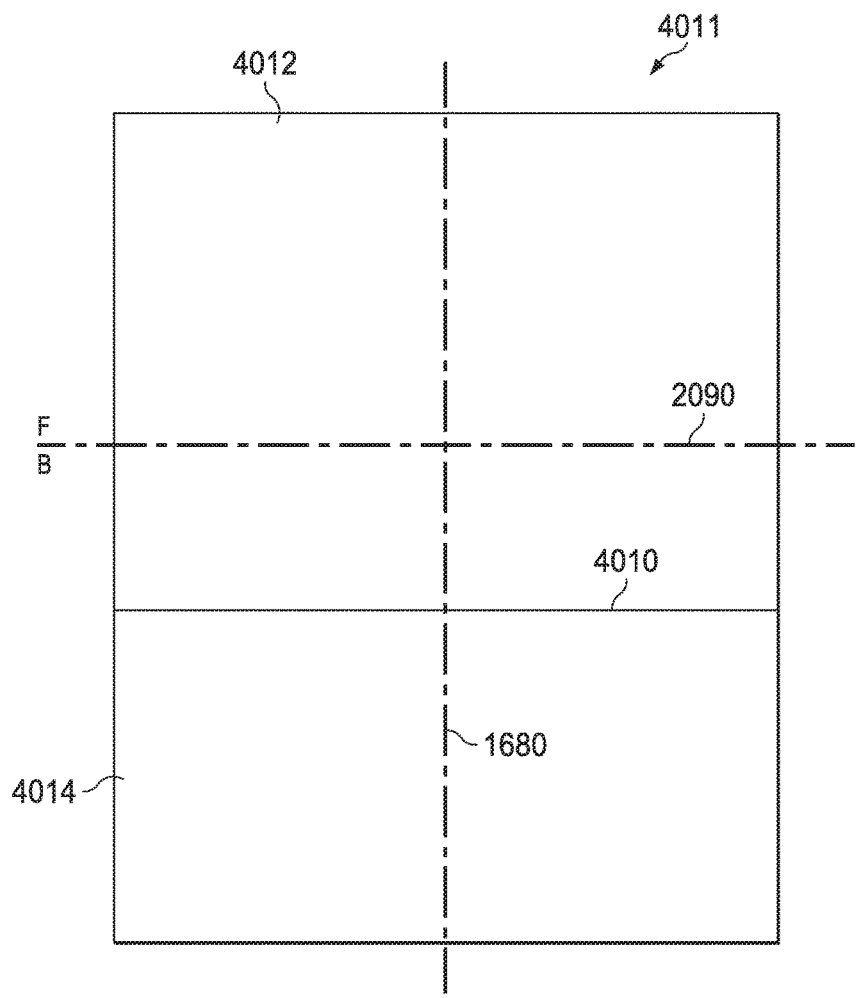

FIG. 56 illustrates an example of a substrate having a first zone 4012 and a second zone 4014. The front portion, F, may be positioned in a front portion of an absorbent article or a back portion of an absorbent article. The back portion, B, may be positioned in a front portion of an absorbent article or a back portion of an absorbent article. The zones 4012 and 4014 may be provided as two separate pieces of material that are partially overlapped and joined or bonded together or may be provided as one piece of material. The first zone 4012 may comprise a pattern of apertures, wherein at least two apertures of the pattern of apertures have different sizes, shapes, and/or orientations. The pattern of apertures may be any of the various patterns described herein or other suitable patterns. The second zone 4014 may comprise a plurality of three-dimensional protrusions as described above with reference to FIGS. 2A-9B. The three-dimensional protrusions may extend upwardly out of the page or downwardly into the page. A substantially-laterally extending separation element, 4010, may extend between the intersection of the first zone 4012 and the second zone 4014.

In another instance, still referring to FIG. 56, the second zone 4014 may comprise a pattern of apertures, wherein at least two apertures of the pattern of apertures have different sizes, shapes, and/or orientations. The pattern of apertures may be any of the various patterns described herein or other suitable patterns. The first zone 4012 may comprise a plurality of three-dimensional protrusions as described above with reference to FIGS. 38A-38B. The three-dimensional protrusions may extend upwardly out of the page or downwardly into the page. A substantially-laterally extending separation element, 4010, may extend between the intersection of the first zone 4012 and the second zone 4014.

Figure 57:
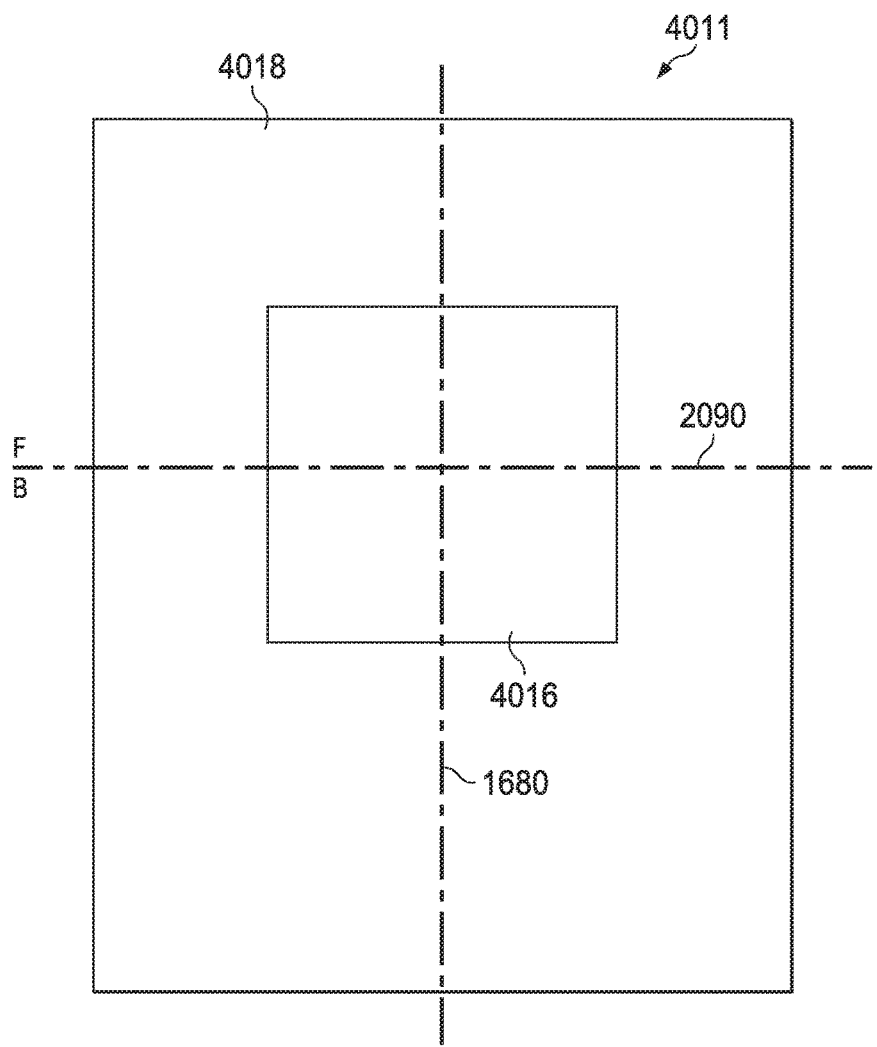

FIG. 57 illustrates an example of a substrate having a first zone 4016 and a second zone 4018. The front portion, F, may be positioned in a front portion of an absorbent article or a back portion of an absorbent article. The back portion, B, may be positioned in a front portion of an absorbent article or a back portion of an absorbent article. The zones 4016 and 4018 may be provided as two separate pieces of material that are partially overlapped and joined or bonded together or may be provided as one piece of material. The second zone 4018 may at least partially, or fully, surround the first zone 4016.

Still referring to FIG. 57, the first zone 4016 may comprise a plurality of three-dimensional protrusions as described above with reference to FIGS. 2A-9B. The three-dimensional protrusions may extend upwardly out of the page or downwardly into the page. The second zone 4018 may comprise a plurality of three-dimensional protrusions as described above with reference to FIGS. 38A-38B. The three-dimensional protrusions may extend upwardly out of the page or downwardly into the page. The second zone 4018 may have a different or the same pattern, shape, size, and/or orientation of the three-dimensional protrusions compared to the pattern, shape, size, and/or orientation of the first zone 4016.

In another instance, still referring to FIG. 57, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a plurality of three-dimensional protrusions as described above with reference to FIGS. 38A-38B. The three-dimensional protrusions may extend upwardly out of the page or downwardly into the page.

In yet another instance, still referring to FIG. 57, the second zone 4018 may comprise a pattern of apertures, wherein at least two apertures of the pattern of apertures have different sizes, shapes, and/or orientations. The pattern of apertures may be any of the various patterns described herein or other suitable patterns. The first zone 4016 may comprise a plurality of three-dimensional protrusions as described above with reference to FIGS. 38A-38B. The three-dimensional protrusions may extend upwardly out of the page or downwardly into the page.

In another instance, still referring to FIG. 57, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4016 and the second zone 4018 may be different or the same.

Figure 58:
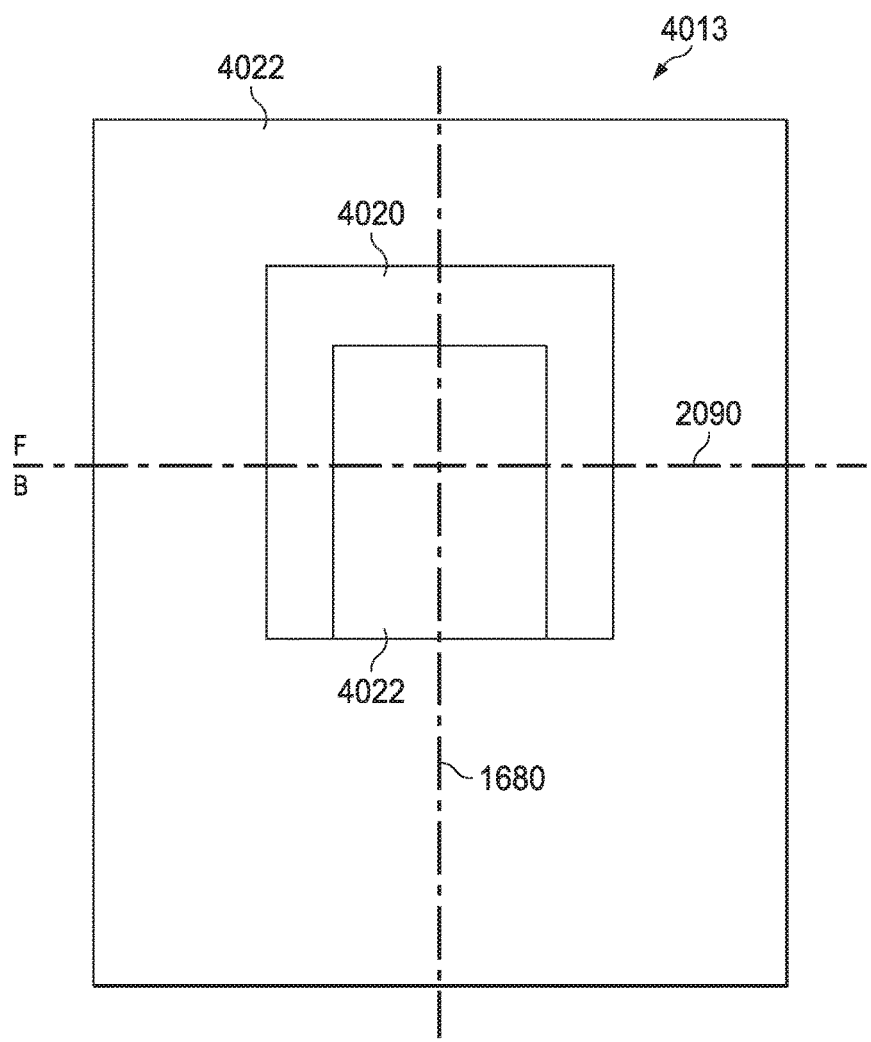
Figure 59:
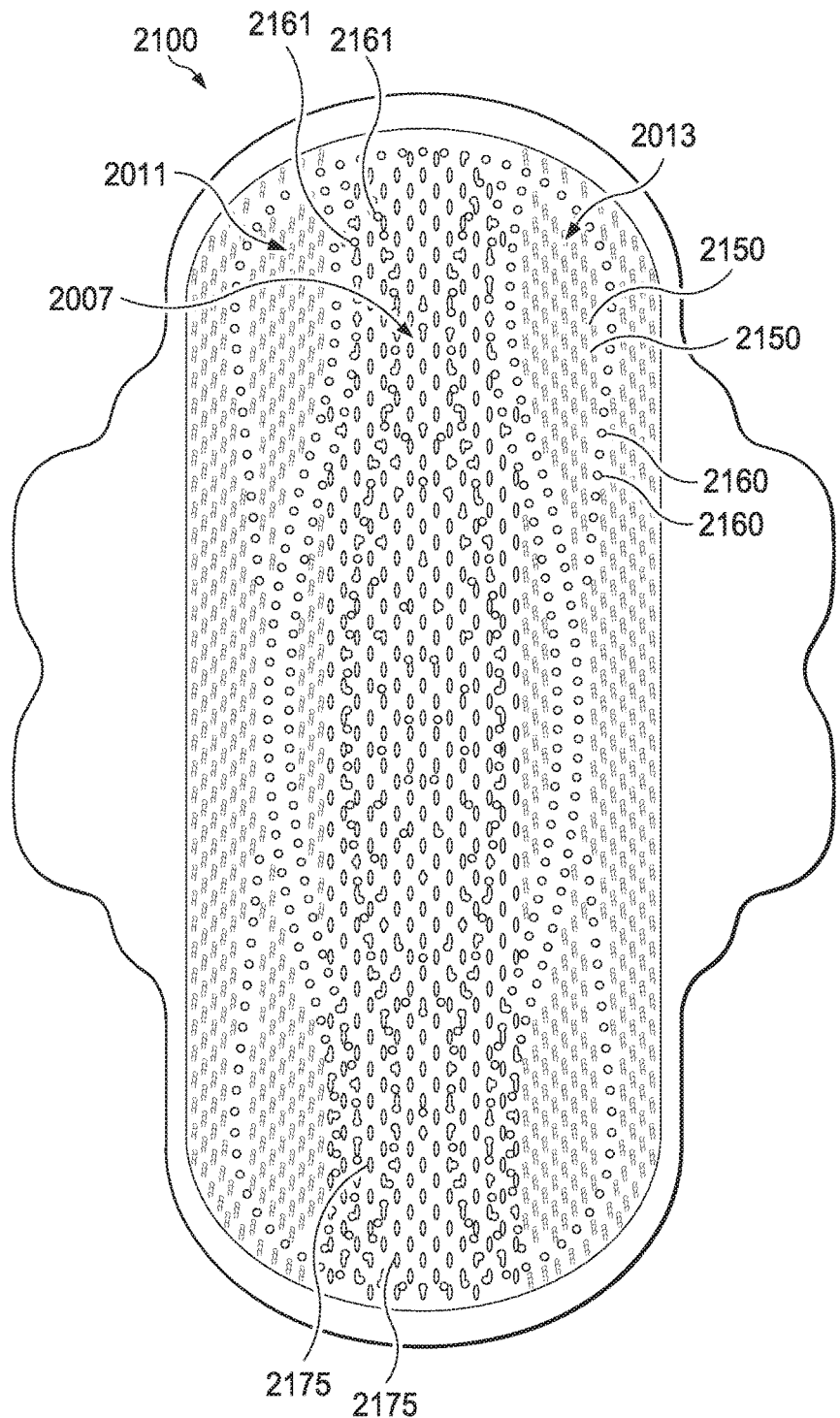
FIGS. 59-65 represent schematic illustrations of feminine care articles constructed in accordance with the present invention and including the apertured webs described herein.
Figure 60:
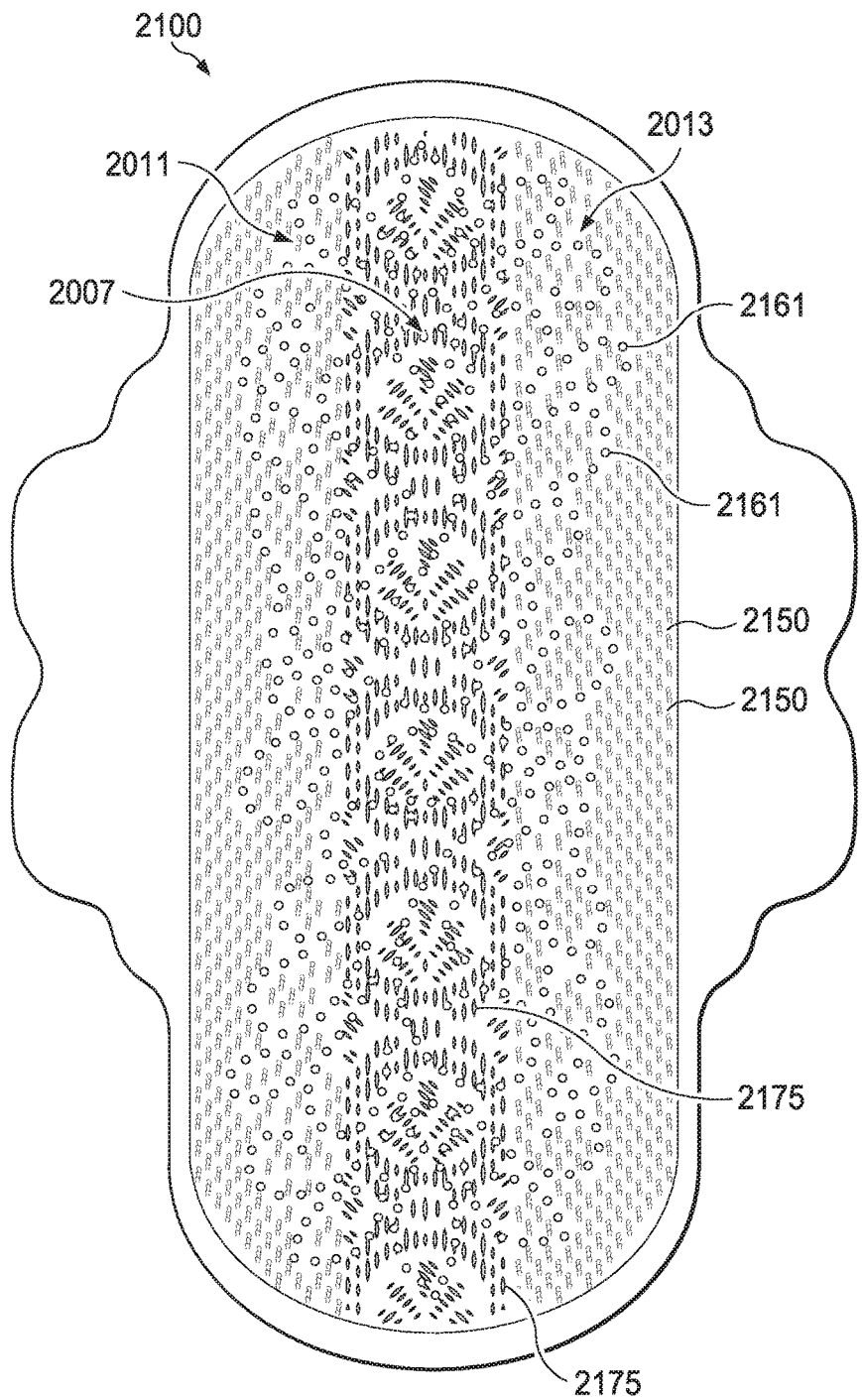

FIG. 58 illustrates an example of a substrate having a first zone 4020 and a second zone 4022. The front portion, F, may be positioned in a front portion of an absorbent article or a back portion of an absorbent article. The back portion, B, may be positioned in a front portion of an absorbent article or a back portion of an absorbent article. The zones 4020 and 4022 may be provided as two separate pieces of material that are partially overlapped and joined or bonded together or may be provided as one piece of material. The second zone 4022 may at least partially, or fully, surround the first zone 4020.

Still referring to FIG. 58, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4020 and the second zone 4022 may be different or the same.

Still referring to FIG. 58, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a plurality of three-dimensional protrusions as described above with reference to FIGS. 38A-38B. The three-dimensional protrusions may extend upwardly out of the page or downwardly into the page Still referring to FIG. 58, the second zone 4022 may comprise a pattern of apertures, wherein at least two apertures of the pattern of apertures have different sizes, shapes, and/or orientations. The pattern of apertures may be any of the various patterns described herein or other patterns. The first zone 4020 may comprise a plurality of three-dimensional protrusions as described above with reference to FIGS. 38A-38B. The three-dimensional protrusions may extend upwardly out of the page or downwardly into the page Still referring to FIG. 58, the first zone 4020 may comprise a plurality of three-dimensional protrusions as described above with reference to FIGS. 38A-38B. The three-dimensional protrusions may extend in a positive Z-direction or in a negative Z-direction. The second zone 4022 may comprise a plurality of three-dimensional protrusions as described above with reference to FIGS. 38A-38B. The three-dimensional protrusions may extend upwardly out of the page or downwardly into the page. The second zone 4022 may have a different or the same pattern, shape, size, and/or orientation of the three-dimensional protrusions compared to the pattern, shape, size, and/or orientation of the first zone 4020.

Some specific examples of absorbent articles comprising zones as described herein are provided with respect to FIGS. 59-65. The disposable absorbent article is in the form of a sanitary napkin 2100 comprising wings. As shown, the second zone 2011 and the third zone 2013 may each comprise an array of structures 2150, e.g. tufts 1770 (shown in FIGS. 38A-38B). Additionally, the second zone 2011 and third zones 2013 may comprise an array of bonds 2160 or a plurality thereof. Similarly, the first zone 2007 may comprise an array of bonds 2161 in addition to an array of apertures 2175. As shown, the array of bonds 2160 in the second zone 2011 and the third zone 2013 may form bond indicia which is coordinated with the bond indicia formed by the array of bonds 2161 in the first zone 2007.

In other executions, the array of bonds 2161 may be comprised in the first zone 2007, second zone 2011, and third zone 2013. In such executions, the array of bonds 2161 may collectively form bond indicia. In addition, an as stated previously, the array of apertures 2175 may form apertured indicia. In some executions, the apertured indicia may be coordinated with the bond indicia. In other executions, the apertured indicia may not be coordinated with the bond indicia.

In some executions, the number of the bonds 2161 in the first zone 2007 adjacent the lateral axis 2090 may be higher than the number of bonds adjacent ends of the sanitary napkin 2100. For example, the sanitary napkin 2100 may comprise an intermediate area 2193, a first end area 2195 and a second end area 2197. Each of the first end area 2195, the second end area 2197, and the intermediate area 2193 are each about ⅓ of the length of the sanitary napkin 2100. The length of the intermediate area 2193 is bisected by the lateral axis 2090, may comprise a higher number of bonds 2161 in the first zone 2007 than in a first end area 2195 and a second end area 2197.

In other executions, the first end area 2195 may comprise a first array of bonds and the second end area 2197 may comprise a second array of bonds. Each of the first array of bonds and the second array of bonds may form bond indicia which may be different than bond indicia formed by a third array of bonds in the intermediate area 2193. The bond indicia in the intermediate zone 2193 may be coordinated with the bond indicia in the first end zone 2195 and/or the bond indicia in the second end zone 2197.

Still in other executions, the bonds 2161 in the first zone 2007 may comprise bond sites which resemble dots and/or shaped bond sites 2163, 2165 which resemble hearts. The bond sites of the bonds 2161 and/or 2160 may be shaped in any suitable manner. Any suitable shapes for shaped bond sites 2163, 2165 can be used. Some suitable examples of shapes for the shaped bond sites 2163 and 2165 include hearts, short lines (dashes), ovals, stars, bows, flowers, squares, triangles, the like, and combinations thereof. As shown, the shaped bond sites 2163, 2165 may be coordinated with apertured indicia formed by apertures 2175. In other executions, a plurality of shaped bond sites 2163, 2165 may form bond indicia. In such executions, the shaped bond sites 2163, 2165 may be coordinated with the bond indicia. Additionally, in such executions, the bond indicia may be coordinated with the apertured indicia. Still in other executions, the shaped bond sites 2163, 2165 may combine with the bond sites to form bond indicia, e.g. a bowtie.

Still referring to FIGS. 59-65, the bond sites disposed in the first end area 2195 in the second zone 2011 and third zone 2013 may be greater than the number of bond sites disposed in the intermediate area 2193. Additionally, the bond sites in the first end area 2195 and the second end area 2197 can curve inward toward their respective ends of the sanitary pad 2100. The second end area 2197 may be configured similarly to the first end area 2195. In such configurations, a width and/or boundary of the first zone 2007 can be masked by the bond sites in the first end area 2195 and the second end are 2197. Specifically referring to FIG. 61, the width of the first zone 2007 appears wider in the intermediate area 2193 than in the first end area 2195 and second end area 2197. That said, the first zone 2007 which can be defined by the apertures (or features as described herein) which are most outboard from a longitudinal axis of the sanitary napkin 2100.

Additionally, this effect can be enhanced by the presence of bond sites in the intermediate area 2193. For example, referring to FIG. 61, bond sites may be disposed in the second zone 2011 and third zone 2013 adjacent a transverse axis of the sanitary pad 2100. However, the bond sites may curve inboard into the first zone 2007 closer to the first end area 2195 and the second end area 2197. This curving of the bond sites in the intermediate area 2193 can also help mask the width of the first zone 2007.

Where the width of the first zone 2007 is defined by the outboard most apertures, the width of the first zone 2007 can be constant from the first end area 2195 to the second end area 2197. The constant width can help preclude unequal strain applied to the web during the stretching process described herein. However, the uniform width of the first zone 2007 creates some difficulty in highlighting the apertures in the intermediate area 2193. So, the above configuration of bond sites can be beneficial in highlighting the apertures in the intermediate area 2193. Such above configurations are believed to be beneficial even where the first zone 2007 does not have a uniform width.

Figure 61:
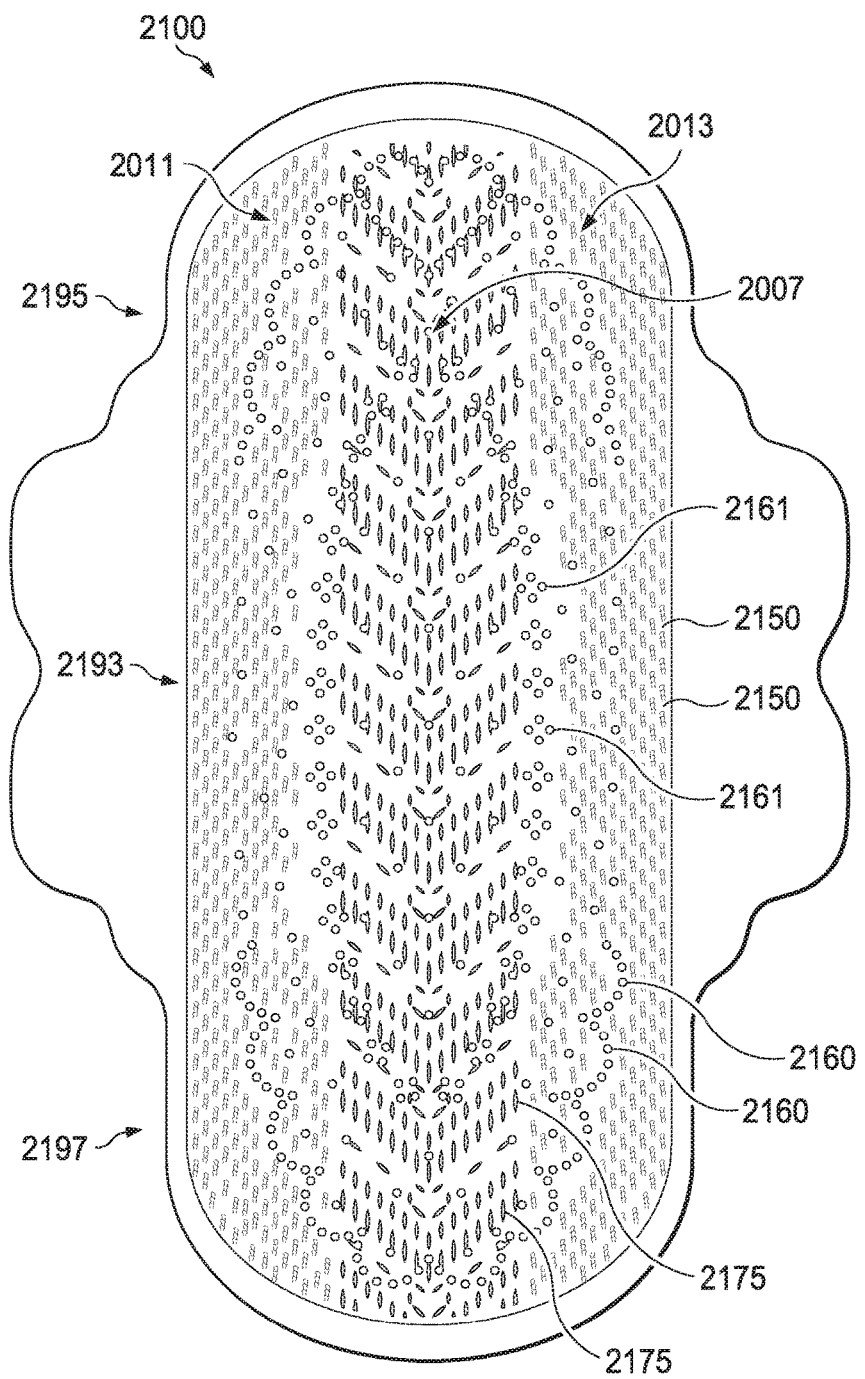
Figure 62:
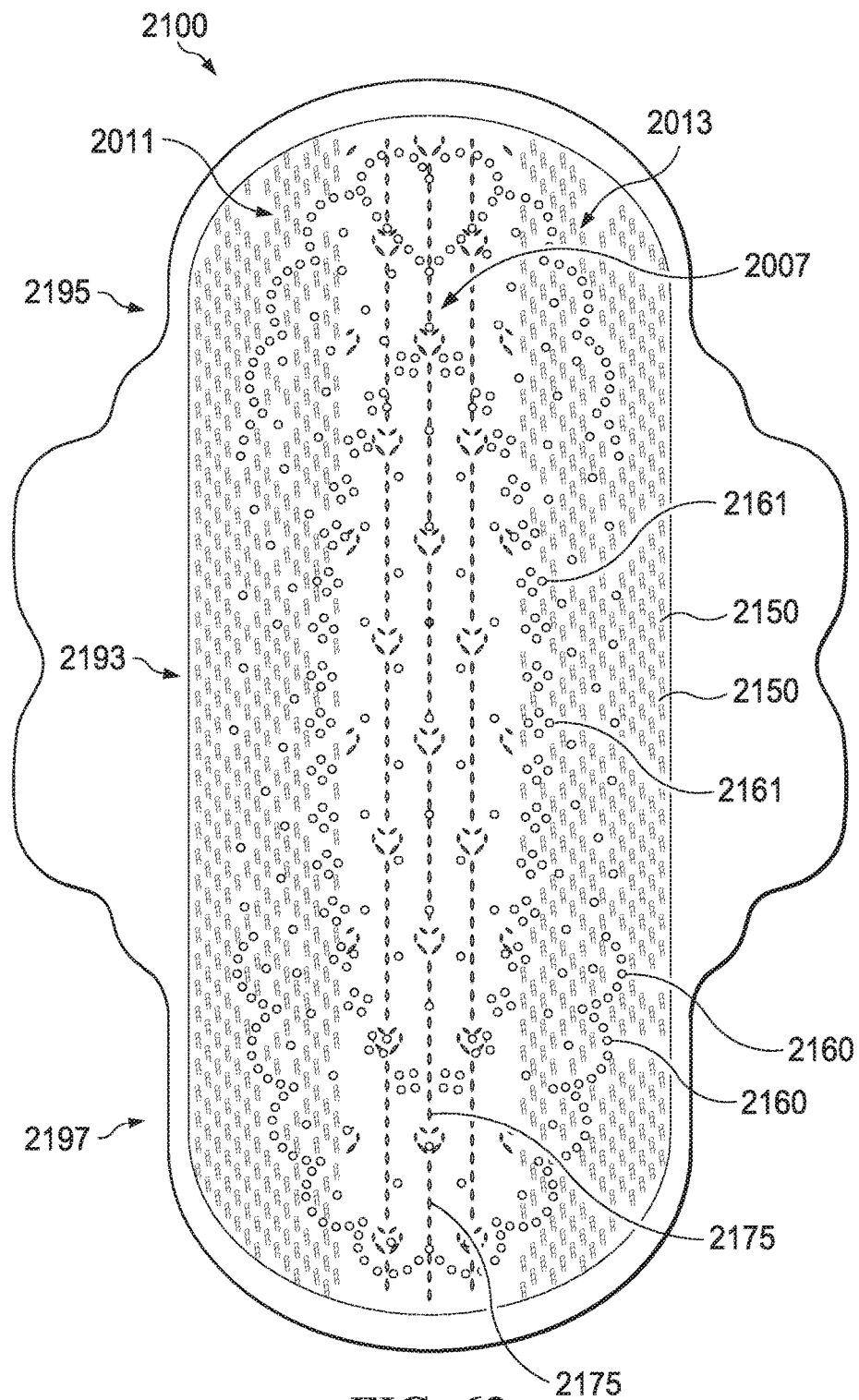
Figure 63:
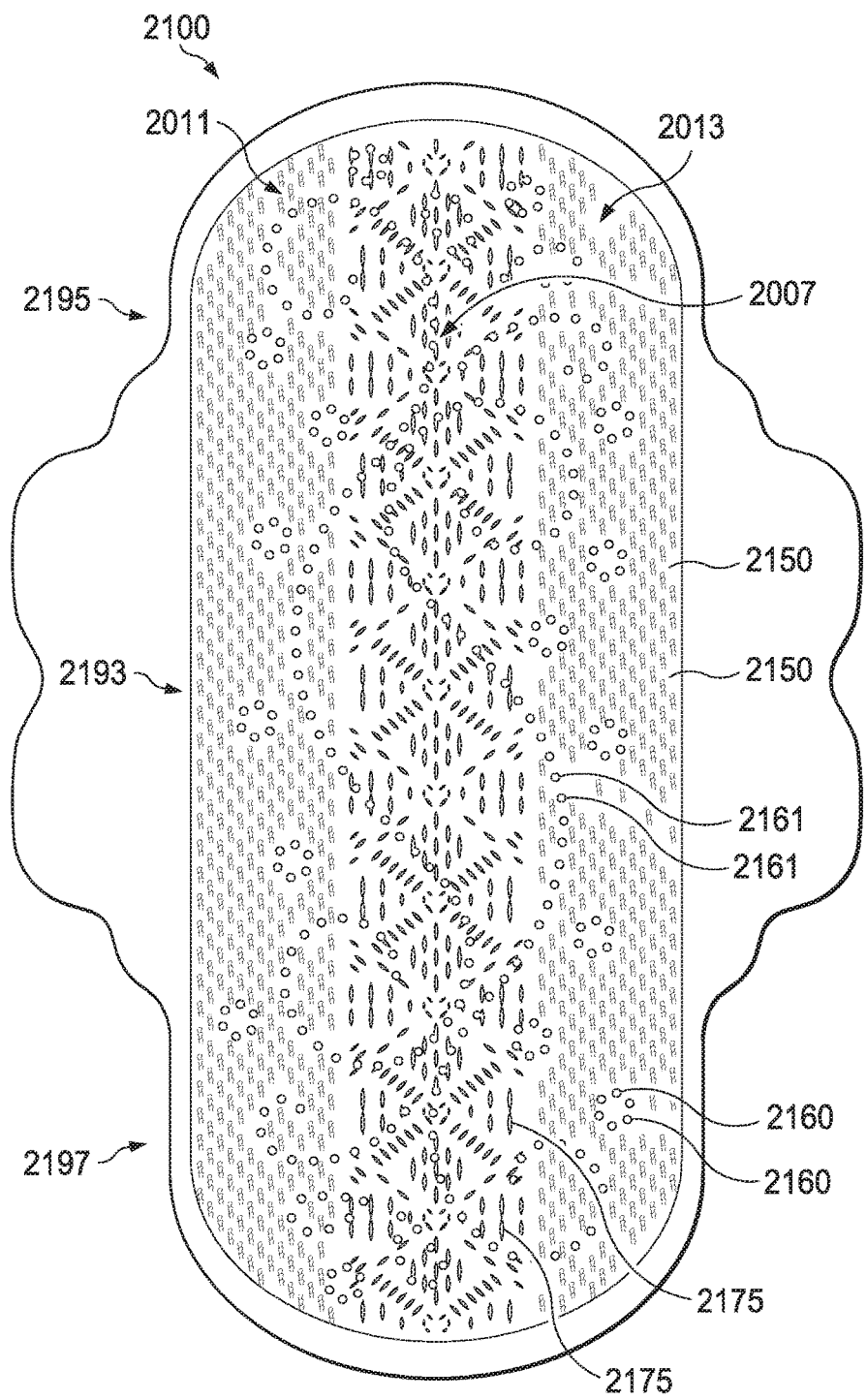
Figure 64:
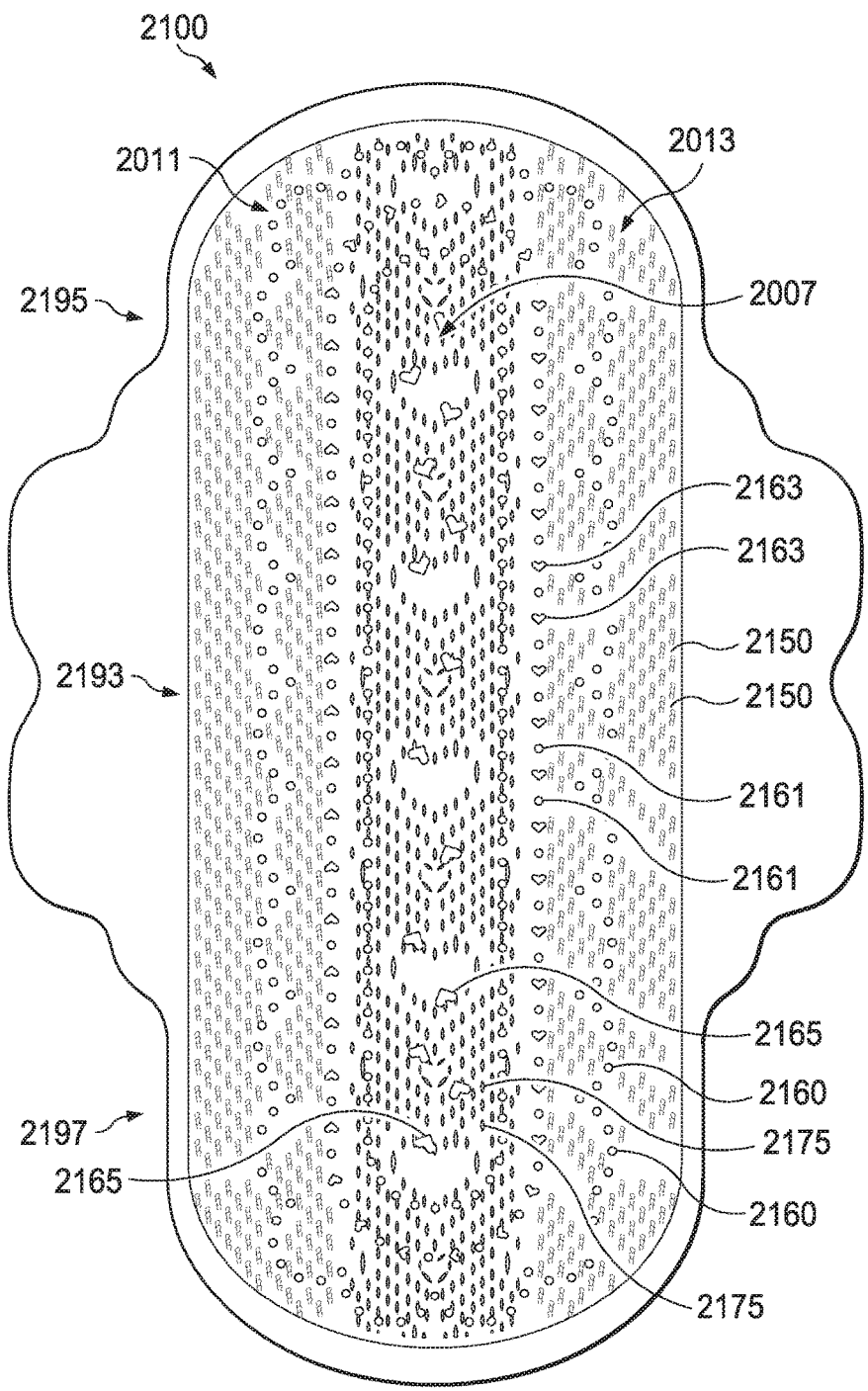
Figure 65:
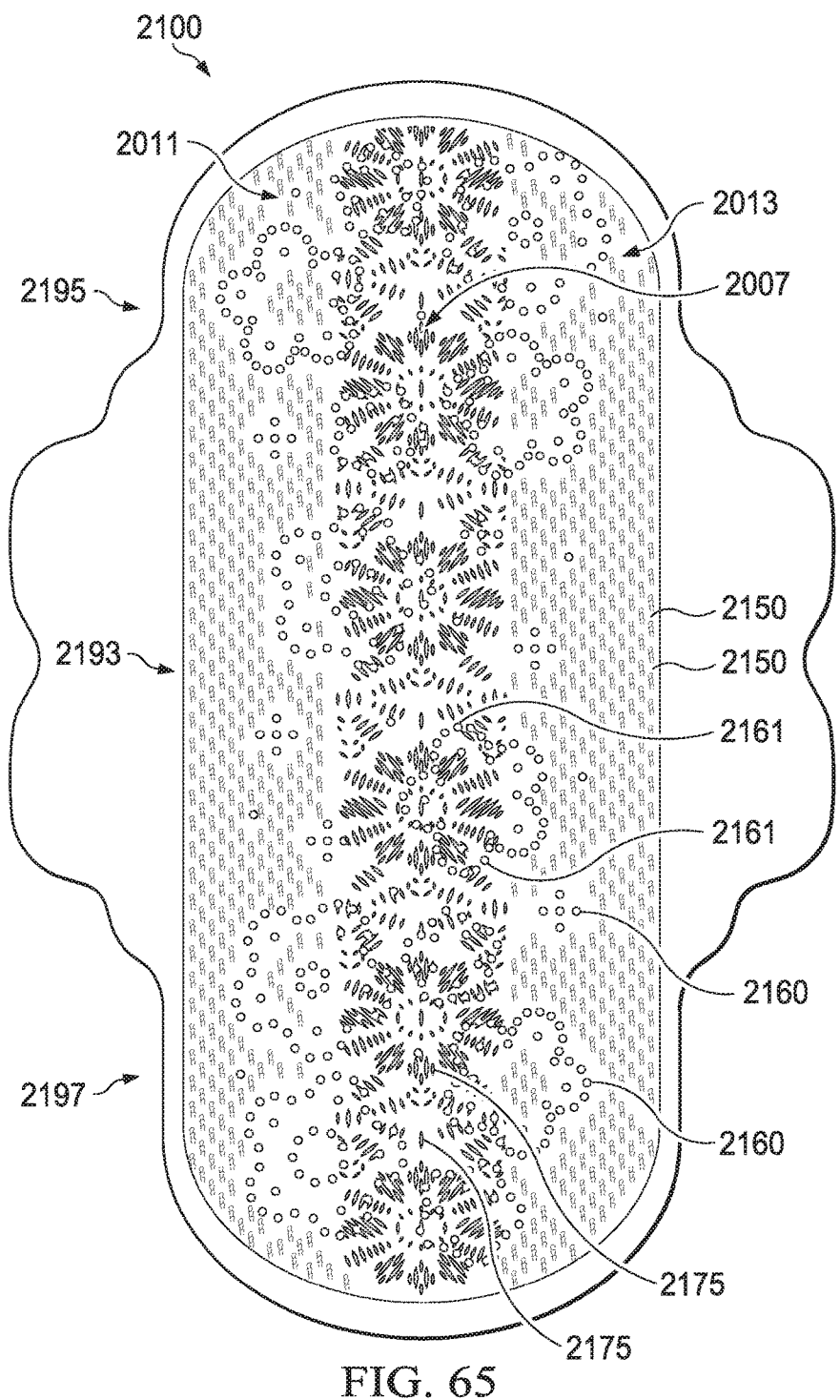

Referring specifically to FIG. 61—without being limited to sanitary pads—absorbent articles of the present invention may comprise a plurality of portions defined by the zones described with regard to FIG. 54 and the end areas defined in FIG. 61. For example, in some forms of the present invention, boundaries of the first zone 2007 may be coincident with the most outboard apertures of the first zone 2007 or may be approximately one third of a transverse width of the absorbent article in a flattened position. Similarly, the second zone 2011 and third zone 2013 may each comprise one third of the lateral width of the absorbent article. The first end area 2195, second end area 2197, and intermediate area 2193 may each comprise approximately one third of a length of the absorbent article in a flattened state.

In such forms, an absorbent article may comprise several portions: a portion in the first end area 2195 in the second zone 2011; a portion in the first end area 2195 in the first zone 2007; a portion in the first end area 2195 in the third zone 2013; a portion in the intermediate area 2193 in the second zone 2011; a portion in the intermediate area 2193 in the first zone 2007; a portion in the intermediate area in the third zone 2013; a portion in second end area 2197 in the second zone 2011; a portion in the second end area 2197 in the first zone 2007; and a portion in the second end area 2197 in the third zone 2013. Each of these portions may comprise any of the features described herein or any combination thereof. For example, a portion in the first end area 2195 in the second zone 2011 may comprise a plurality of apertures while another portion in the first end area 2195 in the first zone 2007 comprises a plurality of tufts. In some forms of the present invention the portion in the first end area 2195 and the second zone 2011 may further comprise tufts, ridges, grooves, etc.

Without wishing to be bound by theory it is believed that the masking effect of the bond sites may be attributable to a higher $\Delta E^*$ value compared to land areas between adjacent bond sites as opposed to the $\Delta E^*$ value of the apertures compared to the land areas between adjacent apertures. That said, it is further believed that bond site spacing may also play a significant role. For example, discontinuous bond sites may not produce the same masking effect as continuous bond sites. In some forms, embossing may provide a similar effect.

Visual Texture

Apertures, aperture arrays, three-dimensional elements, tufts, ridges, grooves, nubs, printing, patterned adhesives, or any combinations of these "texture elements" may impart a variable visually observed texture in an apertured web. Variations in observable textures have been extensively studied in the psychological and neurological sciences. Some small texture elements are much more readily ("instantly") detected by the human visual perception system than others. Most texture patterns having similar "second order" (iso-dipole) statistics cannot be discriminated in a brief "flash" observation. However, exceptions to this (i.e., iso-dipole texture elements that are easily discriminated) have been defined and are known in the literature as "textons". Apertured webs including texture elements forming texton shapes provide a way to create easily recognizable "zones" on a laminate or in an absorbent article, signaling regions having different functions, and/or providing strong cues as to correct product orientation on a wearer (e.g., front/back). Forms of the apertured webs of the present disclosure may include texture elements forming texton shapes, including quasi-collinearity, corner features, and closure of local features. A reference is Julesz, B., et al, *Visual Discrimination of Textures with Identical Third-Order Statistics*, Biological Cybernetics vol. 31, 1978, pp. 137-140).

Effective Open Area

An apertured web may have an Effective Open Area between about 5% to about 50%, about 5% to about 40%, about 8% to about 35%, about 10% to about 30%, about 10% to about 25%, about 3% to about 15%, or about 8% to about 15%, specifically including all 0.1% increments within the specified ranges and all ranges formed therein or thereby. All Effective Open Area percents are determined using the Aperture Test described herein. Apertured webs having a higher Effective Open Area may have utility as a topsheet or acquisition layer or system in an absorbent article (more functional to absorbent bodily exudates), while apertured webs having a lower Effective Open Area may have utility as an outer cover of an absorbent article (more decorative or for breathability purposes). In some forms of the present invention, for hydrophilic webs—where a body contacting surface is hydrophilic—the percentage open area can generally be less. For hydrophobic webs—where a body contacting surface is hydrophobic—the percentage open area may be increased to ensure good acquisition rates. As an example, for a hydrophobic topsheet, the percentage open area can be from about 5% to about 50%. As another example, for a hydrophilic topsheet, the percentage can be from about 1% to about 50%.

Effective Aperture Area

An apertured web may have apertures having an Effective Aperture AREA in the range of about 0.1 mm$^2$ to about 15 mm$^2$, 0.3 mm$^2$ to about 14 mm$^2$, 0.4 mm$^2$ to about 12 mm$^2$, 0.3 mm$^2$ to about 10 mm$^2$, 0.5 mm$^2$ to about 8 mm$^2$, 1.0 mm$^2$ to about 8 mm$^2$, or about 1.0 mm$^2$ to about 5 mm$^2$, specifically including all 0.05 mm increments within the specified ranges and all ranges formed therein or thereby. All Effective Aperture Areas are determined using the Aperture Test described herein. A plurality of the apertures in an apertured web may be different in Effective Aperture Areas. The Relative Standard Deviation ("RSD") of the Effective Aperture Areas may be at least about 20 percent, at least about 30 percent, at least about 50 percent or at least about 55 percent, or at least about 60 percent.

Interaperture Distance and Average Interaperture Distance

The apertured webs or layers thereof may have apertures that have an Average Interaperture Distance of less than about 3.5 mm, less than about 3 mm, less than about 2.5 mm, less than about 2 mm, less than about 1.5 mm, less than about 1 mm, in the range of about 1 mm to about 6 mm, in the range of about 1 mm to about 5 mm, in the range from about 1 mm to about 4 mm, in the range from about 1 mm to about 3.5 mm, in the range of about 1 mm to about 3 mm, in the range of about 1 mm to about 2.5 mm, in the range of about 2 mm to about 4 mm, in the range of about 3.5 mm to about 10 mm, or in the range of about 0.08 mm to about 11 mm, specifically reciting all 0.1 mm increments within the above-specified ranges and all ranges formed therein or thereby, according to the Interaperture Distance Test herein.

An apertured web may have Interaperture Distances, calculated according to the Interaperture Distance Test herein. The Interaperture Distances may have a distribution having a mean and a median. The mean may be greater than, different than, or less than the median. The difference between the mean and the median may be in the range of about 1% to about 25%, about 4% to about 25%, about 5% to about 20%, about 8% to about 20%, about 4% to about 15%, or about 1% to about 8%, for example, specifically reciting all 0.1% increments within the above specified ranges and all ranges formed therein or thereby. A first zone of an apertured web may have Interaperture Distances. The Interaperture Distances of a first zone may have a first distribution having a first mean and a first median. The first mean may be greater than, different than, or less than the first median by the ranges set forth above in this paragraph. A second zone of the apertured web may have Interaperture Distances. The Interaperture Distances of the second zone may have a second distribution having a second mean and a second median. The second mean may be greater than, less than, or different than the second median by the ranges set forth above in this paragraph. A third zone of the apertured web may have Interaperture Distances. The Interaperture Distances of the third zone may have a third distribution having a third mean and a third median. The third mean may be greater than, different than, or less than the third median by the ranges set forth above in this paragraph. The first, second, and third means may be the same or different. The first, second, and third medians may be the same or different.

The first, second, and third zones may be in a topsheet, a topsheet layer, an acquisition layer, an outercover, an outercover layer, or any other component of an absorbent article or other consumer products.

In other instances, a first portion of an absorbent article or other consumer product may have a first apertured web that has Interaperture Distances, according to the Interaperture Distance Test herein. The Interaperture Distances of the first portion have a first distribution. A second portion of an absorbent article or other consumer product may have a second apertured web that has Interaperture Distances, according to the Interaperture Distance Test herein. The Interaperture Distances of the second portion have a second distribution. A third portion of an absorbent article or other consumer product may have a third apertured web that has Interaperture Distances, according to the Interaperture Distance Test herein. The Interaperture Distances of the third portion have a third distribution. The first, second, and third distributions may be the same or different. The first distribution may have a first mean and a first median. The first mean may be greater than, less than, or different than the first median in the range of about 1% to about 25%, about 4% to about 25%, about 5% to about 20%, about 8% to about 20%, about 4% to about 15%, or about 1% to about 8%, for example, specifically reciting all 0.1% increments within the above-specified ranges and all ranges formed therein or thereby. The second distribution may have a second mean and a second median. The second mean may be greater than, different than, or less than the second median by the ranges set forth above in this paragraph. The third distribution may have a second mean and a second median. The second mean may be greater than, different than, or less than the second median by the ranges set forth above in this paragraph. The first, second, and third means may be the same or different. The first, second, and third medians may be the same or different. The Relative Standard Deviation (RSD) of the Interaperture Distances may be at least 25%, at least about 35%, at least about 40%, at least about 50%, or at least about 55%. The Maximum Interaperture Distance in a given web or pattern may be at least about 5 mm, at least about 8 mm, at least about 10 mm, or at least about 11 mm.

Average Absolute Feret Angle and Absolute Feret Angle

An apertured web may have one or more apertures having an Absolute Ferret Angle, according to the Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby.

An apertured web may have a plurality of apertures having an Average Absolute Ferret Angle, according to the Average Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby. These apertures may all be within a single repeat unit of the apertured web.

At least two, at least 3, at least 4, at least 5, at least 6, at least 7, at least 8, at least 9, or at least 10 of the apertures in an apertured web, or a repeat unit of an apertured web, may each have a different Absolute Feret Angle, according to the Absolute Feret Angle Test herein. In other instances, some of the apertures may have Absolute Feret Angles that are the same, while other of the apertures may have Absolute Feret Angles that are different. In addition to having different Absolute Feret Angles, the at least two, at least 3, at least 4, at least 5, at least 6, at least 7, at least 8, at least 9, or at least 10 apertures may have different sizes and/or shapes. At least some of the At least two, at least 3, at least 4, at least 5, at least 6, at least 7, at least 8, at least 9, or at least 10 apertures may also have the same size and/or shape, while having different Absolute Feret Angles.

Apertures oriented at ferret angles greater than zero relative to the machine direction may have a higher aspect ratio than apertures that are aligned in the machine direction or vice versa. Apertured webs having elongated apertures oriented at different ferret angles may provide liquid bodily exudate handling benefits when the apertured web is used as a topsheet in an absorbent article. For example, fluid run-off may be reduced in the front or back of the absorbent article when the apertures are not all aligned in the machine direction, but instead are oriented at an angle relative to the machine direction (e.g., about 30 degrees, about 45 degrees, or even about 90 degrees) as the apertures can more readily acquire the liquid bodily exudates. Therefore, it may be desirable to have the central longitudinal axes of the elongated apertures oriented at multiple different ferret angles in order to most effectively acquire liquid bodily exudates running along the surface of the apertured web and prevent, or at least inhibit, run-off and soiling of garments.

In some forms of the present invention, an apertured web may comprise a plurality of apertures wherein a first portion of the apertures have an Absolute Feret angle of less than about 20 degrees and wherein a second portion of the apertures have an Absolute Feret angle of greater than about 20 degrees. In some forms, the first portion may comprise about 50% of the plurality of apertures. In some forms, the first portion may comprise about 40% of the plurality of apertures. In some forms, a first plurality of apertures may comprise more apertures than a second plurality of apertures by a ratio of about 3 to 1 or about 5 to 1. In some forms, the first plurality of apertures may be disposed about the second plurality of apertures.

In some example apertured webs of the present disclosure, a pattern of overbonds, each of which is oriented solely in the machine direction, or substantially in the machine direction (i.e., +/−5 degrees or less from the machine direction), may be used to create an apertured web with apertures having central longitudinal axes that are not all oriented in the machine direction or, stated another way, that have ferret angles of more than 5 degrees with respect to the machine direction. An example overbond pattern having overbonds "O" oriented solely in the machine direction is contemplated. This overbond pattern may be used to produce the example apertured web 10 of FIG. 3. The apertured web 10 of FIG. 3 may have some apertures 12 having a central longitudinal axis, L, having an angle with respect to the machine direction. The aperture ferret angle may range from about 5 degrees to about 70 degrees, specifically reciting all 0.5 degree increments within the specified range and all ranges formed therein. Some of the apertures 12 in the apertured web 10 may also have a central longitudinal axis, L1, that extends parallel to, or substantially parallel to (e.g., +/− less than 5 degrees), the machine direction. The cross directional stretching step or steps described herein may be used to create the apertures and to orient the central longitudinal axes, L, of at least some of the apertures in a direction not parallel to, or substantially parallel to, the machine direction. At least some of the apertures in an apertured web having their central longitudinal axes not parallel to, or substantially parallel to, the machine direction may have a first plurality of apertures having central longitudinal axes extending in a first direction with respect to the machine direction and a second plurality of apertures having central longitudinal axes extending at a second, different direction relative to the machine direction. The first and second directions may be 30 degrees and −30 degrees, respectively, 10 degrees and 20 degrees respectively, or −20 degrees and 30 degrees respectively, to provide a few examples. Those of skill in the art will recognize that angles relative to the machine direction are also within the scope of the present disclosure. The Relative Standard Deviation (RSD) of the Absolute Feret Angles may be at least about 30%, or at least about 40%, or at least about 50%. The Absolute Feret Angle of apertures within a repeat unit may differ by at least about 5 degrees, at least about 10 degrees, at least about 20 degrees, or at least about 03 degrees.

The apertures in an apertured web having a central longitudinal axis angled with respect to the machine direction and produced by machine direction overbonds may be more open (i.e., have a lower aspect ratio) than they would have been if the overbonds had been oriented at an angle (5 degrees or more) with respect to the machine direction. Overbonds oriented at an angle with respect to the machine direction typically produce apertures having higher aspect ratios post cross directional stretching that are less open.

Example Overbond Patterns for Apertured Webs

Figure 70:
FIGS. 70-71 are schematic illustrations showing overbond patterns on a web in accordance with the preset invention.
Figure 71:
Figure 72:
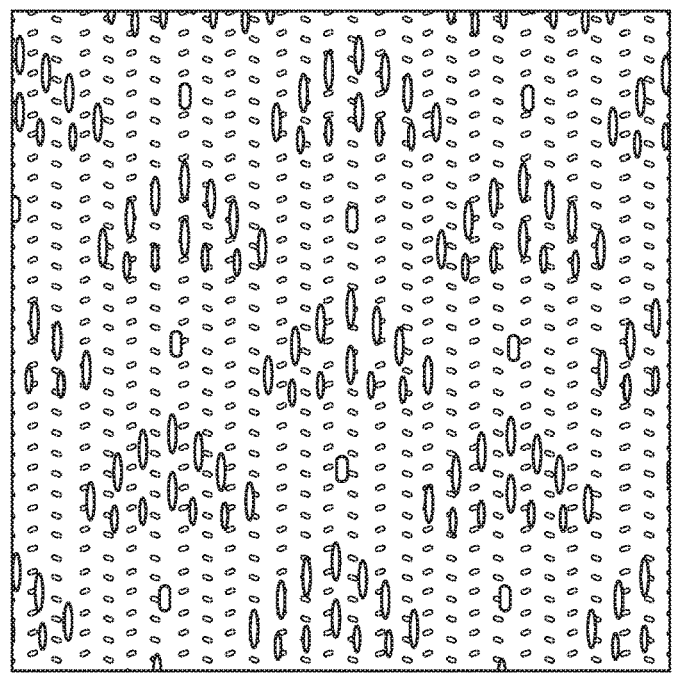
FIGS. 72-81 are photographs of apertured webs in accordance with the present disclosure.
Figure 73:
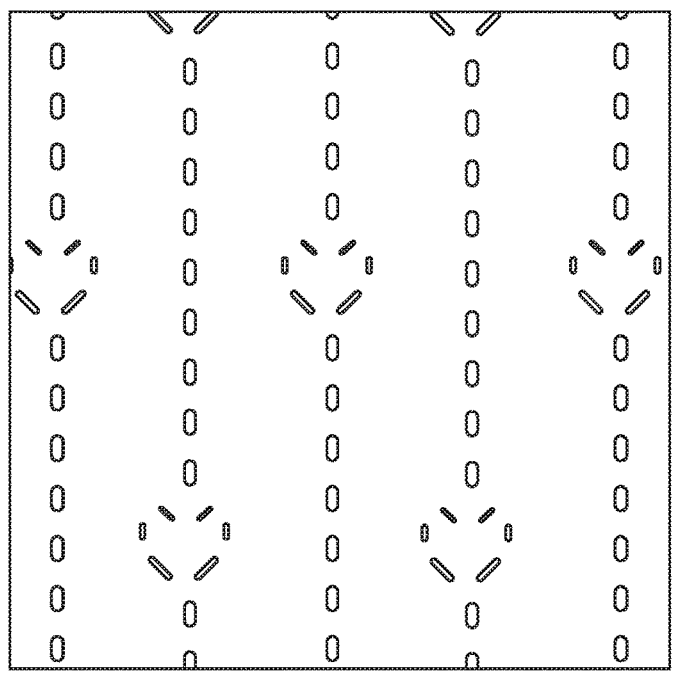
Figure 74:
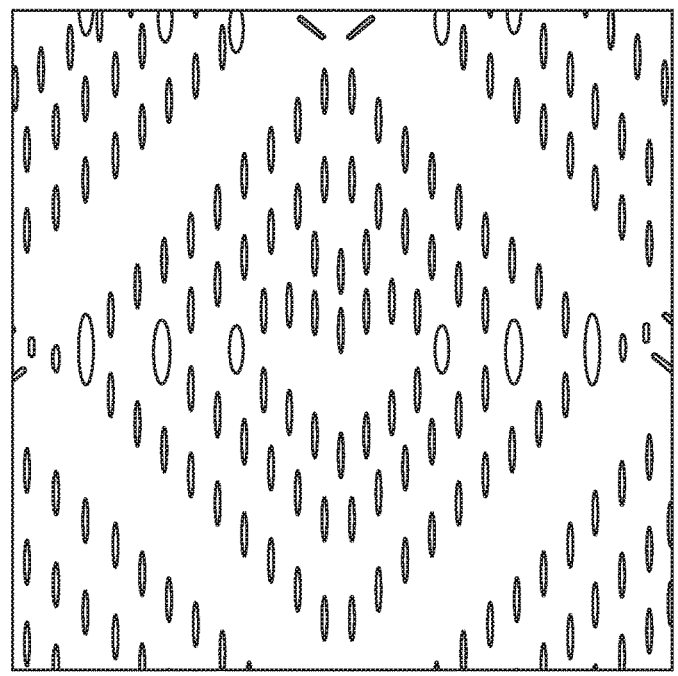
Figure 75:
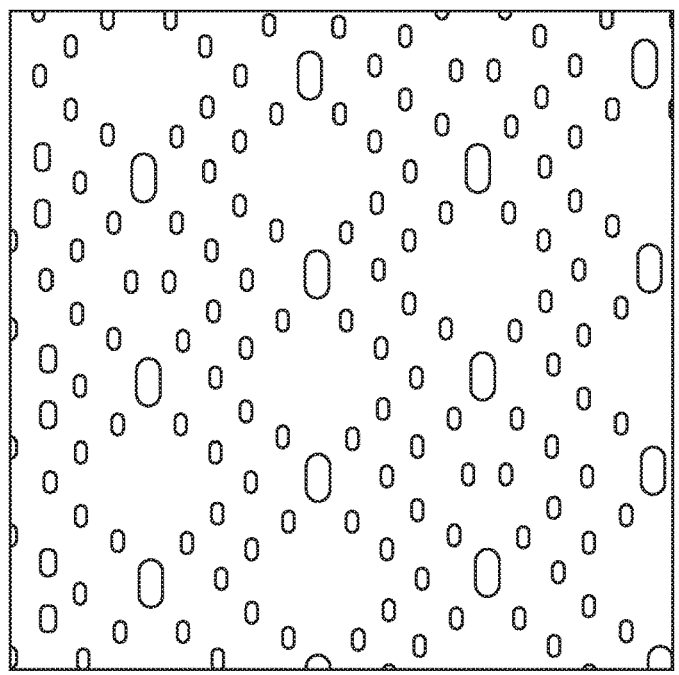
Figure 76:
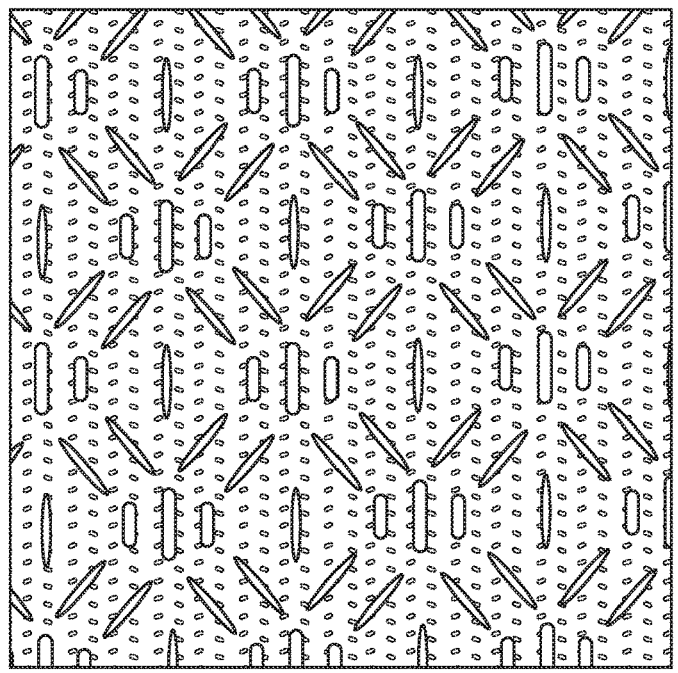
Figure 77:
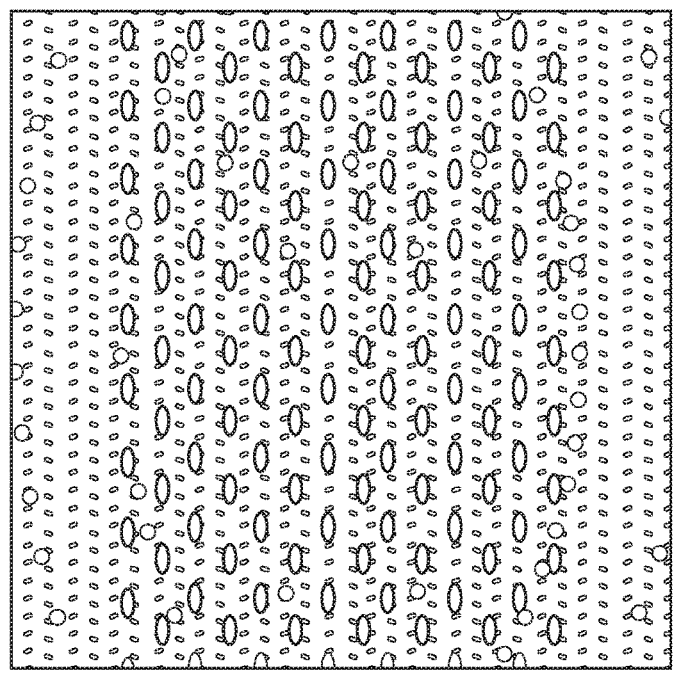
Figure 78:
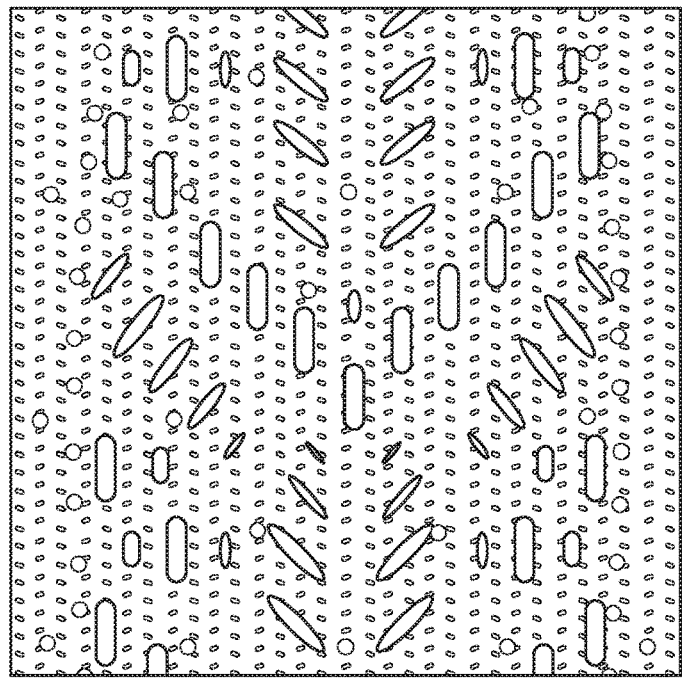
Figure 79:
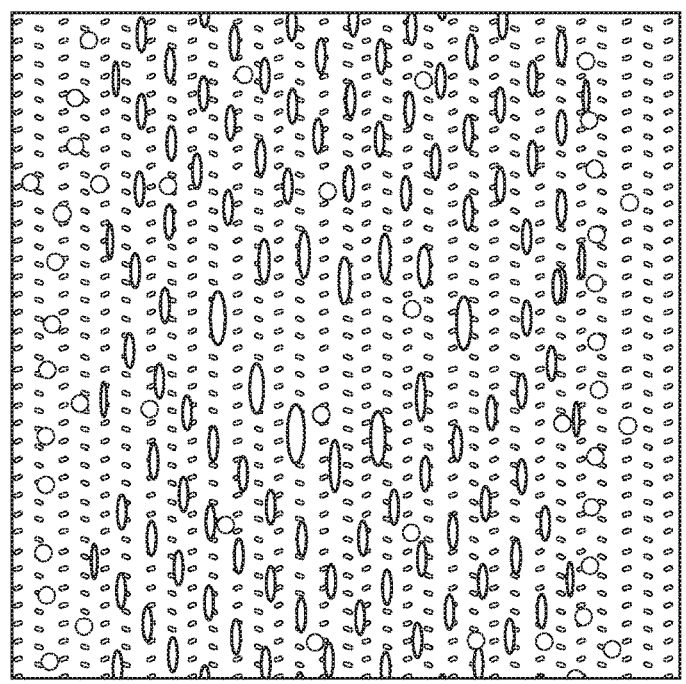
Figure 80:
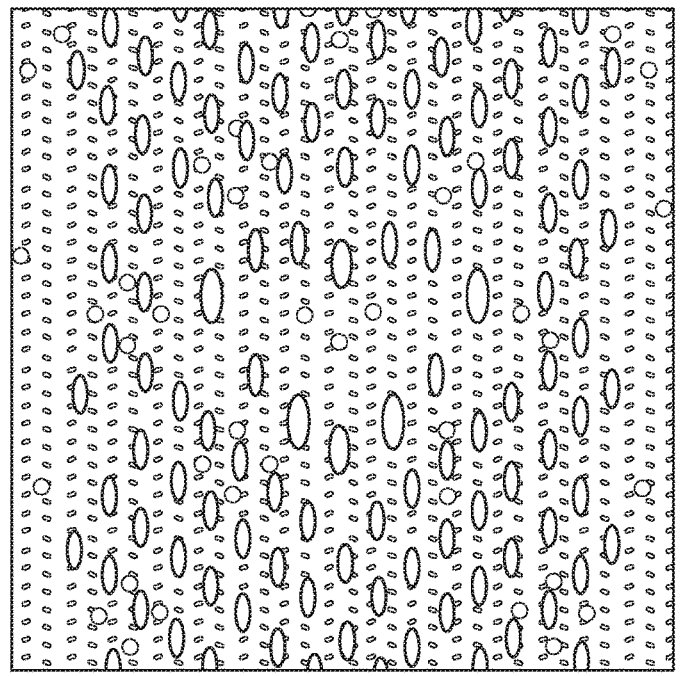
Figure 81:
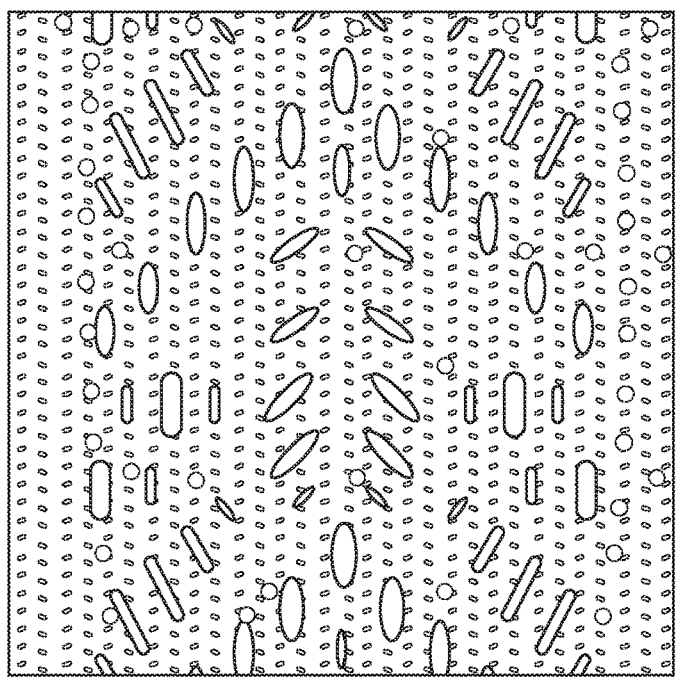

Some example schematic representations of overbond patterns that could be used on an overbonding roller, like roller 110 of FIG. 13 are illustrated in FIGS. 70 and 71. Those of skill in the art will recognize that other suitable overbond patterns are also within the scope of the present disclosure, along with variations of the illustrated patterns.

Aperture Aspect Ratio and Area

The apertures of the apertured webs of the present disclosure may have an aspect ratio of greater than one, for example, greater than two, greater than 3, greater than 5, or greater than 10, but typically less than 15. The aperture patterns in the apertured web may comprise apertures having more than one aspect ratio, such as two or more distinct populations or having a substantially continuous distribution of aspect ratios having a slope greater than zero. Additionally, the aperture patterns of the apertured webs may comprise apertures with more than two effective aperture area, either as two or more distinct populations or as a distribution of aperture areas having a slope greater than zero. The Relative Standard Deviation (RSD) of the aperture aspect ratios may be at least about 15%, at least about 25%, at least about 30%, or at least about 40%, or at least about 45%.

Fused Portions

Figure 36:
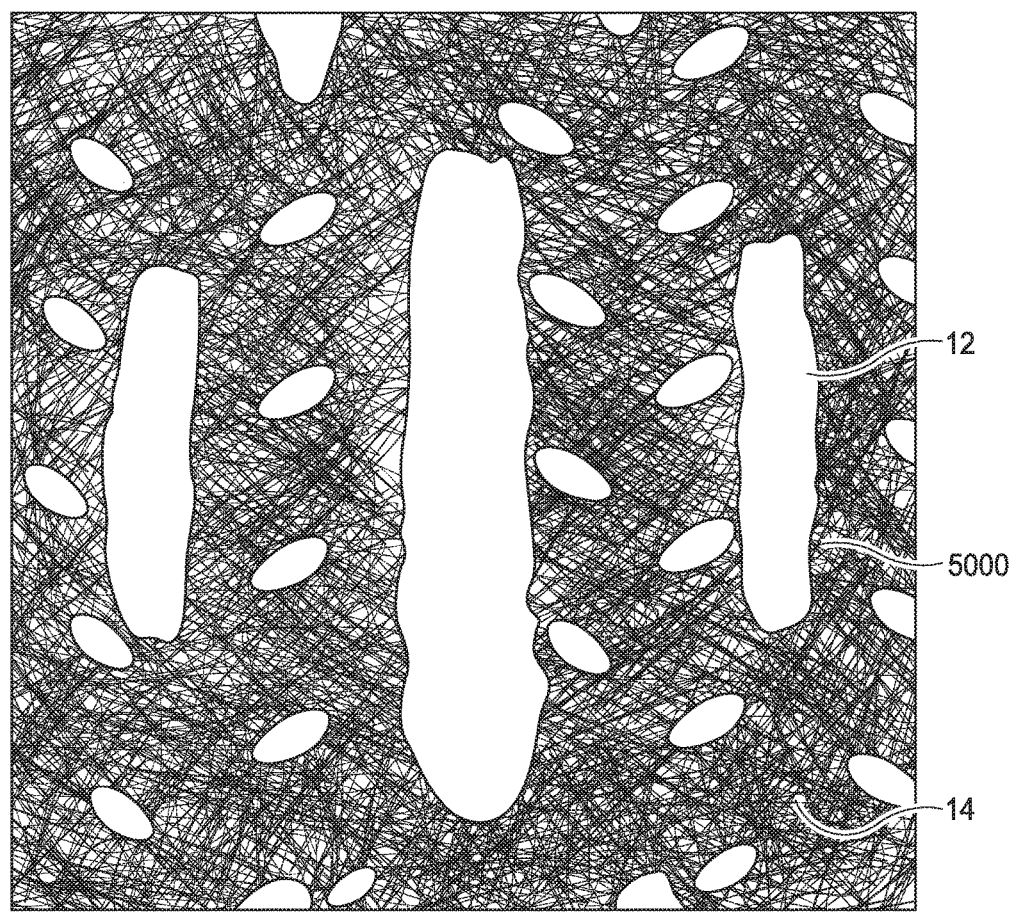
FIG. 36 is a photograph of a portion of a apertured web comprising fused portions surrounding the apertures in accordance with the present disclosure.

Referring to FIG. 36, areas surrounding at least a portion of an aperture 12 in an apertured web of the present disclosure may comprise one or more fused portions 5000. The fused portions 5000 may at least partially surround the apertures 12, or fully surround the apertures 12. The fused portions 5000 may surround at least 25% of a perimeter of the apertures 12 up to about 100% of the perimeter of the apertures 12. In some instances, the fused portions 5000 may be formed on the lateral sides of the apertures 12 and not on the leading and trailing edges of the apertures 12 (see MD and CD arrows for reference in FIG. 36). The fused portions 5000 are believed to be formed during the overbonding step and are believed to add strength to the apertured webs.

Packages

Absorbent articles comprising the apertured webs of the present disclosure may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles according to the present disclosure may have an in-bag stack height of less than about 80 mm, less than about 78 mm, or less than about 76 mm, according to the In-Bag Stack Height Test described herein. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test described herein. Further details regarding in-back stack height are disclosed in U.S. Pat. No. 8,585,666, to Weisman et al., issued on Nov. 19, 2013.

Arrays of Products

In some forms, arrays of products are contemplated which comprise a plurality of features. For example, a first plurality of absorbent articles may comprise a first array of features forming indicia, e.g. apertured indicia, adhesive indicia, bond indicia, print indicia, structural indicia. A second plurality of articles may comprise a second array of features forming indicia, e.g. apertured indicia, adhesive indicia, bond indicia, print indicia, structural indicia. In some forms, the indicia provided for the first plurality of articles may be different than the indicia provided for the second plurality of articles. In some forms, a third plurality of articles may comprise a third array of features forming indicia, e.g. apertured indicia, adhesive indicia, bond indicia, print indicia, structural indicia. In some forms, the indicia provided for the third plurality of article can be different than the indicia provided for the first and the second plurality of articles. However, in some forms, the indicia between a first plurality and second plurality may be coordinated while the indicia provided for the third plurality of articles is not coordinated with the first plurality and/or second plurality. For example, where the first plurality and second plurality of articles are related functionally. For example, where the first and second plurality of articles are the same size, or are the same level of absorbency but different sizes, etc. Still in other forms of the present invention, a first plurality of products may comprise a plurality of features which form indicia, e.g. apertured indicia, adhesive indicia, bond indicia, print indicia, structural indicia. In such forms, a second plurality of products may comprise a plurality of features which do not create indicia.

Opacity Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2° C. and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Aperture/Feret Angle Tests

Aperture dimensions, Effective Open Area and Inter-Aperture Distance measurements are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then threshold, separating open aperture regions from specimen material regions, and analyzed using the image analysis program. All testing is performed in a conditioned room maintained at about 23±2° C. and about 50±2% relative humidity.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2° C. and about 50%±2% relative humidity for 2 hours prior to testing.

Image Acquisition:

Place the ruler on the scanner bed, oriented parallel to the sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of the interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm$^2$, including partial apertures along the edges of the image. Discard any apertures with an area less than 0.3 mm$^2$. Apertures having a lower area than 0.3 mm$^2$ may prove difficult to measure particularly when stray fibers cross the boundary of the aperture. And such apertures with that small of an area are considered to contribute insignificantly to the Effective Open Area. Sum the remaining aperture areas (including whole and partial apertures), divide by the total area included in the image and multiply by 100. Record this value as the % Effective Open Area to the nearest 0.01%.

In like fashion, analyze the remaining four specimen images. Calculate and report the average % effective area values to the nearest 0.01% for the five replicates.

Effective Aperture Area and Absolute Feret Angle:

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. Set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0. Next, two morphological operations are performed on the binary image. First, a closing (a dilation operation followed by an erosion operation, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual aperture areas, perimeters, feret diameters (length of the apertures) along with its corresponding angle of orientation in degrees from 0 to 180, and minimum feret diameters (width of the apertures). Record the measurements for each of the individual aperture areas to the nearest 0.01 mm$^2$, the perimeters and feret diameters (length and width), to the nearest 0.01 mm, and angles to the nearest 0.01 degree. Discard any apertures with an area less than 0.3 mm$^2$. Record the number of remaining apertures, divide by the area of the image and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Aperture Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension measurements using all of the aperture values recorded from the replicates. Calculate and report the % relative standard deviation (RSD) for each of the aperture dimension measurements by dividing the standard deviation by the mean and multiplying by 100.

Inter-Aperture Distance Measurements:

The average, standard deviation, median, and maximum distance between the apertures can be measured by further analyzing the binary image that was analyzed for the aperture dimension measurements. First, obtain a duplicate copy of the resized binary image following the morphological operations, and using the image analysis program, perform a Voronoi operation. This generates an image of cells bounded by lines of pixels having equal distance to the borders of the two nearest pattern apertures, where the pixel values are outputs from a Euclidian distance map (EDM) of the binary image. An EDM is generated when each inter-aperture pixel in the binary image is replaced with a value equal to that pixel's distance from the nearest pattern aperture. Next, remove the background zeros to enable statistical analysis of the distance values. This is accomplished by using the image calculator to divide the Voronoi cell image by itself to generate a 32-bit floating point image where all of the cell lines have a value of one, and the remaining parts of the image are identified as Not a Number (NaN). Lastly, using the image calculator, multiply this image by the original Voronoi cell image to generate a 32-bit floating point image where the distance values along the cell lines remain, and all of the zero values have been replaced with NaN. Next, convert the pixel distance values into actual inter-aperture distances by multiplying the values in the image by the pixel resolution of the image (approximately 0.04 mm per pixel), and then multiply the image again by 2 since the values represent the midpoint distance between apertures. Measure and record the mean, standard deviation, median and maximum inter-aperture distances for the image to the nearest 0.01 mm. Repeat this procedure for all replicate images. Calculate the % relative standard deviation (RSD) for the inter-aperture distance by dividing the standard deviation by the mean and multiplying by 100.

Land Area Light Transmission Method

The land area light transmission method measures the average amount of light transmitted through specific regions of a specimen. A calibrated light transmission image is obtained using a flatbed scanner. A binary mask is generated to separate discrete aperture regions from the surrounding land area. The binary mask is then registered to the light transmission image, and used to exclude the apertures from the land area in the light transmission image. This enables the average light transmission value for the land area to be calculated.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. Condition the samples at about 23° C.±2° C. and about 50%±2% relative humidity for 2 hours prior to testing.

Light Transmission Image

The light transmission measurement is based on the CIE L*a*b* color system (CIELAB). A flatbed scanner capable of scanning a minimum of 24 bit color at 800 dpi and has manual control of color management (a suitable scanner is an Epson Perfection V750 Pro from Epson America Inc., Long Beach Calif. or equivalent) is used to acquire images. The scanner is interfaced with a computer running color management software (suitable color management software is MonacoEZColor available from X-Rite Grand Rapids, Mich. or equivalent). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L*a*b* (a suitable program is Photoshop S4 available from Adobe Systems Inc., San Jose, Calif. or equivalent). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 200 dpi and 24 bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the outward facing surface facing the glass. Acquire and import a scan of the specimen region within the interior of the frame into the image analysis software at 24 bit color and at 800 dpi in transparency mode. If necessary, crop image to a rectangular field of view circumscribing the apertured region. Transparency mode illuminates the specimen from one side with the sensor capturing the image from the opposite side. Assign the calibrated color profile to the image and change the color space mode to L*a*b* Color corresponding to the CIE L*a*b* standard. This produces a color corrected image for analysis. Save this color corrected image in an uncompressed format, such as a TIFF file.

Land Area Mask

The boundaries of the apertured areas and land area are identified by thresholding the L* channel image to generate a binary image, separating apertured areas from the surrounding land area. This binary image will then be used as a mask on the corresponding light transmission image to measure the average Light Transmission Value of only the land area.

To do this, first open the color corrected light transmission image in the image analysis software. To generate the land area mask, first separate the L*, a* and b* channels, and select only the L* channel for analysis. The L* channel represents the "Lightness" of the image and has values that range from 0-100. Threshold the L* channel image at a value of 90 to generate a binary image. By thresholding at the level described above, a binary mask image is produced with the discrete aperture areas assigned one value, and the surrounding land area assigned a different value. For example, the discrete aperture areas could appear black, and the surrounding land area could appear white. Save this binary mask image in an uncompressed format, such as a TIFF file.

Analysis of Light Transmission Image

Open both the color corrected light transmission image and the corresponding binary mask image in the image analysis software. To analyze the specimen light transmission image, first separate the L*, a* and b* channels, and select only the L* channel for analysis. Register the light transmission image and the binary mask image to each other. Use the binary mask to exclude the apertures from the light transmission image, and calculate an average L* value (Light Transmission Value) for the remaining surrounding land area. Record this value as the Land Area Light Transmission Value to the nearest 0.1 units. In like fashion, repeat this procedure on all of the replicate specimens. Calculate and report the average of the five individual Land Area Light Transmission Values to the nearest 0.1 units.

Basis Weight Method

Basis weight of the apertured webs may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the apertured web (e.g., topsheet, outer cover) from the approximate center of the absorbent article or other consumer product in a location which avoids to the greatest extent possible any adhesive which may be used to fasten the apertured web to any other layers which may be present and removing the apertured web from other layers (using cryogenic spray, such as Cyto-Freeze, Control Company, Houston, Tex., if needed). The sample is then weighed and dividing by the area of the punch die yields the basis weight of the apertured web. Results are reported as a mean of 5 samples to the nearest 0.1 cm$^2$.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Definitions

Figure 37:
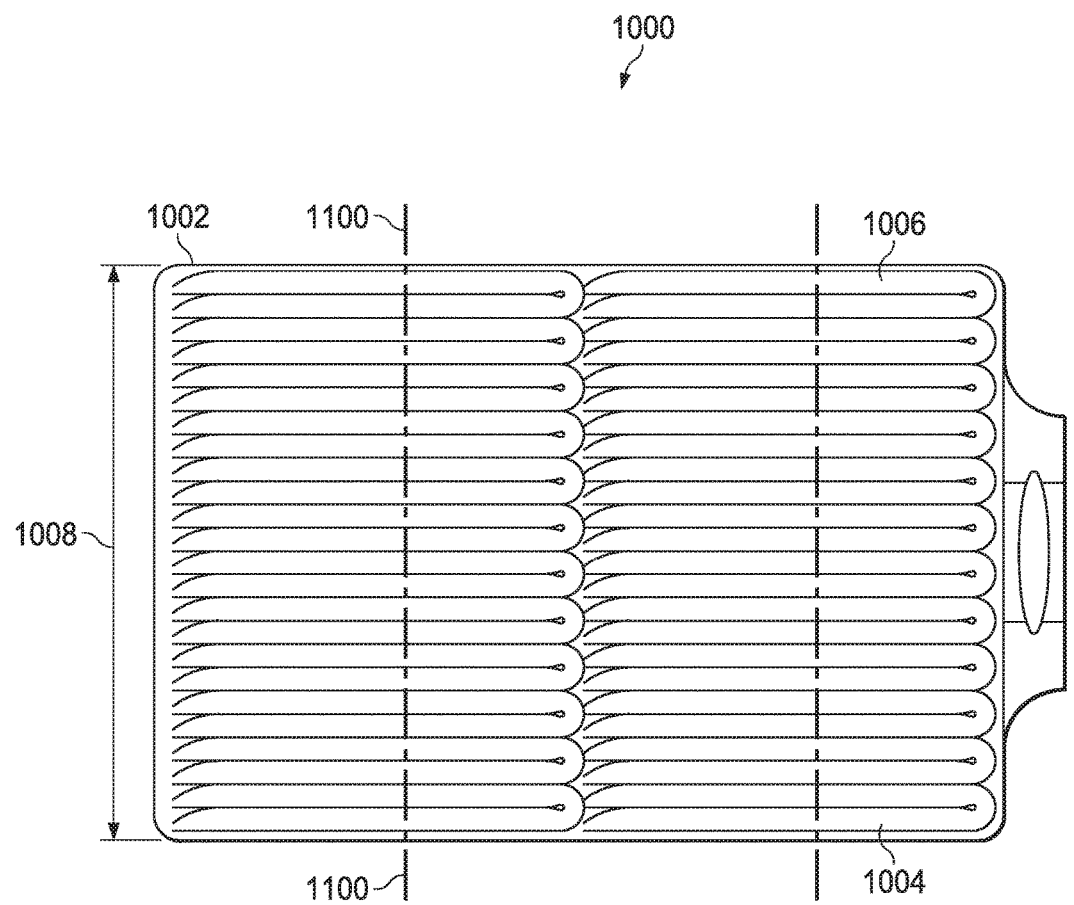
FIG. 37 is a side view of a package of absorbent articles in accordance with the present disclosure. The outer surface is illustrated as transparent for purposes of clarity.

As illustrated in FIG. 37, a package 1000 defines an interior space 1002 and comprises a plurality of absorbent articles 1004. The absorbent articles are in a stack 1006. The package has a package width 1008. The package width is defined as the maximum distance between the two highest bulging points along the same compression stack axis of the absorbent article package 1000.

In-Bag Stack Height=(Package Width/Pad Count Per Stack)×10 absorbent articles.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 37). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. A disposable absorbent article comprising a longitudinal axis and a lateral axis perpendicular to the longitudinal axis, a pair of side edges extending generally parallel to the longitudinal axis and a pair of end edges joining said pair of side edges on opposite ends of the disposable absorbent article, the disposable absorbent article further comprising:
   a topsheet comprising a web having a length substantially parallel to the longitudinal axis and a width substantially parallel to the lateral axis, the web comprising an array of apertures forming apertured indicia, the indicia formed by a pattern repeating along the length of the topsheet via a plurality of repeat units, each repeat unit comprising:
      a first plurality of apertures, each of the first plurality of apertures having a first length and a first width, wherein the first length is greater than the first width, wherein each of the first lengths is substantially parallel to the longitudinal axis,
      a second plurality of apertures, each of the second plurality of apertures having a second length and a second width, wherein the second length is greater than the second width, each of the second lengths being non-parallel to the longitudinal and lateral axes and oriented in a first Absolute Feret Angle, and
      a third plurality of apertures, each of the third plurality of apertures having a third length and a third width, wherein the third length is greater than the third width, each of the third lengths being non-parallel to the longitudinal and lateral axes and oriented in a second Absolute Feret Angle, wherein the first Absolute Feret Angle and the second Absolute Feret Angle are different,
   wherein each Absolute Feret Angle is derived from an aperture angle of its length with respect to the lateral axis measured from 0 and 180 degrees, such that an aperture parallel to the longitudinal axis is 90 degrees, subtracting 90 degrees from the aperture angle and taking the absolute value of the difference,
   wherein some of the first plurality of apertures are disposed on one side of the longitudinal axis and some of the first plurality of apertures are disposed on another side of the longitudinal axis, each of the second plurality of apertures is disposed on the one side of the longitudinal axis, and each of the third plurality of apertures is disposed on the other side of the longitudinal axis from the second plurality of apertures;
   a backsheet; and
   an absorbent core disposed between the topsheet and the backsheet.

2. The disposable absorbent article of claim 1, wherein each repeat unit further comprises a fourth plurality of apertures, each of the fourth plurality of apertures having a fourth length and a fourth width, wherein the fourth length is greater than the fourth width, each of the fourth lengths being non-parallel to the longitudinal and lateral axes and oriented in a third Absolute Feret Angle, wherein the third Absolute Feret Angle is different from the first Absolute Feret Angle and the second Absolute Feret Angle.

3. The disposable absorbent article of claim 1, wherein each repeat unit further comprises a fourth plurality of apertures, each of the fourth plurality of apertures having a fourth length and a fourth width, wherein the fourth length is greater than the fourth width, each of the fourth lengths being non-parallel to the longitudinal and lateral axes and oriented in the first Absolute Feret Angle, wherein each of the fourth plurality of apertures is disposed on the other side of the longitudinal axis.

4. The disposable absorbent article of claim 3, wherein each repeat unit further comprises a fifth plurality of apertures, each of the fifth plurality of apertures having a fifth length and a fifth width, wherein the fifth length is greater than the fifth width, each of the fifth lengths being non-parallel to the longitudinal and lateral axes and oriented in the second Absolute Feret Angle, wherein each of the fifth plurality of apertures is disposed on the one side of the longitudinal axis.

5. The disposable absorbent article of claim 4, wherein the second plurality of apertures is a mirror image of the fourth pluralities of apertures and the third plurality of apertures is a mirror image of the fifth plurality of apertures.

6. The disposable absorbent article of claim 3, wherein each repeat unit further comprises a fifth plurality of apertures, each of the fifth plurality of apertures having a fifth length and a fifth width, wherein the fifth length is greater than the fifth width, each of the fifth lengths being non-parallel to the longitudinal and lateral axes and oriented in the first Absolute Feret Angle, wherein each of the fifth plurality of apertures is disposed on either the one or the other side of the longitudinal axis.

7. The disposable absorbent article of claim 4, wherein the fifth plurality of apertures is on the other side of the longitudinal axis and the second plurality of apertures is a mirror image of the fourth pluralities of apertures and the second plurality of apertures is not a mirror image of the fifth plurality of apertures.

8. The disposable absorbent article of claim 1, wherein the Absolute Feret angle is from about 2 degrees to about 80 degrees.

9. The disposable absorbent article of claim 1, wherein the first plurality of apertures comprises more apertures than the second plurality of apertures in a ratio of about 3 to 1.

10. The disposable absorbent article of claim 1, wherein the first plurality of apertures comprises more apertures than the second plurality of apertures in a ratio of about 5 to 1.

11. The disposable absorbent article of claim 1, wherein the topsheet further comprises a first zone disposed between a second zone and a third zone, wherein some of the first plurality of apertures and the second plurality of apertures are disposed within the first zone.

12. The disposable absorbent article of claim 1, wherein the topsheet further comprises a first zone disposed between a second zone and a third zone, wherein the first, second, and third pluralities of apertures are disposed within the first zone.

13. The disposable absorbent article of claim 1, wherein the topsheet further comprises a first zone disposed between a second zone and a third zone, wherein the array of apertures is disposed within the first zone.

14. The disposable absorbent article of claim 1, the web has an Effective Open Area in a zone containing the array of apertures of about 5% to about 50%, wherein the Effective Open Area is the ratio of total area of the apertures within the zone to the total area of the zone.

15. The disposable absorbent article of claim 1, wherein each of the apertures in the first plurality of apertures, the second plurality of apertures, and the third plurality of apertures comprises an Effective Aperture Area between about 0.1 mm$^2$ to about 15 mm$^2$.

16. The disposable absorbent article of claim 15, wherein each of the first plurality of apertures has a higher Effective Aperture Area than each of the second plurality of apertures or the third plurality of apertures.

17. The disposable absorbent article of claim 16, wherein each of the second plurality of apertures has a higher Effective Aperture Area than each of the third plurality of apertures.

18. The disposable absorbent article of claim 1, wherein the web comprises a single layer or a laminate.

19. The disposable absorbent article of claim 18, wherein the single layer or laminate comprises at least one nonwoven layer.

* * * * *